US008796177B2

(12) United States Patent
Mann et al.

(10) Patent No.: US 8,796,177 B2
(45) Date of Patent: Aug. 5, 2014

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND ACETYL-COA CARBOXYLASE (ACCASE) INHIBITORS

(71) Applicant: Dow Agrosciences LLC, Indianapolis, IN (US)

(72) Inventors: Richard K. Mann, Franklin, IN (US); Carla N. Yerkes, Crawfordsville, IN (US); Monte R. Weimer, Pittsboro, IN (US); Nelson M. Carranza, Ibague (CO)

(73) Assignee: Dow Agrosciences LLC, Indianapolis, IN (US)

( * ) Notice: Subject to any disclaimer, the term of this patent is extended or adjusted under 35 U.S.C. 154(b) by 0 days.

(21) Appl. No.: 13/839,043

(22) Filed: Mar. 15, 2013

(65) Prior Publication Data
US 2014/0031228 A1 Jan. 30, 2014

Related U.S. Application Data

(60) Provisional application No. 61/675,103, filed on Jul. 24, 2012.

(51) Int. Cl.
A01N 25/26 (2006.01)
A01N 43/40 (2006.01)

(52) U.S. Cl.
USPC .......................................... 504/100; 504/130

(58) Field of Classification Search
None
See application file for complete search history.

(56) References Cited

U.S. PATENT DOCUMENTS

| | | | |
|---|---|---|---|
| 7,314,849 B2 * | 1/2008 | Balko et al. | 504/244 |
| 7,622,641 B2 * | 11/2009 | McCutchen et al. | 800/300 |
| 2009/0062121 A1 | 3/2009 | Satchivi et al. | |
| 2010/0137137 A1 | 6/2010 | Rosinger et al. | |
| 2011/0082162 A1 * | 4/2011 | Lorsbach et al. | 514/274 |
| 2011/0207607 A1 * | 8/2011 | Satchivi et al. | 504/105 |
| 2012/0115727 A1 | 5/2012 | Satchivi et al. | |
| 2012/0190551 A1 * | 7/2012 | Yerkes et al. | 504/242 |
| 2013/0109569 A1 * | 5/2013 | Dave et al. | 504/130 |
| 2013/0310256 A1 * | 11/2013 | Yerkes et al. | 504/103 |
| 2014/0031210 A1 * | 1/2014 | Yerkes et al. | 504/103 |
| 2014/0031211 A1 * | 1/2014 | Yerkes et al. | 504/103 |
| 2014/0031212 A1 * | 1/2014 | Yerkes et al. | 504/103 |
| 2014/0031213 A1 * | 1/2014 | Yerkes et al. | 504/103 |
| 2014/0031214 A1 * | 1/2014 | Yerkes et al. | 504/103 |
| 2014/0031215 A1 * | 1/2014 | Yerkes et al. | 504/103 |
| 2014/0031216 A1 * | 1/2014 | Yerkes et al. | 504/103 |
| 2014/0031217 A1 * | 1/2014 | Yerkes et al. | 504/103 |
| 2014/0031218 A1 * | 1/2014 | Mann et al. | 504/103 |
| 2014/0031219 A1 * | 1/2014 | Yerkes et al. | 504/103 |
| 2014/0031220 A1 * | 1/2014 | Yerkes et al. | 504/103 |
| 2014/0031221 A1 * | 1/2014 | Yerkes et al. | 504/103 |
| 2014/0031222 A1 * | 1/2014 | Yerkes et al. | 504/103 |
| 2014/0031227 A1 * | 1/2014 | Yerkes et al. | 504/128 |
| 2014/0031229 A1 * | 1/2014 | Mann et al. | 504/136 |

FOREIGN PATENT DOCUMENTS

WO    WO 2007082098    * 7/2007

OTHER PUBLICATIONS

Synthesis of Esters: Esterification Reactions, obtained via google.com in U.S. Appl. No. 13/840,306, obtained online Mar. 8, 2014.*
Steglich Esterification, Organic Chemistry Portal in U.S. Appl. No. 13/840,306.*
Chui, M.P. Non-Final Office Action in U.S. Appl. No. 13/840,306, Mar. 13, 2014, pp. 1-12, USPTO.*
Pryor, A.N., Notice of Allowance and Fee(s) Due for U.S. Appl. No. 13/832,978, Apr. 9, 2014, pp. 1-13, USPTO.*
Pryor, A.N., Notice of Allowance and Fee(s) Due for U.S. Appl. No. 13/833,315, May 12, 2014, pp. 1-8, USPTO.*
Pryor, A.N., Notice of Allowance and Fee(s) Due for U.S. Appl. No. 13/833,315, Mar. 20, 2014, pp. 1-1, USPTO.*
Pryor, A.N., Notice of Allowance and Fee(s) Due for U.S. Appl. No. 13/833,362, May 29, 2014, pp. 1-8, USPTO.*
Pryor, A.N., Notice of Allowance and Fee(s) Due for U.S. Appl. No. 13/833,372, May 14, 2014, pp. 1-8, USPTO.*

(Continued)

Primary Examiner — Alton Pryor
(74) Attorney, Agent, or Firm — Faegre Baker Daniels LLP

(57) ABSTRACT

Provided herein are synergistic herbicidal compositions containing and methods utilizing (a) a compound of formula (I):

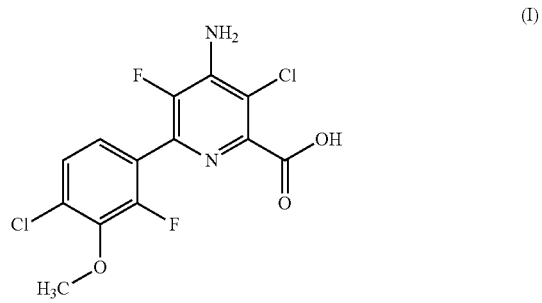

(I)

or an agriculturally acceptable salt or ester thereof and (b) an ACCase inhibitors, including. e.g., clethodim, clodinafop-propargyl, cyhalofop-R-butyl, diclofop-methyl, fenoxaprop-P-ethyl, fluazifop-P-butyl, haloxyfop-R-methyl, metamifop, pinoxaden, profoxydim, quizalofop-P-ethyl, sethoxydim and tralkoxydim, provide synergistic weed control of undesirable vegetation in rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) or rights of way (ROW).

15 Claims, No Drawings

(56) References Cited

OTHER PUBLICATIONS

Pryor, A.N., Notice of Allowance and Fee(s) Due for U.S. Appl. No. 13/833,659, Mar. 17, 2014, pp. 1-12, USPTO.*
Pryor, A.N., Notice of Allowance and Fee(s) Due for U.S. Appl. No. 13/833,923, May 2, 2014, pp. 1-9, USPTO.*
Pryor, A.N., Notice of Allowance and Fee(s) Due for U.S. Appl. No. 13/833,965, Apr. 1, 2014, pp. 1-8, USPTO.*
Pryor, A.N., Notice of Allowance and Fee(s) Due for U.S. Appl. No. 13/834,326, May 13, 2014, pp. 1-4, USPTO.*
Pryor, A.N., Notice of Allowance and Fee(s) Due for U.S. Appl. No. 13/834,326, Apr. 2, 2014, pp. 1-9, USPTO.*
Pryor, A.N., Notice of Allowance and Fee(s) Due for U.S. Appl. No. 13/836,653 Apr. 2, 2014, pp. 1-8, USPTO.*
Pryor, A.N., Notice of Allowance and Fee(s) Due for U.S. Appl. No. 13/837,990, Apr. 1, 2014, pp. 1-8, USPTO.*
Pryor, A.N., Notice of Allowance and Fee(s) Due for U.S. Appl. No. 13/834,706, Mar. 12, 2014, pp. 1-13, USPTO.*
Pryor, A.N., Notice of Allowance and Fee(s) Due for U.S. Appl. No. 13/840,236, Apr. 25, 2014, pp. 1-8, USPTO.*
Pryor, A.N., Notice of Allowance and Fee(s) Due for U.S. Appl. No. 13/840,303, Apr. 25, 2014, pp. 1-8, USPTO.*
Pryor, A.N., Notice of Allowance and Fee(s) Due for U.S. Appl. No. 13/840,346, Jun. 4, 2014, pp. 1-8, USPTO.*
Pryor, A.N., Notice of Allowance and Fee(s) Due for U.S. Appl. No. 13/840,419, May 5, 2014, pp. 1-8, USPTO.*
Pryor, A.N., Notice of Allowance and Fee(s) Due for U.S. Appl. No. 13/840,488, May 2, 2014, pp. 1-8, USPTO.*
Thomas, S, Written Opinion of the International Search Authority for PCT/US2013/051320, Dec. 6, 2013, pp. 1-5, ISA/US.
Thomas, S, International Search Report for PCT/US2013/051320, Dec. 6, 2013, pp. 1-4, ISA/US.

* cited by examiner

HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND ACETYL-COA CARBOXYLASE (ACCASE) INHIBITORS

PRIORITY CLAIM

This application claims the benefit of U.S. provisional patent application No. 61/675,103 filed on Jul. 24, 2012, this provisional application is incorporated herein by reference in its entirety.

FIELD

Provided herein are herbicidal compositions comprising and methods of controlling undesirable vegetation utilizing (a) 4-amino-3-chloro-5-fluoro-6-(4-chloro-2-fluoro-3-methoxyphenyl)pyridine-2-carboxylic acid or an agriculturally acceptable ester or salt thereof and (b) an acetyl-CoA carboxylase (ACCase) inhibitor.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

A first embodiment includes herbicidal compositions, comprising: a herbicidally effective amount of (a) a compound of the formula (I)

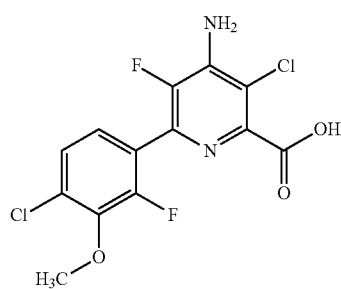

or an agriculturally acceptable salt or ester thereof: and (b) ACCase inhibitors, or a salt or ester thereof.

A second embodiment includes a composition of according to the first embodiment, wherein (a) is a $C_{1-4}$ alkyl or benzyl ester of compound (I).

A third embodiment includes a composition of according to the first embodiment wherein (a) is a benzyl ester of compound (I).

A fourth embodiment includes a composition of according to the first embodiment wherein (a) is the compound of formula (I), which is the carboxylic acid.

A fifth embodiment includes compositions of the first, second, third, or fourth embodiments, wherein (b) is selected from the group consisting of: clethodim, clodinafop-propargyl, cyhalofop-R-butyl, diclofop-methyl, fenoxaprop-P-ethyl, fluazifop-P-butyl, haloxyfop-R-methyl, metamifop, pinoxaden, profoxydim, quizalofop-P-ethyl, sethoxydim or tralkoxydim.

A sixth embodiment includes a composition of the first embodiment, wherein (a) is the compound of formula (I) or an agriculturally acceptable benzyl ester and (b) is clethodim.

A seventh embodiment includes a composition of the first embodiment, wherein (a) is the compound of formula (I) or an agriculturally acceptable benzyl ester and (b) is clodinafop-propargyl.

An eighth embodiment includes a composition of the first embodiment, wherein (a) is the compound of formula (I) or an agriculturally acceptable benzyl ester and (b) is cyhalofop-R-butyl.

An ninth embodiment includes a composition of the first embodiment, wherein (a) is the compound of formula (I) or an agriculturally acceptable benzyl ester and (b) is diclofop-methyl.

An tenth embodiment includes a composition of the first embodiment, wherein (a) is the compound of formula (I) or an agriculturally acceptable benzyl ester and (b) is fenoxaprop-P-ethyl.

An eleventh embodiment includes a composition of the first embodiment, wherein (a) is the compound of formula (I) or an agriculturally acceptable benzyl ester and (b) is fluazifop-P-butyl.

An twelfth embodiment includes a composition of the first embodiment, wherein (a) is the compound of formula (I) or an agriculturally acceptable benzyl ester and (b) is haloxyfop-R-methyl.

A thirteenth embodiment includes a composition of the first embodiment, wherein (a) is the compound of formula (I) or an agriculturally acceptable benzyl ester and (b) is metamifop.

A fourteenth embodiment includes a composition of the first embodiment, wherein (a) is the compound of formula (I) or an agriculturally acceptable benzyl ester and (b) is pinoxaden.

A fifteenth embodiment includes a composition of the first embodiment, wherein (a) is the compound of formula (I) or an agriculturally acceptable benzyl ester and (b) is profoxydim.

A sixteenth embodiment includes a composition of the first embodiment, wherein (a) is the compound of formula (I) or an agriculturally acceptable benzyl ester and (b) is quizalofop-P-ethyl.

A seventeenth embodiment includes a composition of the first embodiment, wherein (a) is the compound of formula (I) or an agriculturally acceptable benzyl ester and (b) sethoxydim.

An eighteenth embodiment includes a composition of the first embodiment, wherein (a) is the compound of formula (I) or an agriculturally acceptable benzyl ester and (b) is tralkyoxydim.

A nineteenth embodiment includes composition according to the first through the eighteenth embodiments further comprising a herbicide safener.

A twentieth embodiment includes a composition according to the first embodiment wherein the ratios the compound of formula (I) or agriculturally acceptable salt or ester thereof to clethodim or an agriculturally acceptable salt or ester thereof, expressed in units of weight to weight (g ro g), gae/ha to gai/ha, or gae/ha to gae/ha, are within the range of about 1:140 to about 9:1.

A twenty-first embodiment includes a composition according to the first embodiment wherein the ratios the compound of formula (I) or agriculturally acceptable salt or ester thereof to clodinafop-propargyl or an agriculturally acceptable salt or ester thereof, expressed in units of weight to weight (g to g), gae/ha to gai/ha, or gae/ha to gae/ha, are within the range of about 1:40 to about 60:1.

A twenty-second embodiment includes a composition according to the first embodiment wherein the ratios the compound of formula (I) or agriculturally acceptable salt or ester thereof to cyhalofop-R-butyl or an agriculturally acceptable salt or ester thereof, expressed in units of weigth to weight (g to g), gae/ha to gai/ha, or gae/ha to gae/ha, are within the range of about 1:155 to about 6:1.

A twenty-third embodiment includes a composition according to the first embodiment wherein the ratios the compound of formula (I) or agriculturally acceptable salt or ester thereof to diclofop-methyl or an agriculturally acceptable salt or ester thereof, expressed in units of weight to weight (g to g), gae/ha to gai/ha, or gae/ha to gae/ha, are within the range of about 1:560 to about 5:1.

A twenty-fourth embodiment includes a composition according to the first embodiment wherein the ratios the compound of formula (I) or agriculturally acceptable salt or ester thereof to fenoxaprop-P-ethyl or an agriculturally acceptable salt or ester thereof, expressed in units of weight to weight (g to g), gae/ha to gai/ha, or gae/ha to gae/ha, are within the range of about 1:170 to about 30:1, and the crop safeners isoxadifen-methyl and mefenpyr-diethyl are incorporated into the product.

A twenty-fifth embodiment includes a composition according to the first embodiment wherein the ratios the compound of formula (I) or agriculturally acceptable salt or ester thereof to fluazifop-P-butyl or an agriculturally acceptable salt or ester thereof, expressed in units of weight to weight (g to g), gae/ha to gai/ha, or gae/ha to gae/ha, are within the range of about 1:210 to about 3:1.

A twenty-sixth embodiment includes a composition according to the first embodiment wherein the ratios the compound of formula (I) or agriculturally acceptable salt or ester thereof to haloxyfop-R-methyl or an agriculturally acceptable salt or ester thereof, expressed in units of weight to weight (g to g), gae/ha to gai/ha, or gae/ha to gae/ha, are within the range of about 1:45 to about 10:1.

A twenty-seventh embodiment includes a composition according to the first embodiment wherein the ratios the compound of formula (I) or agriculturally acceptable salt or ester thereof to metamifop or an agriculturally acceptable salt or ester thereof, expressed in units of weight to weight (g to g), gae/ha to gai/ha, or gae/ha to gae/ha, are within the range of about 1:150 to about 6:1.

A twenty-eighth embodiment includes a composition according to the first embodiment wherein the ratios the compound of formula (I) or agriculturally acceptable salt or ester thereof to pinoxaden or an agriculturally acceptable salt or ester thereof, expressed in units of weight to weight (g to g), gae/ha to gai/ha, or gae/ha to gae/ha, are within the range of about 1:30 to about 150:1.

A twenty-ninth embodiment includes a composition according to the first embodiment wherein the ratios the compound of formula (I) or agriculturally acceptable salt or ester thereof toprofoxydim or an agriculturally acceptable salt or ester thereof, expressed in units of weight to weight (g to g), gae/ha to gai/ha, or gae/ha to gae/ha, are within the range of about 1:70 to about 29:1.

A thirtieth embodiment includes a composition according to the first embodiment wherein the ratios the compound of formula (I) or agriculturally acceptable salt or ester thereof to quizalofop-P-ethyl or an agriculturally acceptable salt or ester thereof, expressed in units of weight to weight (g to g), gae/ha to gai/ha, or gae/ha to gae/ha, are within the range of about 1:100 to about 12:1.

A thirty-first embodiment includes a composition according to the first embodiment wherein the ratios the compound of formula (I) or agriculturally acceptable salt or ester thereof to sethoxydim or an agriculturally acceptable salt or ester thereof, expressed in units of weight to weight (g to g), gae/ha to gai/ha, or gae/ha to gae/ha, are within the range of about 1:70 to about 29:1.

A thirty-second embodiment includes a composition according to the first embodiment wherein the ratios the compound of formula (I) or agriculturally acceptable salt or ester thereof to tralkoxydim or an agriculturally acceptable salt or ester thereof, expressed in units of weight to weight (g to g), gae/ha to gai/ha, or gae/ha to gae/ha, are within the range of about 1:38 to about 60:1.

A thirty-third embodiment includes any composition according to the first through the thirty-second embodiments that, further comprising an agriculturally acceptable adjuvant, and/or carrier and/or herbicide safener.

A thirty-fourth embodiment includes any composition according to the first through the thirty-third embodiments, wherein synergy between herbicides is determined by the Colby equation.

A thirty-fifth embodiment includes any composition according to the first embodiment wherein (b) is cyhalofop-butyl or carboxylic acid, carboxylate salt, or ester thereof, wherein the composition further comprises penoxsulam, bentazon-sodium, triclopyr, bispyribac-sodium, imazamox, benzobicyclon, quinclorac, glyphosate, glufosinate, benfuresate, fentrazamide, indanofan, ipfencarbazone, mefenacet, oxazichlomefone, pretilachlor, propyrisulfuron, pyraclonil, pyriftalid, or pyrimisulfan, or an agriculturally acceptable salt, carboxylic acid, carboxylate salt, or ester thereof, in combination as a synergistic 3 way/ternary mixture.

A thirty-sixth embodiment includes any composition according to the first embodiment wherein (b) is fenoxaprop, metamifop, or profoxydim, or agriculturally acceptable salt, ester, carboxylate salt, or carboxylic acid thereof, wherein the composition further comprises penoxsulam, or an agriculturally acceptable salt, carboxylic acid, carboxylate salt, or ester thereof, in combination as a synergistic 3 way/ternary mixture.

A thirty-seventh embodiment includes methods for controlling undesirable vegetation comprising the steps of contacting the vegetation or the locus thereof with or applying to the soil or water to prevent the emergence or growth of vegetation the at least one composition according to the first through the thirty-sixth embodiments.

A thirty-eighth embodiment includes methods for controlling undesirable vegetation comprising the steps of contacting the vegetation or the locus thereof with or applying to the soil or water to prevent the emergence or growth of vegetation utilizing a herbicidally effective amount of (a) a compound of the formula (I)

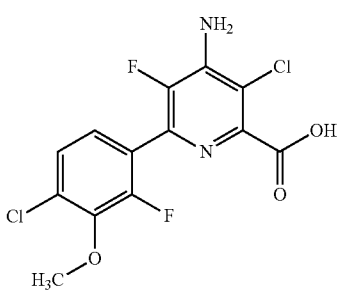

(I)

or an agriculturally acceptable salt or ester of thereof, and (b) an ACCase inhibitor.

The thirty-ninth embodiment includes methods of the thirty-seventh and thirty-eighth embodiments, wherein the undesirable vegetation is controlled in rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) or rights of way (ROW).

wherein the undesirable vegetation is immature.

The forty-first embodiment includes methods of the thirty-seventh and thirty-eighth embodiments wherein the compounds (a) and (b) are applied to water.

The forty-second embodiment includes methods according to the forty-first embodiment, wherein the water is part of a flooded rice paddy.

The forty-third embodiment includes methods according to the thirty-seventh and thirty-eighth embodiments, wherein compounds (a) and (b) are applied pre-emergently to the weed or crop.

The forty-fourth embodiment includes methods according to the thirty-seventh and thirty-eighth embodiments, wherein compounds (a) and (b) are applied post-emergently to the weed or crop.

The forty-fifth embodiment includes methods according to the thirty-seventh and thirty-eighth embodiments, wherein the undesirable vegetation is controlled in glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS) inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, triazine-, or bromoxynil-tolerant crops.

The forty-sixth embodiment includes methods according to the forty-fifth embodiment, wherein the tolerant crop possesses multiple or stacked traits conferring tolerance to multiple herbicides or multiple modes of action.

The forty-seventh embodiment includes methods according to the thirty-seventh and thirty-eighth embodiments, wherein the undesirable vegetation comprises a herbicide resistant or tolerant weed.

The forty-eighth embodiment includes methods according to the forty-seventh embodiment, wherein the resistant or tolerant weed is a biotype with resistance or tolerance to multiple herbicides, multiple chemical classes, or multiple herbicide modes-of-action or via multiple resistance mechanisms.

The forty-ninth embodiment includes methods according to the forty-seventh embodiment wherein the resistant or tolerant weed is a biotype resistant or tolerant to acetolactate synthase (ALS) or acetohydroxy acid synthase (AHAS) inhibitors, photosystem II inhibitors, acetyl CoA carboxylase (ACCase) inhibitors, synthetic auxins, auxin transport inhibitors, photosystem I inhibitors, 5-enolpyruvylshikimate-3-phosphate (EPSP) synthase inhibitors, microtubule assembly inhibitors, fatty acid and lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

Provided herein are herbicidal compositions comprising a methods of controlling undesirable vegetation utilizing a herbicidally effective amount of (a) a compound of the formula (I).

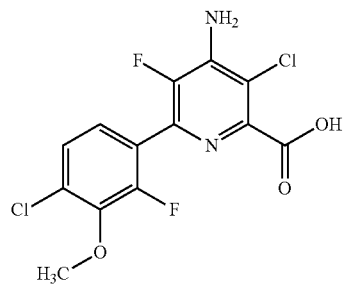

(I)

or an agriculturally acceptable salt or ester of thereof, and (b) an ACCase inhibitor. Exemplary ACCase inhibitors include, but are not limited to, clethodim, clodinafop-propargyl, cyhalofop-R-butyl, diclofop-methyl, fenoxaprop-P-ethyl, fluazifop-P-butyl, haloxyfop-R-methyl, metamifop, pinoxaden, profoxydim, quizalofop-P-ethyl, sethoxydim or tralkoxydim. The compositions may also contain an agriculturally acceptable adjuvant or carrier.

DETAILED DESCRIPTION

Definitions

As used herein, the compound of formula (I) has the following structure:

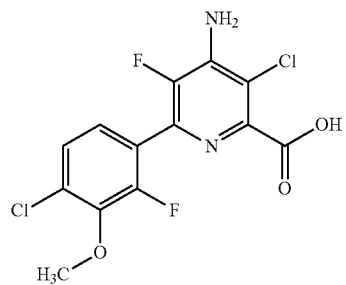

(IH)

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

Without being limited to any theory, ACCase inhibitors believed to inhibit to any extent acetyl coenzyme A carboxylase (ACCase), an enzyme involved in fatty acid synthesis. Exemplary ACCase inhibitors include, but are not limited to, aryloxyphenoxy propionates and the cyclohexanediones. Further examples include, but are not limited to, clethodim, clodinafop-propargyl, cyhalofop-R-butyl, diclofop-methyl, fenoxaprop-P-ethyl, fluazifop-P-butyl, haloxyfop-R-methyl, metamifop, pinoxaden, profoxydim, quizalofop-P-ethyl, sethoxydim and tralkoxydim.

As used herein, clethodim is 2-[1-[[[(2E)-3-chloro-2-propen-1-yl]oxy]imino]propyl]-5-[2-(ethylthio)propyl]-3-hydroxy-2-cyclohexen-1-one and possesses the following structure:

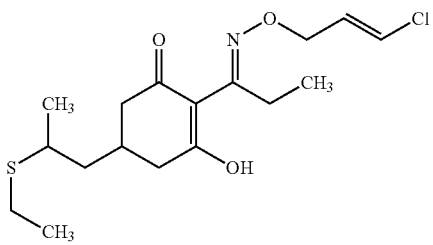 [SMILES: CCSC(C)CC1CC(=O)C(/C(CC)=N/OC/C=C/Cl)=C(O)C1]

This compound is described in Tomlin, C., ed. A World Compendium The Pesticide Manual. 15$^{th}$ ed. Alton: BCPC Publications, 2009 (hereafter "*The Pesticide Manual*, Fifteenth Edition, 2009."). Exemplary uses of clethodim include its use as a herbicide for, e.g., post-emergence control of annual and perennial grasses in broadleaf crops, vegetables, trees and vines.

As used herein, clodinafop-propargyl is 2-propynyl (2R)-2-[4-[(5-chloro-3-fluoro-2-pyridinyl)oxy]phenoxy]propanoate and possesses the following structure:

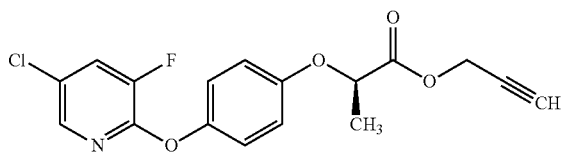 [SMILES: C#CCOC(=O)[C@@H](C)Oc1ccc(Oc2ncc(Cl)cc2F)cc1]

This compound is described in *The Pesticide Manual*, Fifteenth Edition, 2009. Exemplary uses of clodinafop-propargyl include its use as a herbicide for, e.g., post-emergence control of annual grasses, including, e.g., *Avena, Lolium, Setaria, Phalaris* and *Alopecurus* spp., in cereals.

As used herein, cyhalofop-butyl is butyl (2R)-2-[4-(4-cyano-2-fluorophenoxy)phenoxy]propanoate and possesses the following structure:

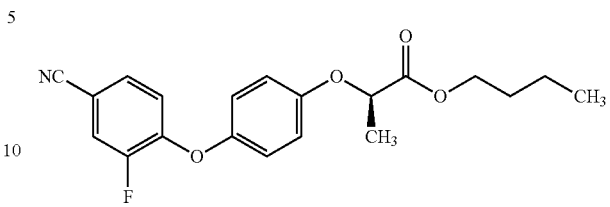

This compound is described in *The Pesticide Manual*, Fifteenth Edition, 2009. Exemplary uses of cyhalofop-butyl include its use as a herbicide for, e.g., post-emergence control of annual and perennial grass weeds in seeded and transplanted rice.

As used herein, diclofop-methyl is methyl 2-[4-(2,4-dichlorophenoxy)phenoxy]propanoate and possesses the following structure:

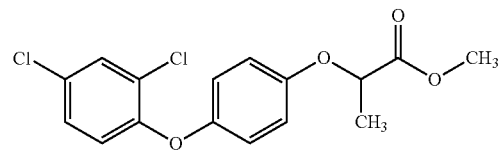 [SMILES: COC(=O)C(C)Oc1ccc(Oc2ccc(Cl)cc2Cl)cc1]

This compound is described in *The Pesticide Manual*, Fifteenth Edition, 2009. Exemplary uses of diclofop-methyl include its use as a herbicide for, e.g., post-emergence control of wild oats, wild millets, and other annual grass weeds in wheat, barley, rye, red fescue, and broadleaf crops.

As used herein, fenoxaprop-P-ethyl is ethyl (2R)-2-[4-[(6-chloro-2-benzoxazolyl)oxy]phenoxy]propanoate and possesses the following structure:

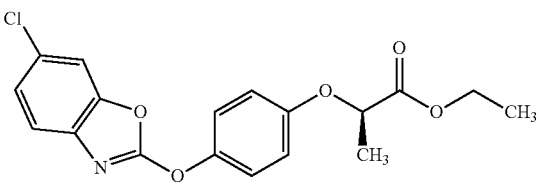 [SMILES: CCOC(=O)[C@@H](C)Oc1ccc(Oc2nc3ccc(Cl)cc3o2)cc1]

This compound is described in *The Pesticide Manual*, Fifteenth Edition, 2009. Exemplary uses of fenoxaprop-P-ethyl include its use as a herbicide for, e.g., control of annual and perennial grass weeds in crops including rice.

As used herein, fluazifop-P-butyl is butyl (2R)-2-[4-[[5-(trifluoromethyl)-2-pyridinyl]oxy]phenoxy]propanoate and possesses the following structure:

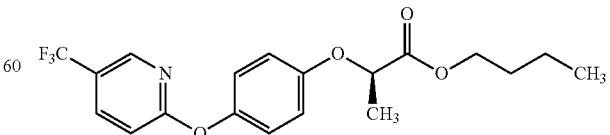

This compound is described in *The Pesticide Manual*, Fifteenth Edition, 2009. Exemplary uses of fluazifop-P-butyl include its use as a herbicide for, e.g., post-emergence control of wild oats, volunteer cereals, and annual and perennial grass weeds in oilseed rape, sugar beet, fodder beet, potatoes, vegetables, cotton, soya beans, pome fruit, stone fruit, bush fruit, vines, citrus fruit, pineapples, bananas, strawberries, sunflowers, alfalfa, coffee, ornamentals and other broadleaf crops. Fluazifop-P-butyl can be used in combination with safeners, e.g., isoxadifen-ethyl or mefenpyr-diethyl.

As used herein, haloxyfop-P-methyl is methyl (2R)-2-[4-[[3-chloro-5-(trifluoromethyl)-2-pyridinyl]oxy]phenoxy]propanoate and possesses the following structure:

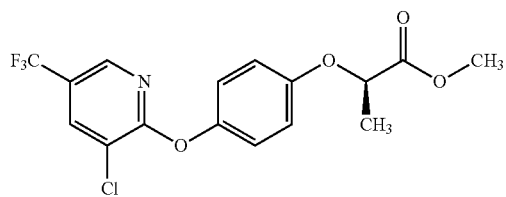 [SMILES: COC(=O)[C@@H](C)Oc1ccc(Oc2ncc(C(F)(F)F)cc2Cl)cc1]

This compound is described in *The Pesticide Manual*, Fifteenth Edition, 2009. Exemplary uses of haloxyfop-P-methyl include its use as a herbicide for, e.g., post-emergence control of annual and perennial grasses in a variety of crops.

As used herein, metamifop is (2R)-2-[4-[(6-chloro-2-benzoxazolyl)oxy]phenoxy]-N-(2-fluorophenyl)-N-methylpropanamide and possesses the following structure:

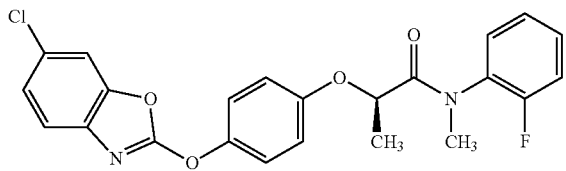 [SMILES: C[C@@H](Oc1ccc(Oc2nc3ccc(Cl)cc3o2)cc1)C(=O)N(C)c1ccccc1F]

This compound is described in *The Pesticide Manual*, Fifteenth Edition, 2009. Exemplary uses of metamifop include its use as a herbicide for, e.g., post-emergence control of annual and perennial grasses in a variety of crops, including rice.

As used herein, pinoxaden is 8-(2,6-diethyl-4-methylphenyl)-1,2,4,5-tetrahydro-7-oxo-7H-pyrazolo[1,2-d][1,4,5]oxadiazepin-9-yl-2,2-dimethylpropanoate and possesses the following structure:

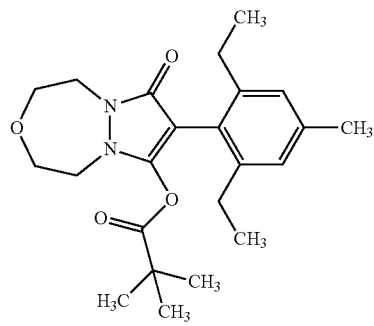 [SMILES: CCc1cc(C)cc(CC)c1-c1c(OC(=O)C(C)(C)C)n2n(c1=O)CCOCC2]

This compound is described in *The Pesticide Manual*, Fifteenth Edition, 2009. Exemplary uses of pinoxaden include its use as a herbicide for, e.g., post-emergence control of annual grasses, including *Alopecurus, Apera, Avena, Lolium, Phalaris* and *Setaria* spp., in wheat and barley.

As used herein, profoxydim is 2-[1-[[2-(4-chlorophenoxy)propoxy]imino]butyl]-3-hydroxy-5-(tetrahydro-2H-thiopyran-3-yl)-2-cyclohexen-1-one and possesses the following structure:

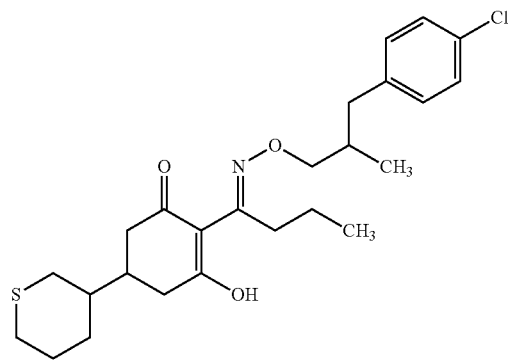 [SMILES: CCC/C(=N\OCC(C)Cc1ccc(Cl)cc1)C1=C(O)CC(C2CCCSC2)CC1=O]

This compound is described in *The Pesticide Manual*, Fifteenth Edition, 2009. Exemplary uses of profoxydim include its use as a herbicide for, e.g., control of grass weeds in rice.

As used herein, quizalofop-P-ethyl is ethyl (2R)-2-[4-[(6-chloro-2-quinoxalinyl)oxy]phenoxy]propanoate and possesses the following structure:

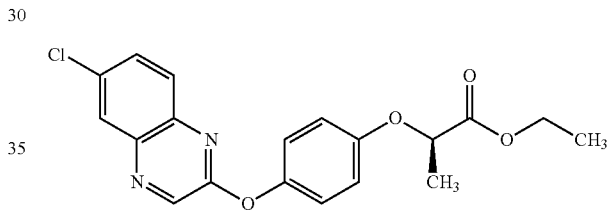

This compound is described in *The Pesticide Manual*, Fifteenth Edition, 2009. Exemplary uses of quizalofop-P-ethyl include its use as a herbicide for, e.g., selective post-emergence control of annual and perennial grass weeds in crops.

As used herein, sethoxydim is 2-[1-(ethoxyimino)butyl]-5-[2-(ethylthio)propyl]-3-hydroxy-2-cyclohexen-1-one and possesses the following structure:

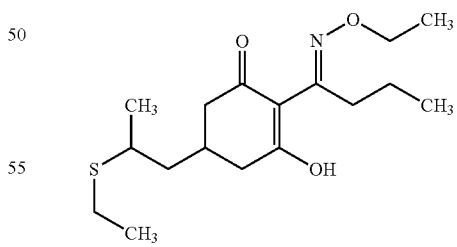

This compound is described in *The Pesticide Manual*, Fifteenth Edition, 2009. Exemplary uses of sethoxydim include its use as a herbicide for, e.g., control of annual and perennial grasses in broadleaf crops.

As used herein, tralkoxydim is 2-[1-(ethoxyimino)propyl]-3-hydroxy-5-(2,4,6-trimethylphenyl)-2-cyclohexen-1-one and possesses the following structure:

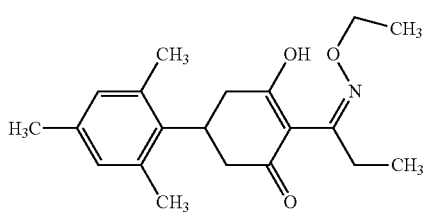 [SMILES: CCO/N=C(/CC)C1=C(O)CC(c2c(C)cc(C)cc2C)CC1=O]

This compound is described in *The Pesticide Manual*, Fifteenth Edition, 2009. Exemplary uses of tralkoxydim include its use as a herbicide for, e.g., post-emergence control of annual grass weeds in wheat and barley.

As used herein, herbicide means a compound, e.g., active ingredient that kills, controls or otherwise adversely modifies the growth of plants.

As used herein, a herbicidally effective or vegetation controlling amount is an amount of active ingredient which causes an adversely modifying effect to the vegetation e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as preemergence, postemergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines. Exemplary cations include sodium, potassium, magnesium, and aminium cations of the formula:

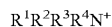

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising a herbicidally effective amount of (a) a compound of the formula (I)

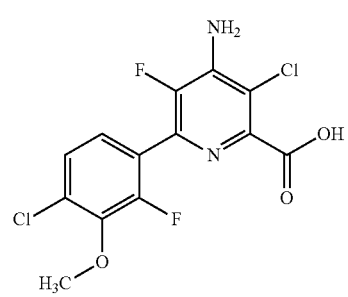

(I)

or an agriculturally acceptable salt or ester of thereof, and (b) an ACCase inhibitor. In certain embodiments, the ACCase inhibitor is clethodim, clodinafop-propargyl, cyhalofop-R-butyl, diclofop-methyl, fenoxaprop-P-ethyl, fluazifop-P-butyl, haloxyfop-R-methyl, metamifop, pinoxaden, profoxydim, quizalofop-P-ethyl, sethoxydim or tralkoxydim or derivative thereof, e.g., salt, carboxylic acid, carboxylate salt, or ester thereof.

Provided herein are also methods of controlling undesirable vegetation comprising contacting the vegetation or the locus thereof, i.e., are adjacent to the vegetation, with or applying to the soil or water to prevent the emergence or growth of vegetation a herbicidally effective amount of the compound of formula (I) and (b) an ACCase inhibitor. In certain embodiments, the methods employ the compositions described herein.

Furthermore, in some embodiments, the combination of compound (I) or agriculturally acceptable salt or ester thereof and ACCase inhibitors, or an agriculturally acceptable salt or ester thereof exhibits synergism, e.g., the herbicidal active ingredients are more effective in combination than when applied individually. Synergism has been defined as "an interaction of two or more factors such that the effect when combined is greater than the predicted effect based on the response of each factor applied separately." Senseman, S., ed.

Herbicide Handbook. 9$^{th}$ ed. Lawrence: Weed Science Society of America, 2007. In certain embodiments, the compositions exhibit synergy as determined by the Colby's equation. Colby, S. R. 1967. Calculation of the synergistic and antagonistic response of herbicide combinations. Weeds 15:20-22.

In certain embodiments of the compositions and methods described herein, the compound of formula (I), i.e., the carboxylic acid, is employed. In certain embodiments, a carboxylate salt of the compound of formula (I) is employed. In certain embodiments, an aralkyl or alkyl ester is employed. In certain embodiments, a benzyl, substituted benzyl, or $C_{1-4}$ alkyl, e.g., n-butyl ester is employed. In certain embodiments, the benzyl ester is employed.

In some embodiments, the compound of formula (I) or salt or ester thereof and ACCase inhibitor are formulated in one composition, tank mixed, applied simultaneously, or applied sequentially.

Herbicidal activity is exhibited by the compounds when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) and rights of way (ROW).

In certain embodiments, the compositions and methods provided herein are utilized to control weeds in rice. In certain embodiments, the rice is direct-seeded, water-seeded, or transplanted rice.

The compositions and methods described herein be used to control undesirable vegetation in glyphosate-tolerant-, 5-enolpyruvylshikimate-3-phosphate (EPSP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenylpyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant- and bromoxynil-tolerant-crops (such as, but not limited to, soybean, cotton, canola/oilseed rape, rice, cereals, corn, sorghum, sunflower, sugar beet, sugarcane, turf, etc.), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, PPO inhibitors, triazines, and bromoxynil The compositions and methods may be used in controlling undesirable vegetation in crops possessing multiple or stacked traits conferring tolerance to multiple chemistries and/or inhibitors of multiple modes of action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, tank mix or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The compositions and methods provided herein are utilized to control undesirable vegetation. Undesirable vegetation includes, but is not limited to, undesirable vegetation that occurs in rice, cereals, wheat, barley, oats, rye, sorghum, corn/maize, sugarcane, sunflower, oilseed rape, canola, sugar beet, soybean, cotton, pineapple, range and pasture, grasslands, fallowland, turf, tree and vine orchards, aquatics, plantation crops, vegetables, industrial vegetation management (IVM) and rights of way (ROW).

In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R. D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schuh. (gulf cockspur, ECHCV), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa phyllopogon* (Stapf) Koso-Pol. (rice barnyardgrass, ECHPH), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA),

*Oryza* species (red and weedy rice, ORYSS), *Panicum dichotomiflorum* (L.) Michx. (fall panicum, PANDI), *Paspalum dilatatum* Poir. (dallisgrass, PASDI), *Rottboellia cochinchinensis* (Lour.) W. D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Cyperus serotinus* ROTTB./C. B. Clarke (CYPSE), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia* species (LUDSS), *Ludwigia linifolia* Poir. (southeastern primrose-willow, LUDLI), *Ludwigia octovalvis* (Jacq.) Raven (longfruited primrose-willow, LUDOC), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp *sesbania*, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Amaranthus retroflexus* L. (redroot pigweed, AMARE), *Brassica* species (BRSSS), *Chenopodium album* L. (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis* species (SINSS), *Sinapis arvensis* L. (wild mustard, SINAR) *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, fallowland, IVM and ROW. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Daucus carota* L. (wild carrot, DAUCA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly *sida*, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops, tree and vine crops and perennial crops. In certain embodiments, the undesirable vegetation is *Alopecurus myosuroides* Huds. (blackgrass, ALOMY), *Avena fatua* L. (wild oat, AVEFA), *Brachiaria decumbens* Stapf. or Urochloa decumbens (Stapf) R. D. Webster (Surinam grass, BRADC), *Brachiaria brizantha* (Hochst. ex A. Rich.) Stapf. or *Urochloa brizantha* (Hochst. ex A. Rich.) R. D. (beard grass, BRABR), *Brachiaria platyphylla* (Groseb.) Nash or *Urochloa platyphylla* (Nash) R. D. Webster (broadleaf signalgrass, BRAPP), *Brachiaria plantaginea* (Link) Hitchc. or *Urochloa plantaginea* (Link) R. D. Webster (alexandergrass, BRAPL), *Cenchrus echinatus* L. (southern sandbar, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall *panicum*, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred anoda, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. (broadleaf buttonweed, BOILF), *Spermacose latifolia* (broadleaved button weed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. or *Conyza canadensis* (L.) Cronq. (Canadian fleabane, ERICA),

*Conyza sumatrensis* (Retz.) E. H. Walker (tall fleabane, ERIFL), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Sida* species (*sida*, SIDSS), *Sida spinosa* L. (prickly *sida*, SIDSP), *Sinapis arvensis* L. (wild mustard, SINAR), *Solanum ptychanthum* Dunal (eastern black nightshade, SOLPT), *Tridax procumbens* L. (coat buttons, TRQPR), *Tridax procumbens* L. (coat buttons, TRQPR), or *Xanthium strumarium* L. (common cocklebur, XANST).

In some embodiments, the methods provided herein are utilized to control undesirable vegetation in turf. In certain embodiments, the undesirable vegetation is *Bellis perennis* L. (English daisy, BELPE), *Cyperus esculentus* L. (yellow nutsedge, CYPES), *Cyperus* species (CYPSS), *Digitaria sanguinalis* (L.) Scop. (large crabgrass, DIGSA), *Diodia virginiana* L. (Virginia buttonweed, DIQVI), *Euphorbia* species (spurge, EPHSS), *Glechoma hederacea* L. (ground ivy, GLEHE), *Hydrocotyle umbellata* L. (dollarweed, HYDUM), *Kyllinga* species (*kyllinga*, KYLSS), *Lamium amplexicaule* L. (henbit, LAMAM), *Murdannia nudiflora* (L.) Brenan (doveweed, MUDNU), *Oxalis* species (woodsorrel, OXASS), *Plantago major* L. (broadleaf plantain, PLAMA), *Plantago lanceolata* L. (buckhorn/narrowleaf plantain, PLALA), *Phyllanthus urinaria* L. (chamberbitter, PYLTE), *Rumex obtusifolius* L. (broadleaf dock, RUMOB), *Stachys floridana* Shuttlew. (Florida betony, STAFL), *Stellaria media* (L.) Vill. (common chickweed, STEME), *Taraxacum officinale* G. H. Weber ex Wiggers (dandelion, TAROF), *Trifolium repens* L. (white clover, TRFRE), or *Viola* species (wild violet, VIOSS).

In some embodiments, the compositions and methods provided herein are utilized to control undesirable vegetation consisting of grass, broadleaf and sedge weeds. In certain embodiments, the compositions and methods provided herein are utilized to control undesirable vegetation including *Avena, Brachiaria, Cyperus, Digitaria, Echinochloa, Fimbristylis, Ipomoea, Ischaemum, Leptochloa, Lolium, Schoenoplectus* and *Sesbania*.

In some embodiments, the combination of compound (I) or agriculturally acceptable ester or salt thereof and ACCase inhibitors or agriculturally acceptable salt or ester thereof is used to control *Avena fatua* L. (wild oat, AVEFA), *Brachiaria platyphylla* (Griseb.) Nash (broadleaf signalgrass, BRAPP), *Cyperus difformis* L. (smallflower umbrella sedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Digitaria sanguinalis* (L.) Scop. (large crabgrass, DIGSA), *Echinochloa crus-galli* (L.) Beauv. (barnyardgrass, ECHCG), *Echinochloa colona* (L.) Link (junglerice, ECHCO), *Fimbristylis miliacea* (L.) Vahl (globe fringerush, FIMMI), *Ipomoea hederacea* Jacq. (ivyleaf morningglory, IPOHE), *Ischaemum rugosum* Salisb. (saramollagrass, ISCRU), *Leptochloa chinensis* (L.) Nees (Chinese sprangletop, LEFCH), *Lolium multiflorum* Lam. (Italian ryegrass, LOLMU), *Schoenoplectus juncoides* (Roxb.) Palla (Japanese bulrush, SCPJU), *Schoenoplectus maritimus* (L.) Lye (sea clubrush, SCPMA), *Schoenoplectus mucronatus* (ricefield bulrush, SCPMU) and *Sesbania exaltata* (hemp sesbania, SEBEX).

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors, (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins, (e.g., benzoic acids, phenoxycarboxylic acids, pyridine carboxylic acids, quinoline carboxylic acids), auxin transport inhibitors (e.g., phthalamates, semicarbazones), photosystem I inhibitors, (e.g., bipyridyliums), 5-enolpyruvylshikimate-3-phosphate (EPSP) synthase inhibitors, (e.g., glyphosate), glutamine synthetase inhibitors (e.g., glufosinate, bialafos), microtubule assembly inhibitors, (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors, (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors, phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors, (e.g., callistemones, isoxazoles, pyrazoles, triketones), cellulose biosynthesis inhibitors (e.g., nitriles, benzamides, quinclorac, triazolocarboxamides), mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action and biotypes with multiple resistance or tolerance mechanisms (e.g., target site resistance or metabolic resistance).

In some embodiments, an agriculturally acceptable ester or salt of compound (I) is employed. In certain embodiments, an agriculturally acceptable ester is employed. In certain embodiments, the ester is a $C_{1-4}$ alkyl ester. In certain embodiments, the ester is an n-butyl ester. In certain embodiments, the ester is a benzyl ester. In certain embodiments, compound (I), which is a carboxylic acid, is employed.

In certain embodiments of the compositions and methods described herein, the compound of formula (I) or salt or ester thereof is used in combination with clethodim or salt or ester thereof. With respect to the compositions, in some embodiments, the weight ratio of the compound of formula (I) or salt or ester thereof to clethodim or salt or ester thereof is within the range of from about 1:140 to about 9:1. In certain embodiments, the weight ratio of the compound of formula (I) or salt or ester thereof to clethodim or salt or ester thereof is within the range of from about 1:48 to about 3:1. In certain embodiments, the compositions provided herein comprise the compound of formula (I) or its benzyl or n-butyl ester and clethodim. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 20 grams active ingredient per hectare (gai/ha) to about 580 gai/ha based on the total amount of active ingredients in the composition. In certain embodiments, the composition is applied at an application rate of from about 20 grams active ingredient per hectare (gai/ha) to about 260 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and clethodim or salt thereof, e.g., sequentially or simultaneously. In some embodiments, the clethodim or salt thereof is applied at a rate from about 17.5 gai/ha to about 280 gai/ha and the compound of formula (I) of salt or ester thereof is applied at a rate from about 2 gae/ha to about 300 gae/ha. In some embodiments, the clethodim or salt thereof is applied at a rate from about 70 gai/ha to about 280 gai/ha and the compound of formula (I) of salt or ester thereof is applied at a rate from about 8 gae/ha to about 32 gae/ha. In certain embodiments, the methods utilize the compound of formula (I), or its benzyl or n-butyl ester and clethodim for the control of BRAPP, DIGSA, CYPES and SCPJU.

In certain embodiments of the compositions and methods described herein, the compound of formula (I) or salt or ester thereof is used in combination with clodinafop-propargyl or salt, carboxylate salt, carboxylic acid, or ester thereof. With regard to the compositions, in some embodiments, the weight ratio of the compound of formula (I) or salt or ester thereof to clodinafop-propargyl or salt, carboxylate salt, carboxylic acid, or ester thereof is within the range of from about 1:40 to about 60:1. In certain embodiments, the weight ratio of the compound of formula (I) or salt or ester thereof to clodinafop-propargyl or salt, carboxylate salt, carboxylic acid, or ester thereof is within the range of from 1:36 to about 10:1. In certain embodiments, the weight ratio of the compound of formula (I) or salt or ester thereof to clodinafop-propargyl or salt, carboxylate salt, carboxylic acid, or ester thereof is within the range of from 1:6 to about 1:1.5. In certain embodiments, the compositions provided herein comprise the compound of formula (I) or its benzyl or n-butyl ester and clodinafop-propargyl. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 7 grams active ingredient per hectare (gai/ha) to about 380 gai/ha based on the total amount of active ingredients in the composition. In certain embodiments, the composition is applied at an application rate of from about 20 grams active ingredient per hectare (gai/ha) to about 40 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and clodinafop-propargyl or salt, carboxylate salt, carboxylic acid, or ester thereof, e.g., sequentially or simultaneously. In some embodiments, the clodinafop-propargyl or salt, carboxylate salt, carboxylic acid, or ester thereof is applied at a rate from about 5 gai/ha to about 80 gai/ha and the compound of formula (I) of salt or ester thereof is applied at a rate from about 2 gae/ha to about 300 gae/ha. In some embodiments, the clodinafop-propargyl or salt, carboxylate salt, carboxylic acid, or ester thereof is applied at a rate from about 15 gai/ha to about 30 gai/ha and the compound of formula (I) of salt or ester thereof is applied at a rate from about 5 gae/ha to about 10 gae/ha. In one embodiment, the methods utilize the benzyl ester of the compound of formula (I) and clodinafop-propargyl are used to control LOLMU, KCHSC, PHAMI, APESV and ALOMY.

In certain embodiments of the compositions and methods described herein, the compound of formula (I) or salt or ester thereof is used in combination with cyhalofop-R-butyl or carboxylic acid, carboxylate salt, or ester thereof. With respect to the compositions, in some embodiments, the weight ratio of the compound of formula (I) or salt or ester thereof to cyhalofop-R-butyl carboxylic acid, carboxylate salt, or ester thereof is within the range of from about 1:155 to about 6:1. In certain embodiments, the weight ratio of the compound of formula (I) or salt or ester thereof to cyhalofop-R-butyl or carboxylic acid, carboxylate salt, or ester thereof is within the range of from 1:32 to about 1:4. In certain embodiments, the weight ratio of the compound of formula (I) or salt or ester thereof to cyhalofop-R-butyl or carboxylic acid, carboxylate salt, or ester thereof is within the range of from about 1:42 to about 10:1. In certain embodiments, the weight ratio of the compound of formula (I) or salt or ester thereof to cyhalofop-R-butyl or carboxylic acid, carboxylate salt, or ester thereof is within the range of from about 1:21 to about 5:1. In certain embodiments, the compositions provided herein comprise the compound of formula (I) or its benzyl ester and cyhalofop-R-butyl. In one embodiment, the composition comprises the compound of formula (I) and cyhalofop-R-butyl, wherein the weight ratio of the compound of formula (I) to cyhalofop-R-butyl is about 1:20.6 to about 1:2.5. In one embodiment, the composition comprises the benzyl ester of the compound of formula (I) and cyhalofop-R-butyl, wherein the weight ratio of the benzyl ester of the compound of formula (I) to cyhalofop-R-butyl is about 1:23 to about 5:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 grams active ingredient per hectare (gai/ha) to about 610 gai/ha based on the total amount of active ingredients in the composition. In certain embodiments, the composition is applied at an application rate of from about 99 grams active ingredient per hectare (gai/ha) to about 320 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and cyhalofop-R-butyl or carboxylic acid, carboxylate salt, or ester thereof, e.g., sequentially or simultaneously. In some embodiments, the cyhalofop-R-butyl or salt or ester thereof is applied at a rate from about 50 gai/ha to about 310 gai/ha and the compound of formula (I) of salt or ester thereof is applied at a rate from about 2 gae/ha to about 300 gae/ha. In some embodiments, the cyhalofop-R-butyl or carboxylic acid, carboxylate salt, or ester thereof is applied at a rate from about 45 gai/ha to about 600 gai/ha and the compound of formula (I) of salt or ester thereof is applied at a rate from about 4 g acid equivalent per hectare (gae/ha) to about 85 gae/ha. In some embodiments, the cyhalofop-R-butyl or carboxylic acid, carboxylate salt, or ester thereof is applied at a rate from about 90 gai/ha to about 300 gai/ha and the compound of formula (I) of salt or ester thereof is applied at a rate from about 8 g acid equivalent per hectare (gae/ha) to about 42 gae/ha. In certain embodiments, the methods utilize the compound of formula (I), or its benzyl ester and cyhalofop-R-butyl. In one embodiment, the methods utilize the compound of formula (I) and cyhalofop-R-butyl, wherein the compound of formula (I) is applied at a rate of from about 8.75 g acid equivalent per hectare (gae/ha) to about 42.4 gae/ha, and cyhalofop-R-butyl is applied at a rate of about 90 gai/ha to about 280 gai/ha. In one embodiment, the methods utilize the benzyl ester of the compound of formula (I) and cyhalofop-R-butyl, wherein the benzyl ester of the compound of formula (I) is applied at a rate of from about 8.75 g acid equivalent per hectare (gae/ha) to about 35 gae/ha, and cyhalofop-R-butyl is applied at a rate of about 90 gai/ha to about 300 gai/ha. In certain embodiments, the methods and compositions utilizing the compound of formula (I) or salt or ester thereof in combination with cyhalofop-R-butyl or carboxylic acid, carboxylate salt, or ester thereof are used to control ISCRU, IPOHE, ECHOR, SCPSU, LEFCH, SCPMA, CYPIR, FIMMI, SEBEX, CYPDI, ECHCG, ECHSS, or SCPMU.

In certain embodiments of the compositions and methods described herein, the compound of formula (I) or salt or ester thereof is used in combination with diclofop-methyl or carboxylic acid, carboxylate salt, or ester thereof. With regard to the compositions, in some embodiments, the weight ratio of the compound of formula (I) or salt or ester thereof to diclofop-methyl or carboxylic acid, carboxylate salt, or ester thereof is within the range of from about 1:560 to about 5:1. In certain embodiments, the weight ratio of the compound of formula (I) or salt or ester thereof to diclofop-methyl or carboxylic acid, carboxylate salt, or ester thereof is within the range of from 1:255 to about 1:1. In certain embodiments, the weight ratio of the compound of formula (I) or salt or ester thereof to diclofop-methyl or carboxylic acid, carboxylate salt, or ester thereof is within the range of from 1:140 to about 1:9. In certain embodiments, the compositions provided herein comprise the compound of formula (I) or its benzyl or n-butyl ester and diclofop-methyl. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 72 grams active ingredient per hectare (gai/ha) to about 1,420 gai/ha based on the total amount of active ingredients in the composition. In certain embodiments, the composition is applied at an application rate of from about 73 grams active ingredient per hectare (gai/ha) to about 610 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and diclofop-methyl or salt or ester thereof, e.g., sequentially or simultaneously. In some embodiments, the diclofop-methyl or salt or ester thereof is applied at a rate from about 70 gai/ha to about 1,120 gai/ha and the compound of formula (I) of salt or ester thereof is applied at a rate from about 2 gae/ha to about 300 gae/ha. In certain embodiments, the methods utilize the compound of formula (I), or its benzyl or n-butyl ester and diclofop-methyl are used to control APESV, CYPIR, KCHSC and PHAMI.

In certain embodiments of the compositions and methods described herein, the compound of formula (I) or salt or ester thereof is used in combination with fenoxaprop-P-ethyl or carboxylic acid or carboxylate salt thereof or other ester, and fenoxaprop-P-ethyl can be applied alone or in combination with the safeners isoxadifen-ethyl or mefenpyr-diethyl. With regard to the compositions, in some embodiments, the weight ratio of the compound of formula (I) or salt or ester thereof to fenoxaprop-P-ethyl or carboxylic acid or carboxylate salt thereof or other ester is within the range of from about 1:170 to about 30:1. In certain embodiments, the weight ratio of the compound of formula (I) or salt or ester thereof to fenoxaprop-P-ethyl or carboxylic acid or carboxylate salt thereof or other ester is within the range of from 1:16 to about 1.5:1. In certain embodiments, the weight ratio of the compound of formula (I) or salt or ester thereof to fenoxaprop-P-ethyl or carboxylic acid or carboxylate salt thereof or other ester is within the range of from 1:16 to about 3:1. In certain embodiments, the weight ratio of the compound of formula (I) or salt or ester thereof to fenoxaprop-P-ethyl or carboxylic acid or carboxylate salt thereof or other ester is within the range of from about 1:32 to about 4:1. In certain embodiments, the weight ratio of the compound of formula (I) or salt or ester thereof to fenoxaprop-P-ethyl or carboxylic acid or carboxylate salt thereof or other ester is within the range of from about 1:16 to about 2:1. In certain embodiments, the compositions provided herein comprise the compound of formula (I) or its benzyl ester and fenoxaprop-P-ethyl. In one embodiment, the composition comprises the compound of formula (I) and fenoxaprop-P-ethyl, wherein the weight ratio of the compound of formula (I) to fenoxaprop-P-ethyl is about 1:14 to about 2:1. In one embodiment, the composition comprises the benzyl ester of the compound of formula (I) and fenoxaprop-P-ethyl, wherein the weight ratio of the benzyl ester of the compound of formula (I) to fenoxaprop-P-ethyl is about 1:16 to about 1:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 13 grams active ingredient per hectare (gai/ha) to about 440 gai/ha based on the total amount of active ingredients in the composition. In certain embodiments, the composition is applied at an application rate of from about 15 grams active ingredient per hectare (gai/ha) to about 90 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and fenoxaprop-P-ethyl or salt or ester thereof, e.g., sequentially or simultaneously. In some embodiments, the fenoxaprop-P-ethyl or carboxylic acid or carboxylate salt thereof or other ester is applied at a rate from about 11 gai/ha to about 140 gai/ha and the compound of formula (I) of salt or ester thereof is applied at a rate from about 2 gae/ha to about 300 gae/ha. In some embodiments, the fenoxaprop-P-ethyl or carboxylic acid or carboxylate salt thereof or other ester is applied at a rate from about 5 gai/ha to about 300 gai/ha and the compound of formula (I) of salt or ester thereof is applied at a rate from about 2 g acid equivalent per hectare (gae/ha) to about 90 gae/ha. In some embodiments, the fenoxaprop-P-ethyl or carboxylic acid or carboxylate salt thereof or other ester is applied at a rate from about 11.5 gai/ha to about 140 gai/ha and the compound of formula (I) of salt or ester thereof is applied at a rate from about 4.38 g acid equivalent per hectare (gae/ha) to about 42.4 gae/ha. In certain embodiments, the methods utilize the compound of formula (I), or its benzyl ester and fenoxaprop-P-ethyl. In one embodiment, the methods utilize the compound of formula (I) and fenoxaprop-P-ethyl, wherein the compound of formula (I) is applied at a rate of from about 4.38 g acid equivalent per hectare (gae/ha) to about 42.4 gae/ha, and fenoxaprop-P-ethyl is applied at a rate of about 11.5 gai/ha to about 140 gai/ha. In one embodiment, the methods utilize the benzyl ester of the compound of formula (I) and fenoxaprop-P-ethyl, wherein the benzyl ester of the compound of formula (I) is applied at a rate of from about 4.38 g acid equivalent per hectare (gae/ha) to about 35 gae/ha, and fenoxaprop-P-ethyl is applied at a rate of about 17.5 gai/ha to about 70 gai/ha. In certain embodiments, the methods and compositions utilizing the compound of formula (I) or salt or ester thereof in combination with fenoxaprop-P-ethyl or carboxylic acid or carboxylate salt thereof or other ester are used to control CYPIR, ECHOR, FIMMI, SCPJU, CYPES, KCHSC, PHAMI and APESV.

In certain embodiments of the compositions and methods described herein, the compound of formula (I) or salt or ester thereof is used in combination with fluazifop-P-butyl or carboxylic acid or carboxylate salt thereof or other ester. With regard to the compositions, in some embodiments, the weight ratio of the compound of formula (I) or salt or ester thereof to fluazifop-P-butyl or carboxylic acid or carboxylate salt thereof or other ester is within the range of from about 1:210 to about 3:1. In certain embodiments, the weight ratio of the compound of formula (I) or salt or ester thereof to fluazifop-P-butyl or carboxylic acid or carboxylate salt thereof or other ester is within the range of from 1:41 to about 2.5:1. In certain embodiments, the weight ratio of the compound of formula (I) or salt or ester thereof to fluazifop-P-butyl or carboxylic acid or carboxylate salt thereof or other ester is within the range of from 1:41 to about 1:1. In certain embodiments, the weight ratio of the compound of formula (I) or salt or ester thereof to fluazifop-P-butyl or salt or ester thereof is within the range of from about 1:80 to about 1:1. In certain embodiments, the weight ratio of the compound of formula (I) or salt or ester thereof to fluazifop-P-butyl or salt or ester thereof is within the range of from about 1:36 to about 1:2.5. In certain embodiments, the compositions provided herein comprise the compound of formula (I) or its benzyl ester and fluazifop-P-butyl. In one embodiment, the composition comprises the compound of formula (I) and fluazifop-P-butyl, wherein the weight ratio of the compound of formula (I) to fluazifop-P-butyl is about 1:36 to about 1:2.5. In one embodiment, the composition comprises the benzyl ester of the compound of formula (I) and fluazifop-P-butyl, wherein the weight ratio of the benzyl ester of the compound of formula (I) to fluazifop-P-butyl is about 1:36 to about 1:5.1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 47 grams active ingredient per hectare (gai/ha) to about 720 gai/ha based on the total amount of active ingredients in the composition. In certain embodiments, the composition is applied at an application rate of from about 50 grams active ingredient per hectare (gai/ha) to about 200 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and fluazifop-P-butyl or salt or ester thereof, e.g., sequentially or simultaneously. In some embodiments, the fluazifop-P-butyl or carboxylic acid or carboxylate salt thereof or other ester is applied at a rate from about 45 gae/ha to about 420 gae/ha and the compound of formula (I) of salt or ester thereof is applied at a rate from about 2 gae/ha to about 300 gae/ha. In some embodiments, the fluazifop-P-butyl or carboxylic acid or carboxylate salt thereof or other ester is applied at a rate from about 20 gai/ha to about 400 gai/ha and the compound of formula (I) of salt or ester thereof is applied at a rate from about 2 g acid equivalent per hectare (gae/ha) to about 70 gae/ha. In some embodiments, the fluazifop-P-butyl or carboxylic acid or carboxylate salt thereof or other ester is applied at a rate from about 45 gai/ha to about 180 gai/ha and the compound of formula (I) of salt or ester thereof is applied at a rate from about 4.38 g acid equivalent per hectare (gae/ha) to about 35 gae/ha. In certain embodiments, the methods utilize the compound of formula (I), or its benzyl ester and fluazifop-P-butyl. In one embodiment, the methods utilize the compound of formula (I) and fluazifop-P-butyl, wherein the compound of formula (I) is applied at a rate of from about 4.38 g acid equivalent per hectare (gae/ha) to about 35 gae/ha, and fluazifop-P-butyl is applied at a rate of about 45 gai/ha to about 180 gai/ha. In one embodiment, the methods utilize the benzyl ester of the compound of formula (I) and fluazifop-P-butyl, wherein the benzyl ester of the compound of formula (I) is applied at a rate of from about 4.38 g acid equivalent per hectare (gae/ha) to about 8.75 gae/ha, and fluazifop-P-butyl is applied at a rate of about 45 gai/ha to about 180 gai/ha. In certain embodiments, the methods and compositions utilizing the compound of formula (I) or salt or ester thereof in combination with fluazifop-P-butyl or carboxylic acid or carboxylate salt thereof or other ester are used to control IPOHE, ECHOR, or CYPRO.

In certain embodiments of the compositions and methods described herein, the compound of formula (I) or salt or ester thereof is used in combination with haloxyfop-R-methyl or carboxylic acid or carboxylate salt thereof or other ester. With regard to the compositions, in some embodiments, the weight ratio of the compound of formula (I) or salt or ester thereof to haloxyfop-R-methyl or carboxylic acid or carboxylate salt thereof or other ester is within the range of from about 1:45 to about 10:1. In certain embodiments, the weight ratio of the compound of formula (I) or salt or ester thereof to haloxyfop-R-methyl or carboxylic acid or carboxylate salt thereof or other ester is within the range of from 1:6 to about 2.5:1. In certain embodiments, the weight ratio of the compound of formula (I) or salt or ester thereof to haloxyfop-R-methyl or carboxylic acid or carboxylate salt thereof or other ester is within the range of from about 1:15 to about 6:1. In certain embodiments, the weight ratio of the compound of formula (I) or salt or ester thereof to haloxyfop-R-methyl or carboxylic acid or carboxylate salt thereof or other ester is within the range of from about 1:7 to about 2.6:1. In certain embodiments, the compositions provided herein comprise the compound of formula (I) or its benzyl ester and haloxyfop-R-methyl. In one embodiment, the composition comprises the compound of formula (I) and haloxyfop-R-methyl, wherein the weight ratio of the compound of formula (I) to haloxyfop-R-methyl is about 1:6.2 to about 2.6:1. In one embodiment, the composition comprises the benzyl ester of the compound of formula (I) and haloxyfop-R-methyl, wherein the weight ratio of the benzyl ester of the compound of formula (I) to haloxyfop-R-methyl is about 1:7 to about 1.3:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 32 grams active ingredient per hectare (gai/ha) to about 420 gai/ha based on the total amount of active ingredients in the composition. In certain embodiments, the composition is applied at an application rate of from about 10 grams active ingredient per hectare (gai/ha) to about 60 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and haloxyfop-R-methyl or carboxylic acid or carboxylate salt thereof or other ester, e.g., sequentially or simultaneously. In some embodiments, the haloxyfop-R-methyl or carboxylic acid or carboxylate salt thereof or other ester is applied at a rate from about 6.75 gae/ha to about 120 gae/ha and the compound of formula (I) of salt or ester thereof is applied at a rate from about 2 gae/ha to about 300 gae/ha. In some embodiments, the haloxyfop-R-methyl or carboxylic acid or carboxylate salt thereof or other ester is applied at a rate from about 3 gai/ha to about 140 gai/ha and the compound of formula (I) of salt or ester thereof is applied at a rate from about 2 g acid equivalent per hectare (gae/ha) to about 45 gae/ha. In some embodiments, the haloxyfop-R-methyl or carboxylic acid or carboxylate salt thereof or other ester is applied at a rate from about 6.75 gai/ha to about 70 gai/ha and the compound of formula (I) of salt or ester thereof is applied at a rate from about 4.38 g acid equivalent per hectare (gae/ha) to about 17.5 gae/ha. In certain embodiments, the methods utilize the compound of formula (I), or its benzyl or n-butyl ester and haloxyfop-R-methyl. In one embodiment, the methods utilize the compound of formula (I) and haloxyfop-R-methyl, wherein the compound of formula (I) is applied at a rate of from about 4.38 g acid equivalent per hectare (gae/ha) to about 35 gae/ha, and haloxyfop-R-methyl is applied at a rate of about 6.75 gai/ha to about 70 gai/ha. In one embodiment, the methods utilize the benzyl ester of the compound of formula (I) and haloxyfop-R-methyl, wherein the benzyl ester of the compound of formula (I) is applied at a rate of from about 4.38 g acid equivalent per hectare (gae/ha) to about 17.5 gae/ha, and haloxyfop-R-methyl is applied at a rate of about 6.75 gai/ha to about 27 gai/ha. In certain embodiments, the methods and compositions utilizing the compound of formula (I) or salt or ester thereof in combination with haloxyfop-R-methyl or carboxylic acid or carboxylate salt thereof or other ester are used to control ECHCO, IPOHE, SCPJU, BRAPP, or CYPRO.

In certain embodiments of the compositions and methods described herein, the compound of formula (I) or salt or ester thereof is used in combination with metamifop or salt or ester thereof. With regard to the compositions, in some embodiments, the weight ratio of the compound of formula (I) or salt or ester thereof to metamifop or salt or ester thereof is within the range of from about 1:150 to about 6:1. In certain embodiments, the weight ratio of the compound of formula (I) or salt or ester thereof to metamifop or salt or ester thereof is within the range of from 1:34 to about 10:1. In certain embodiments, the weight ratio of the compound of formula (I) or salt or ester thereof to metamifop or salt or ester thereof is within the range of from 1:34 to about 1:2. In certain embodiments, the weight ratio of the compound of formula (I) or salt or ester thereof to metamifop or salt or ester thereof is within the range of from about 1:60 to about 1:1. In certain embodiments, the weight ratio of the compound of formula (I) or salt or ester thereof to metamifop or salt or ester thereof is within the range of from about 1:30 to about 1:2.1. In certain embodiments, the compositions provided herein comprise the compound of formula (I) or its benzyl ester and metamifop. In one embodiment, the composition comprises the compound of formula (I) and metamifop, wherein the weight ratio of the compound of formula (I) to metamifop is about 1:30 to about 1:2.1. In one embodiment, the composition comprises the benzyl ester of the compound of formula (I) and metamifop, wherein the weight ratio of the benzyl ester of the compound of formula (I) to metamifop is about 1:30 to about 1:15. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 grams active ingredient per hectare (gai/ha) to about 600 gai/ha based on the total amount of active ingredients in the composition. In certain embodiments, the composition is applied at an application rate of from about 40 grams active ingredient per hectare (gai/ha) to about 170 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and metamifop or salt or ester thereof, e.g., sequentially or simultaneously. In some embodiments, the metamifop or salt or ester thereof is applied at a rate from about 50 gai/ha to about 300 gai/ha and the compound of formula (I) of salt or ester thereof is applied at a rate from about 2 gae/ha to about 300 gae/ha. In some embodiments, the metamifop or salt or ester thereof is applied at a rate from about 30 gai/ha to about 300 gai/ha and the compound of formula (I) of salt or ester thereof is applied at a rate from about 2 g acid equivalent per hectare (gae/ha) to about 70 gae/ha. In some embodiments, the metamifop or salt or ester thereof is applied at a rate from about 75 gai/ha to about 150 gai/ha and the compound of formula (I) of salt or ester thereof is applied at a rate from about 4.38 g acid equivalent per hectare (gae/ha) to about 35 gae/ha. In certain embodiments, the methods utilize the compound of formula (I), or its benzyl ester and metamifop. In one embodiment, the methods utilize the compound of formula (I) and metamifop, wherein the compound of formula (I) is applied at a rate of from about 4.38 g acid equivalent per hectare (gae/ha) to about 35 gae/ha, and metamifop is applied at a rate of about 75 gai/ha to about 150 gai/ha. In one embodiment, the methods utilize the benzyl ester of the compound of formula (I) and metamifop, wherein the benzyl ester of the compound of formula (I) is applied at a rate of about 4.38 g acid equivalent per hectare (gae/ha), and metamifop is applied at a rate of about 75 gai/ha to about 150 gai/ha. In certain embodiments, the methods and compositions utilizing the compound of formula (I) or salt or ester thereof in combination with metamifop or salt or ester thereof are used to control IPOHE, ECHCG, ECHOR, IPOHE, FIMMI, SCPMA, or SCPJU.

In certain embodiments of the compositions and methods described herein, the compound of formula (I) or salt or ester thereof is used in combination with pinoxaden or salt or ester thereof. With regard to the compositions, in some embodiments, the weight ratio of the compound of formula (I) or salt or ester thereof to pinoxaden or salt or ester thereof is within the range of from about 1:30 to about 150:1. In certain embodiments, the weight ratio of the compound of formula (I) or salt or ester thereof to pinoxaden or salt or ester thereof is within the range of from 1:27 to about 25:1. In certain embodiments, the weight ratio of the compound of formula (I) or salt or ester thereof to pinoxaden or salt or ester thereof is within the range of from 1:12 to about 2:1. In certain embodiments, the compositions comprise the compound of formula (I) or its benzyl or n-butyl ester and pinoxaden. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (gai/ha) to about 360 gai/ha based on the total amount of active ingredients in the composition. In certain embodiments, the composition is applied at an application rate of from about 8 grams active ingredient per hectare (gai/ha) to about 110 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pinoxaden or salt thereof, e.g., sequentially or simultaneously. In some embodiments, the pinoxaden or salt or ester thereof is applied at a rate from about 2 gai/ha to about 60 gai/ha and the compound of formula (I) of salt or ester thereof is applied at a rate from about 2 gae/ha to about 300 gae/ha. In some embodiments, the pinoxaden or salt or ester thereof is applied at a rate from about 15 gai/ha to about 60 gai/ha and the compound of formula (I) of salt or ester thereof is applied at a rate from about 5 gae/ha to about 32 gae/ha. In certain embodiments, the methods utilize the compound of formula (I) or its benzyl or n-butyl ester and pinoxaden for the control of ECHCO, IPOHE, KCHSC, PHAMI and SCPJU.

In certain embodiments of the compositions and methods described herein, the compound of formula (I) or salt or ester thereof is used in combination with profoxydim or salt or ester thereof. With regard to the compositions, in some embodiments, the weight ratio of the compound of formula (I) or salt or ester thereof to profoxydim or salt or ester thereof is within the range of from about 1:70 to about 29:1. In certain embodiments, the weight ratio of the compound of formula (I) or salt or ester thereof to profoxydim or salt or ester thereof is within the range of from 1:8 to about 2:1. In certain embodiments, the weight ratio of the compound of formula (I) or salt or ester thereof to profoxydim or salt or ester thereof is within the range of from about 1:10 to about 3:1. In certain embodiments, the weight ratio of the compound of formula (I) or salt or ester thereof to profoxydim or salt or ester thereof is within the range of from about 1:23 to about 3:1. In certain embodiments, the weight ratio of the compound of formula (I) or salt or ester thereof to profoxydim or salt or ester thereof is within the range of from about 1:5 to about 1.4:1. In certain embodiments, the compositions provided herein comprise the compound of formula (I) or its benzyl ester and profoxydim. In one embodiment, the composition comprises the compound of formula (I) and profoxydim, wherein the weight ratio of the compound of formula (I) to profoxydim is about 1:3. In one embodiment, the composition comprises the benzyl ester of the compound of formula (I) and profoxydim, wherein the weight ratio of the benzyl ester of the compound of formula (I) to profoxydim is about 1:5 to about 1.4:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 15 grams active ingredient per hectare (gai/ha) to about 500 gai/ha based on the total amount of active ingredients in the composition. In certain embodiments, the composition is applied at an application rate of from about 16 grams active ingredient per hectare (gai/ha) to about 50 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and profoxydim or salt or ester thereof, e.g., sequentially or simultaneously. In some embodiments, the profoxydim or salt or ester thereof is applied at a rate from about 12 gai/ha to about 200 gai/ha and the compound of formula (I) of salt or ester thereof is applied at a rate from about 2 gae/ha to about 300 gae/ha. In some embodiments, the profoxydim or salt or ester thereof is applied at a rate from about 4 gai/ha to about 140 gai/ha and the compound of formula (I) of salt or ester thereof is applied at a rate from about 2 g acid equivalent per hectare (gae/ha) to about 45 gae/ha. In some embodiments, the profoxydim or salt or ester thereof is applied at a rate from about 12.5 gai/ha to about 25 gai/ha and the compound of formula (I) of salt or ester thereof is applied at a rate from about 4.38 g acid equivalent per hectare (gae/ha) to about 17.5 gae/ha. In certain embodiments, the methods utilize the compound of formula (I), or its benzyl or n-butyl ester and profoxydim. In one embodiment, the methods utilize the compound of formula (I) and profoxydim, wherein the compound of formula (I) is applied at a rate of about 4.38 g acid equivalent per hectare (gae/ha), and profoxydim is applied at a rate of about 12.5 gai/ha. In one embodiment, the methods utilize the benzyl ester of the compound of formula (I) and profoxydim, wherein the benzyl ester of the compound of formula (I) is applied at a rate of from about 4.38 g acid equivalent per hectare (gae/ha) to about 17.5 gae/ha, and profoxydim is applied at a rate of about 12.5 gai/ha to about 25 gai/ha. In certain embodiments, the methods and compositions utilizing the compound of formula (I) or salt or ester thereof in combination with profoxydim or salt or ester thereof are used to control ECHCO, ECHCO, SCPJU or LEFCH.

In certain embodiments of the compositions and methods described herein, the compound of formula (I) or salt or ester thereof is used in combination with quizalofop-P-ethyl or carboxylic acid or carboxylate salt thereof or other ester. With regard to the compositions, in some embodiments, the weight ratio of the compound of formula (I) or salt or ester thereof to quizalofop-P-ethyl or carboxylic acid or carboxylate salt thereof or other ester is within the range of from about 1:100 to about 12:1. In certain embodiments, the weight ratio of the compound of formula (I) or salt or ester thereof to quizalofop-P-ethyl or carboxylic acid or carboxylate salt thereof or other ester is within the range of from 1:8 to about 19:1. In certain embodiments, the weight ratio of the compound of formula (I) or salt or ester thereof to quizalofop-P-ethyl or carboxylic acid or carboxylate salt thereof or other ester is within the range of from 1:6 to about 1:1. In certain embodiments, the weight ratio of the compound of formula (I) or salt or ester thereof to quizalofop-P-ethyl or carboxylic acid or carboxylate salt thereof or other ester is within the range of from about 1:12 to about 10:1. In certain embodiments, the weight ratio of the compound of formula (I) or salt or ester thereof to quizalofop-P-ethyl or carboxylic acid or carboxylate salt thereof or other ester is within the range of from about 1:6 to about 5:1. In certain embodiments, the compositions provided herein comprise the compound of formula (I) or its benzyl ester and quizalofop-P-ethyl. In one embodiment, the composition comprises the compound of formula (I) and quizalofop-P-ethyl, wherein the weight ratio of the compound of formula (I) to quizalofop-P-ethyl is about 1:6 to about 5:1. In one embodiment, the composition comprises the benzyl ester of the compound of formula (I) and quizalofop-P-ethyl, wherein the weight ratio of the benzyl ester of the compound of formula (I) to quizalofop-P-ethyl is about 1:6 to about 5:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 6 grams active ingredient per hectare (gai/ha) to about 400 gai/ha based on the total amount of active ingredients in the composition. In certain embodiments, the composition is applied at an application rate of from about 8 grams active ingredient per hectare (gai/ha) to about 50 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and quizalofop-P-ethyl or carboxylic acid or carboxylate salt thereof or other ester, e.g., sequentially or simultaneously. In some embodiments, the quizalofop-P-ethyl or carboxylic acid or carboxylate salt thereof or other ester is applied at a rate from about 4 gai/ha to about 100 gae/ha and the compound of formula (I) of salt or ester thereof is applied at a rate from about 2 gae/ha to about 300 gae/ha. In some embodiments, the quizalofop-P- or carboxylic acid or carboxylate salt thereof or other ester is applied at a rate from about 2 gai/ha to about 60 gai/ha and the compound of formula (I) of salt or ester thereof is applied at a rate from about 2 g acid equivalent per hectare (gae/ha) to about 70 gae/ha. In some embodiments, the quizalofop-P-ethyl or carboxylic acid or carboxylate salt thereof or other ester is applied at a rate from about 3.56 gai/ha to about 30 gai/ha and the compound of formula (I) of salt or ester thereof is applied at a rate from about 3.75 g acid equivalent per hectare (gae/ha) to about 35 gae/ha. In certain embodiments, the methods utilize the compound of formula (I), or its benzyl ester and quizalofop-P-ethyl. In one embodiment, the methods utilize the compound of formula (I) and quizalofop-P-ethyl, wherein the compound of formula (I) is applied at a rate of from about 3.75 g acid equivalent per hectare (gae/ha) to about 35 gae/ha, and quizalofop-P-ethyl is applied at a rate of about 3.56 gai/ha to about 30 gai/ha. In one embodiment, the methods utilize the benzyl ester of the compound of formula (I) and quizalofop-P-ethyl, wherein the benzyl ester of the compound of formula (I) is applied at a rate of from about 3.75 g acid equivalent per hectare (gae/ha) to about 17.5 gae/ha, and quizalofop-P-ethyl is applied at a rate of about 3.56 gai/ha to about 30 gai/ha. In certain embodiments, the methods and compositions utilizing the compound of formula (I) or salt or ester thereof in combination with quizalofop-P-ethyl or carboxylic acid or carboxylate salt thereof or other ester are used to control IPOHE, ECHOR, CYPRO, ECHCG, AVEFA, LOLMU.

In certain embodiments of the compositions and methods described herein, the compound of formula (I) or salt or ester thereof is used in combination with sethoxydim or salt or ester thereof. With regard to the compositions, in some embodiments, the weight ratio of the compound of formula (I) or salt or ester thereof to sethoxydim or salt or ester thereof is within the range of from about 1:70 to about 29:1. In certain embodiments, the weight ratio of the compound of formula (I) or salt or ester thereof to sethoxydim or salt or ester thereof is within the range of from 1:8 to about 2:1. I In certain embodiments, the weight ratio of the compound of formula (I) or salt or ester thereof to sethoxydim or salt or ester thereof is within the range of from about 1:61 to about 1:2. In certain embodiments, the weight ratio of the compound of formula (I) or salt or ester thereof to sethoxydim or salt or ester thereof is within the range of from about 1:120 to about 1:3. In certain embodiments, the weight ratio of the compound of formula (I) or salt or ester thereof to sethoxydim or salt or ester thereof is within the range of from about 1:54 to about 1:7.7. In certain embodiments, the compositions provided herein comprise the compound of formula (I) or its benzyl ester and sethoxydim. In one embodiment, the composition comprises the compound of formula (I) and sethoxydim, wherein the weight ratio of the compound of formula (I) to sethoxydim is about 1:54 to about 1:7.7. In one embodiment, the composition comprises the benzyl ester of the compound of formula (I) and sethoxydim, wherein the weight ratio of the benzyl ester of the compound of formula (I) to sethoxydim is about 1:27 to about 1:15.4. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 55 grams active ingredient per hectare (gai/ha) to about 825 gai/ha based on the total amount of active ingredients in the composition. In certain embodiments, the composition is applied at an application rate of from about 55 grams active ingredient per hectare (gai/ha) to about 300 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and sethoxydim or salt or ester thereof, e.g., sequentially or simultaneously. In some embodiments, the sethoxydim or salt or ester thereof is applied at a rate from about 50 gai/ha to about 525 gai/ha and the compound of formula (I) of salt or ester thereof is applied at a rate from about 2 gae/ha to about 300 gae/ha. In some embodiments, the sethoxydim or salt or ester thereof is applied at a rate from about 30 gai/ha to about 600 gai/ha and the compound of formula (I) of salt or ester thereof is applied at a rate from about 2 g acid equivalent per hectare (gae/ha) to about 45 gae/ha. In some embodiments, the sethoxydim or salt or ester thereof is applied at a rate from about 67.5 gai/ha to about 270 gai/ha and the compound of formula (I) of salt or ester thereof is applied at a rate from about 4.38 g acid equivalent per hectare (gae/ha) to about 17.5 gae/ha. In certain embodiments, the methods utilize the compound of formula (I), or its benzyl ester and sethoxydim. In one embodiment, the methods utilize the compound of formula (I) and sethoxydim, wherein the compound of formula (I) is applied at a rate of from about 4.38 g acid equivalent per hectare (gae/ha) to about 17.5 gae/ha, and sethoxydim is applied at a rate of about 67.5 gai/ha to about 270 gai/ha. In one embodiment, the methods utilize the benzyl ester of the compound of formula (I) and sethoxydim, wherein the benzyl ester of the compound of formula (I) is applied at a rate of from about 4.38 g acid equivalent per hectare (gae/ha) to about 8.75 gae/ha, and sethoxydim is applied at a rate of about 135 gai/ha. In certain embodiments, the methods and compositions utilizing the compound of formula (I) or salt or ester thereof in combination with sethoxydim or salt or ester thereof are used to control CYPES, CYPDI, CYPIR, SCPJU, LEFCH, FIMMI, or ECHCG.

In certain embodiments of the compositions and methods described herein, the compound of formula (I) or salt or ester thereof is used in combination with tralkoxydim or salt or ester thereof. With regard to the compositions, in some embodiments, the weight ratio of the compound of formula (I) or salt or ester thereof to tralkoxydim or salt or ester thereof is within the range of from about 1:38 to about 60:1. In certain embodiments, the weight ratio of the compound of formula (I) or salt or ester thereof to tralkoxydim or salt or ester thereof is within the range of from 1:23 to about 10:1. In certain embodiments, the weight ratio of the compound of formula (I) or salt or ester thereof to tralkoxydim or salt or ester thereof is within the range of from 1:40 to about 1:2. In certain embodiments, the compositions comprise the compound of formula (I) or its benzyl or n-butyl ester and tralkoxydim. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 7 grams active ingredient per hectare (gai/ha) to about 375 gai/ha based on the total amount of active ingredients in the composition. In certain embodiments, the composition is applied at an application rate of from about 8 grams active ingredient per hectare (gai/ha) to about 100 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and tralkoxydim or salt thereof, e.g., sequentially or simultaneously. In some embodiments, the tralkoxydim or salt or ester thereof is applied at a rate from about 5 gai/ha to about 75 gai/ha and the compound of formula (I) of salt or ester thereof is applied at a rate from about 2 gae/ha to about 300 gae/ha. In certain embodiments, the methods utilize the compound of formula (I) or its benzyl or n-butyl ester and tralkoxydim are used to control AVEFA, CYPIR, KCHSC and LOLMU.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA; 4-CPB; 4-CPP; 2,4-D; 2,4-D choline salt, 2,4-D esters and amines, 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, cliodinate, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxasulfone, fenteracol, fenthiaprop, fentrazamide, fenuron, ferrous sulfate, flamprop, flamprop-M, flazasulfuron, florasulam, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, fluoroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate salts and esters, halauxifen, halauxifen-methyl, halosafen, halosulfuron-methyl, haloxydine, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufenethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, piperophos, potassium arsenite, potassium azide, potassium cyanate, pretilachlor, primisulfuron-methyl, procyazine, prodiamine, profluazol, profluralin, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, rhodethanil, rimsulfuron, saflufenacil, S-metolachlor, sebuthylazine, secbumeton, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, SYN-523, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiocarbazil, tioclorim, topramezone, triafamone, triallate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes of action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, ethephon, pentachlorophenol, thidiazuron, tribufos, aviglycine, maleic hydrazide, gibberellins, gibberellic acid, abscisic acid, ancymidol, fosamine, glyphosine, isopyrimol, jasmonic acid, maleic hydrazide, mepiquat, 2,3,5-tri-iodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol and trinexapac.

In some embodiments, the plant growth regulators are employed in one or more crops or settings, such as rice, cereal crops, corn, maize, broadleaf crops, oilseed rape/canola, turf, pineapple, sugarcane, sunflower, pastures, grasslands, rangelands, fallowland, tree and vine orchards, plantation crops, vegetables, and non-crop (ornamentals) settings. In some embodiments, the plant growth regulator is mixed with the compound of formula (I), or mixed with the compound of formula (I) and ACCase inhibitors to cause a preferentially advantageous effect on plants.

In certain embodiments, the compositions comprise or the methods utilize (a) the compound of formula I or agriculturally acceptable salt or ester thereof; (b) an ACCase inhibitor; and (c) a third herbicide. In some embodiments, the compositions comprise or the methods utilize a compound of Formula I or agriculturally acceptable salt or ester thereof, cyhalofop-butyl, and penoxsulam. In some embodiments, the compound of formula I or agriculturally acceptable salt or ester thereof is from about 7 to about 45 weight percent of the total composition; cyhalofop-butyl is from about 48 to about 89 weight percent of the total composition, and penoxsulam is from about 4 to about 7 weight percent of the total composition. In certain embodiments, the compound of formula I or agriculturally acceptable salt or ester thereof is from about 9 to about 28 weight percent of the total composition; cyhalofop-butyl is from about 62 to about 88 weight percent of the total composition, and penoxsulam is from about 2 to about 10 weight percent of the total composition. In some embodiments, the compound of formula I or agriculturally acceptable salt or ester thereof, or salt or ester thereof, is applied at a rate from about 2 to about 300 gae/ha (grams acid equivalent/ha); cyhalofop-butyl salt or ester thereof is applied at a rate from about 25 to about 320 gai/ha (grams active ingredient/ha), and penoxsulam is applied from about 1 to about 50 gr ai/ha (grams active ingredient/ha). In a further embodiment, the compound of formula I or agriculturally acceptable salt or ester thereof, is applied at a rate from about 1 to about 32 gae/ha; cyhalofop-butyl salt or ester thereof is applied at a rate from about 25 to about 280 gai/ha, and penoxsulam is applied from about 2 to about 35 gr ai/ha. In certain embodiments, the methods and compositions utilizing the compound of formula (I) or salt or ester thereof in combination with cyhalofop-butyl and penoxsulam, or salt or ester thereof, are used to control ECHCG, CYPRO and FIMMI.

In some embodiments, the compositions comprise or the methods utilize a compound of formula I or agriculturally acceptable salt or ester thereof, cyhalofop-butyl, and bentazon-sodium. In some embodiments, the compound of formula I or agriculturally acceptable salt or ester thereof is from about 2 to about 13 weight percent of the total composition; cyhalofop-butyl is from about 14 to about 20 weight percent of the total composition, and bentazon-sodium is from about 73 to about 78 weight percent of the total composition. In certain embodiments, the compound of formula I or agriculturally acceptable salt or ester thereof is from about 1 to about 9 weight percent of the total composition; cyhalofop-butyl is from about 15 to about 18 weight percent of the total composition, and bentazon-sodium is from about 78 to about 84 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and bentazon-sodium is applied from about 1 to about 1,500 gr ai/ha. In a further embodiment, the compound of formula I or agriculturally acceptable salt or ester thereof, is applied at a rate from about 1 to about 32 gae/ha; cyhalofop-butyl salt or ester thereof is applied at a rate from about 25 to about 280 gai/ha, and bentazon-sodium is applied from about 210 to about 1,200 gr ai/ha. In certain embodiments, the methods and compositions utilizing the compound of formula (I) or salt or ester thereof in combination with cyhalofop-butyl and bentazone sodium, or salt or ester thereof, are used to control ECHCG and FIMMI.

In some embodiments, the compositions comprise or the methods utilize a compound of the formula I or agriculturally acceptable salt or ester thereof, cyhalofop-butyl, and triclopyr. In some embodiments, the compound of formula I or agriculturally acceptable salt or ester thereof is from about 2 to about 20 weight percent of the total composition; cyhalofop-butyl is from about 20 to about 22 weight percent of the total composition, and bentazon-sodium is from about 58 to about 78 weight percent of the total composition. In certain embodiments, the compound of formula I or agriculturally acceptable salt or ester thereof is from about 1 to about 11 weight percent of the total composition; cyhalofop-butyl is from about 15 to about 25 weight percent of the total composition, and triclopyr is from about 64 to about 84 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and triclopyr is applied from about 100 to about 840 gr ae/ha. In a further embodiment, the compound of formula I or agriculturally acceptable salt or ester thereof, is applied at a rate from about 1 to about 32 gae/ha; cyhalofop-butyl salt or ester thereof is applied at a rate from about 25 to about 280 gai/ha, and triclopyr is applied from about 210 to about 560 gr ae/ha. In certain embodiments, the methods and compositions utilizing the compound of formula (I) or salt or ester thereof in combination with cyhalofop-butyl and triclopyr, or salt or ester thereof, are used to control ECHCG and SCPJU.

In some embodiments, the compositions comprise or the methods utilize a compound of formula I or agriculturally acceptable salt or ester thereof, cyhalofop-butyl, and bispyribac-sodium. In some embodiments, the compound of formula I or agriculturally acceptable salt or ester thereof is from about 4 to about 44 weight percent of the total composition; cyhalofop-butyl is from about 47 to about 53 weight percent of the total composition, and bispyribac-sodium is from about 9 to about 43 weight percent of the total composition. In certain embodiments, the compound of formula I or agriculturally acceptable salt or ester thereof is from about 6 to about 28 weight percent of the total composition; cyhalofop-butyl is from about 60 to about 63 weight percent of the total composition, and bispyribac-sodium is from about 11 to about 30 weight percent of the total composition. In some embodiments, the compound of formula I, or salt or ester thereof, is applied at a rate from about 2 to about 300 gae/ha; cyhalofop-butyl is applied at a rate from about 25 to about 320 gai/ha, and bispyribac-sodium is applied from about 20 to about 90 gr ai/ha. In a further embodiment, the compound of formula I or agriculturally acceptable salt or ester thereof, is applied at a rate from about 1 to about 32 gae/ha; cyhalofop-butyl salt or ester thereof is applied at a rate from about 25 to about 280 gai/ha, and bispyribac-sodium is applied from about 25 to about 75 gr ai/ha. In certain embodiments, the methods and compositions utilizing the compound of formula (I) or salt or ester thereof in combination with cyhalofop-butyl and bispyribac-sodium, or salt or ester thereof, are used to control ECHCG and SCPJU.

In some embodiments, the compositions comprise or the methods utilize the compound of formula I, cyhalofop-butyl, and imazamox. In some embodiments, the compound of formula I or agriculturally acceptable salt or ester thereof is from about 5 to about 44 weight percent of the total composition; cyhalofop-butyl is from about 46 to about 77 weight percent of the total composition, and imazamox is from about 10 to about 18 weight percent of the total composition. In certain embodiments, the compound of formula I or agriculturally acceptable salt or ester thereof is from about 8 to about 28 weight percent of the total composition; cyhalofop-butyl is from about 58 to about 80 weight percent of the total composition, and imazamox is from about 12 to about 14 weight percent of the total composition. In some embodiments, the compound of Formula I, or salt or ester thereof, is applied at a rate from about 2 to about 300 gai/ha; cyhalofop-butyl is applied at a rate from about 25 to about 320 gai/ha, and imazamox is applied from about 6 to about 70 gr ai/ha.

In some embodiments, the compositions comprise or the methods utilize a compound of the formula I or agriculturally acceptable salt or ester thereof, cyhalofop-butyl, and benzobicyclon. In some embodiments, the compound of formula I or agriculturally acceptable salt or ester thereof is from about 3 to about 33 weight percent of the total composition; cyhalofop-butyl is from about 32 to about 35 weight percent of the total composition, and benzobicyclon is from about 33 to about 65 weight percent of the total composition. In certain embodiments, the compound of formula I or agriculturally acceptable salt or ester thereof is from about 3 to about 19 weight percent of the total composition; cyhalofop-butyl is from about 32 to about 42 weight percent of the total composition, and benzobicyclon is from about 39 to about 65 weight percent of the total composition. In some embodiments, the compound of Formula I, or salt or ester thereof, is applied at a rate from about 2 to about 300 gai/ha; cyhalofop-butyl is applied at a rate from about 25 to about 320 gai/ha, and benzobicyclon is applied from about 50 to about 300 gr ai/ha.

In a further embodiment, the compound of formula I or agriculturally acceptable salt or ester thereof, is applied at a rate from about 1 to about 32 gae/ha; cyhalofop-butyl salt or ester thereof is applied at a rate from about 25 to about 280 gai/ha, and benzobicyclon is applied from about 50 to about 300 gr ai/ha. In certain embodiments, the methods and compositions utilizing the compound of formula (I) or salt or ester thereof in combination with cyhalofop-butyl and bispyribac-sodium, or salt or ester thereof, are used to control ECHCG, ECHOR and FIMMI.

In some embodiments, the compositions comprise or the methods utilize a compound of the formula I or agriculturally acceptable salt or ester thereof, cyhalofop-butyl, and quinclorac. In some embodiments, the compound of formula I or agriculturally acceptable salt or ester thereof is from about 2 to about 25 weight percent of the total composition; cyhalofop-butyl is from about 25 to about 27 weight percent of the total composition, and quinclorac is from about 48 to about 72 weight percent of the total composition. In certain embodiments, the compound of formula I or agriculturally acceptable salt or ester thereof is from about 3 to about 14 weight percent of the total composition; cyhalofop-butyl is from about 25 to about 26 weight percent of the total composition, and quinclorac is from about 54 to about 71 weight percent of the total composition. In some embodiments, the compound of formula I, or salt or ester thereof, is applied at a rate from about 2 to about 300 gae/ha; cyhalofop-butyl is applied at a rate from about 25 to about 320 gai/ha, and Quinclorac is applied from about 70 to about 560 gr ai/ha.

In some embodiments, the compositions comprise or the methods utilize a compound of the formula I or agriculturally acceptable salt or ester thereof, cyhalofop-butyl, and glyphosate. In some embodiments, the compound of formula I or agriculturally acceptable salt or ester thereof is from about 1 to about 11 weight percent of the total composition; cyhalofop-butyl is from about 11 to about 13 weight percent of the total composition, and glyphosate is from about 78 to about 86 weight percent of the total composition. In certain embodiments the compound of formula I or agriculturally acceptable salt or ester thereof is from about 1.5 to about 5.5 weight percent of the total composition; cyhalofop-butyl is from about 15 to about 11.5 weight percent of the total composition, and glyphosate is from about 83 to about 83.5 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and glyphosate is applied from about 160 to about 2240 gr ae/ha.

In some embodiments, the compositions comprise or the methods utilize a compound of the formula I or agriculturally acceptable salt or ester thereof, cyhalofop-butyl, and glufosinate. In some embodiments, the compound of formula I or agriculturally acceptable salt or ester thereof is from about 4 to about 14 weight percent of the total composition; cyhalofop-butyl is from about 15 to about 45 weight percent of the total composition, and glufosinate is from about 51 to about 71 weight percent of the total composition. In certain embodiments, the compound of formula I or agriculturally acceptable salt or ester thereof is from about 4 to about 7 weight percent of the total composition; cyhalofop-butyl is from about 16 to about 38 weight percent of the total composition, and glufosinate is from about 58 to about 77 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and glufosinate is applied from about 28 to about 1560 gr ai/ha.

In some embodiments, the compositions comprise or the methods utilize a compound of the formula I or agriculturally acceptable salt or ester thereof, fenoxaprop, and penoxsulam. In some embodiments, the compound of formula I or agriculturally acceptable salt or ester thereof is from about 7 to about 61 weight percent of the total composition; fenoxaprop is from about 89 to about 29 weight percent of the total composition, and penoxsulam is from about 4 to about 10 weight percent of the total composition. In certain embodiments, the compound of formula I or agriculturally acceptable salt or ester thereof is from about 9 to about 44 weight percent of the total composition; fenoxaprop is from about 41 to about 88 weight percent of the total composition, and penoxsulam is from about 3 to about 15 weight percent of the total composition. In some embodiments, the compound of Formula I, or salt or ester thereof, is applied at a rate from about 2 to about 300 gae/ha; fenoxaprop is applied at a rate from about 25 to about 140 gr ae/ha, and penoxsulam is applied from about 1 to about 50 gr ai/ha.

In some embodiments, the compositions comprise or the methods utilize a compound of the formula I or agriculturally acceptable salt or ester thereof, metamifop, and penoxsulam. In some embodiments, the compound of formula I or agriculturally acceptable salt or ester thereof is from about 4 to about 46 weight percent of the total composition; metamifop is from about 46 to about 94 weight percent of the total composition, and penoxsulam is from about 2 to about 8 weight percent of the total composition. In certain embodiments, the compound of formula I or agriculturally acceptable salt or ester thereof is from about 7 to about 30 weight percent of the total composition; metamifop is from about 60 to about 90 weight percent of the total composition, and penoxsulam is from about 3 to about 10 weight percent of the total composition. In some embodiments, the compound of Formula I, or salt or ester thereof, is applied at a rate from about 2 to about 300 gae/ha; metamifop is applied at a rate from about 10 to about 300 gr ae/ha, and penoxsulam is applied from about 1 to about 50 gr ai/ha. In a further embodiment, the compound of formula I or agriculturally acceptable salt or ester thereof, is applied at a rate from about 1 to about 32 gae/ha; metamifop salt or ester thereof, is applied at a rate from about 25 to about 100 gai/ha, and penoxsulam is applied from about 5 to about 35 gr ai/ha. In certain embodiments, the methods and compositions utilizing the compound of formula (I) or salt or ester thereof in combination with metamifop and penoxsulam, or salt or ester thereof, are used to control ECHCG.

In some embodiments, the compositions comprise or the methods utilize a compound of the formula I or agriculturally acceptable salt or ester thereof, profoxydim, and penoxsulam. In some embodiments, the compound of formula I or agriculturally acceptable salt or ester thereof is from about 13 to about 55 weight percent of the total composition; profoxydim is from about 36 to about 80 weight percent of the total composition, and penoxsulam idiments, the compound of formula I or agriculturally acceptable salt or ester thereof is from about 19 to about 39 weight percent of the total composition; profoxydim is from about 50 to about 74 weight percent of the total composition, and penoxsulam is from about 3 to about 10 weight percent of the total composition. In some embodiments, the compound of Formula I, or salt or ester thereof, is applied at a rate from about 2 to about 300 gae/ha; profoxydim is applied at a rate from about 12 to about 200 gr ai/ha, and penoxsulam is applied from about 1 to about 50 gr ai/ha.

In some embodiments, the compositions comprise or the methods utilize a compound of the formula I or agriculturally acceptable salt or ester thereof, cyhalofop-butyl, and benfuresate. In some embodiments, the compound of formula I or agriculturally acceptable salt or ester thereof is from about 2 to about 32 weight percent of the total composition; cyhalofop-butyl is from about 34 to about 35 weight percent of the total composition, and benfuresate is from about 33 to about 64 weight percent of the total composition. In certain embodiments, the compound of formula I or agriculturally acceptable salt or ester thereof is from about 3 to about 19 weight percent of the total composition; cyhalofop-butyl is from about 32 to about 42 weight percent of the total composition, and benfuresate is from about 39 to about 64 weight percent of the total composition. In some embodiments, the compound of Formula I, or salt or ester thereof, is applied at a rate from about 2 to about 300 gae/ha; cyhalofop-butyl, is applied at a rate from about 25 to about 320 gai/ha, and benfuresate is applied from about 50 to 300 gr ai/ha.

In some embodiments, the compositions comprise or the methods utilize a compound of the formula I or agriculturally acceptable salt or ester thereof cyhalofop-butyl, and fentrazamide. In some embodiments, the compound of formula I or agriculturally acceptable salt or ester thereof is from about 5 to about 33 weight percent of the total composition; cyhalofop-butyl is from about 35 to about 58 weight percent of the total composition, and fentrazamide is from about 32 to about 37 weight percent of the total composition. In certain embodiments, the compound of formula I or agriculturally acceptable salt or ester thereof is from about 6 to about 19 weight percent of the total composition; cyhalofop-butyl is from about 39 to about 63 weight percent of the total composition, and fentrazamide is from about 31 to about 40 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and fentrazamide is applied from about 16 to about 300 gr ai/ha.

In some embodiments, the compositions comprise or the methods utilize a compound of the formula I or agriculturally acceptable salt or ester thereof, cyhalofop-butyl, and indanofan. In some embodiments, the compound of formula I or agriculturally acceptable salt or ester thereof is from about 4 to about 33 weight percent of the total composition; cyhalofop-butyl is from about 35 to about 48 weight percent of the total composition, and indanofan is from about 32 to about 48 weight percent of the total composition. In certain embodiments, the compound of formula I or agriculturally acceptable salt or ester thereof si from about 5 to about 19 weight percent of the total composition; cyhalofop-butyl is from about 42 to about 48 weight percent of the total composition, and indanofan is from about 39 to about 48 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and indanofan is applied from about 25 to about 300 gr ai/ha.

In some embodiments, the compositions comprise or the methods utilize a compound of the formula I or agriculturally acceptable salt or ester thereof, cyhalofop-butyl, and ipfencarbazone. In some embodiments, the compound of formula I or agriculturally acceptable salt or ester thereof is from about 1 to about 27 weight percent of the total composition; cyhalofop-butyl is from about 9 to about 28 weight percent of the total composition, and ipfencarbazone is from about 45 to about 90 weight percent of the total composition. In certain embodiments, the compound of formula I or agriculturally acceptable salt or ester thereof is from about 1 to about 15 weight percent of the total composition; cyhalofop-butyl is from about 14 to about 33 weight percent of the total composition, and ipfencarbazone is from about 52 to about 85 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and ipfencarbazone is applied from about 250 to about 500 gr ai/ha.

In some embodiments, the compositions comprise or the methods utilize a compound of the formula I or agriculturally acceptable salt or ester thereof, cyhalofop-butyl, and mefenacet. In some embodiments, the compound of formula I or agriculturally acceptable salt or ester thereof is from about 1 to about 14 weight percent of the total composition; cyhalofop-butyl is from about 9 to about 14 weight percent of the total composition, and mefenacet is from about 72 to about 90 weight percent of the total composition. In certain embodiments, Formula I is from about 2 to about 7 weight percent of the total composition; cyhalofop-butyl is from about 14 to about 16 weight percent of the total composition, and mefenacet is from about 77 to about 85 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and mefenacet is applied from about 250 to about 1600 gr ai/ha. In a further embodiment, the compound of formula I or agriculturally acceptable salt or ester thereof, is applied at a rate from about 1 to about 32 gae/ha; cyhalofop-butyl salt or ester thereof is applied at a rate from about 25 to about 280 gai/ha, and mefenacet is applied from about 75 to about 560 gr ai/ha.

In some embodiments, the compositions comprise or the methods utilize a compound of the formula I or agriculturally acceptable salt or ester thereof, cyhalofop-butyl, and oxazichlomafone. In some embodiments, the compound of formula I or agriculturally acceptable salt or ester thereof is from about 6 to about 43 weight percent of the total composition; cyhalofop-butyl is from about 42 to about 76 weight percent of the total composition, and oxazichlomafone is from about 11 to about 18 weight percent of the total composition. In certain embodiments, the compound of formula I or agriculturally acceptable salt or ester thereof is from about 7 to about 27 weight percent of the total composition; cyhalofop-butyl is from about 58 to about 77 weight percent of the total composition, and oxazichlomafone is from about 14 to about 15 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and oxazichlomafone is applied from about 6 to about 80 gr ai/ha. In some embodiments, the compositions comprise or the methods utilize a compound of the formula I or agriculturally acceptable salt or ester thereof, cyhalofop-butyl, or pretilachlor.

In some embodiments, the compound of formula I or agriculturally acceptable salt or ester thereof is from about 3 to about 22 weight percent of the total composition; cyhalofop-butyl is from about 23 to about 38 weight percent of the total composition, and pretilachlor is from about 55 to about 58 weight percent of the total composition. In certain embodiments, the compound of formula I or agriculturally acceptable salt or ester thereof is from about 3 to about 13 weight percent of the total composition; cyhalofop-butyl is from about 26 to about 32 weight percent of the total composition, and pretilachlor is from about 61 to about 65 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and pretilachlor is applied from about 38 to about 750 gr ai/ha.

In some embodiments, the compound of formula I or agriculturally acceptable salt or ester thereof, cyhalofop-butyl, and propyrisulfuron. In some embodiments, the compound of formula I or agriculturally acceptable salt or ester thereof is from about 5 to about 42 weight percent of the total composition; cyhalofop-butyl is from about 44 to about 66 weight percent of the total composition, and propyrisulfuron is from about 14 to about 29 weight percent of the total composition. In certain embodiments, the compound of formula I or agriculturally acceptable salt or ester thereof is from about 7 to about 26 weight percent of the total composition; cyhalofop-butyl is from about 56 to about 66 weight percent of the total composition, and propyrisulfuron is from about 18 to about 27 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and propyrisulfuron is applied from about 11 to about 100 gr ai/ha.

In some embodiments, the compound of formula I or agriculturally acceptable salt or ester thereof, cyhalofop-butyl, and pyraclonil. In some embodiments, the compound of formula I or agriculturally acceptable salt or ester thereof is from about 1 to about 33 weight percent of the total composition; cyhalofop-butyl is from about 12 to about 33 weight percent of the total composition, and pyraclonil is from about 33 to about 87 weight percent of the total composition. In certain embodiments, the compound of formula I or agriculturally acceptable salt or ester thereof is from about 2 to about 19 weight percent of the total composition; cyhalofop-butyl is from about 20 to about 42 weight percent of the total composition, and pyraclonil is from about 39 to about 78 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and pyraclonil is applied from about 180 to about 300 gr ai/ha.

In some embodiments, the compound of formula I or agriculturally acceptable salt or ester thereof, cyhalofop-butyl, and pyriftalid. In some embodiments, the compound of formula I or agriculturally acceptable salt or ester thereof is from about 3 to about 42 weight percent of the total composition; cyhalofop-butyl is from about 35 to about 45 weight percent of the total composition, and pyriftalid is from about 13 to about 62 weight percent of the total composition. In certain embodiments, the compound of formula I or agriculturally acceptable salt or ester thereof is from about 5 to about 27 weight percent of the total composition; cyhalofop-butyl is from about 47 to about 57 weight percent of the total composition, and pyriftalid is from about 16 to about 48 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and pyriftalid is applied from about 45 to about 90 gr ai/ha.

In some embodiments, the compound of formula I or agriculturally acceptable salt or ester thereof, cyhalofop-butyl, and pyrimisulfan. In some embodiments, the compound of formula I or agriculturally acceptable salt or ester thereof is from about 7 to about 46 weight percent of the total composition; cyhalofop-butyl is from about 48 to about 85 weight percent of the total composition, and pyrimisulfan is from about 6 to about 8 weight percent of the total composition. In certain embodiments, Formula I is from about 9 to about 29 weight percent of the total composition; cyhalofop-butyl is from about 63 to about 84 weight percent of the total composition, and pyrimisulfan is from about 7 to about 8 weight percent of the total composition. In some embodiments, the compound of Formula I, or salt or ester thereof, is applied at a rate from about 2 to about 300 gae/ha; cyhalofop-butyl is applied at a rate from about 25 to about 320 gai/ha, and pyrimisulfan is applied from about 2.5 to about 40 gr ai/ha.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, furilazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, Water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiment's about 0.5 to 90 weight percent. Such compositions are, in certain embodiments, diluted with an inert carrier, such as water, before application. The diluted compositions usually applied to weeds or the locus of weeds contain, in certain embodiments, about 0.0006 to 10.0 weight percent active ingredient and in certain embodiments contain about 0.01 to 5.0 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Results in Examples I, II, III, IV VI, and VII are greenhouse trial results.

Example I

Evaluation of Postemergence Foliar-Applied Herbicidal Mixtures for Weed Control in Direct Seeded Rice Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 square centimeters ($cm^2$). When required to ensure good germination and healthy plants, a fungicide treatment and/or other chemical or physical treatment was applied. The plants were grown for 8-22 days in a greenhouse with an approximate 14 hr photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (Compound A), each formulated as an SC (suspension concentrate), and various herbicidal components alone and in combination. Forms of compound A were applied on an acid equivalent basis.

Forms of Compound a (Compound of Formula I) Tested Include:

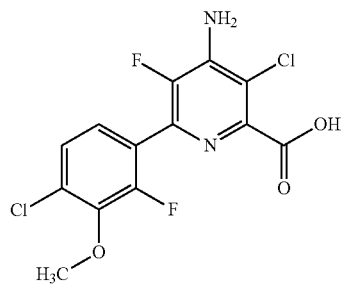

Acid

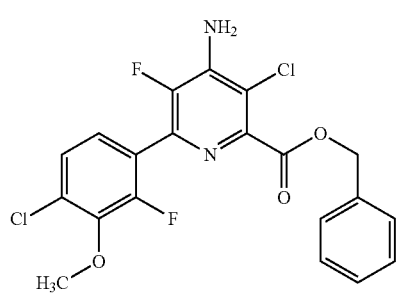

Benzyl Ester

Other herbicidal components were applied on an acid equivalent (ae) or active ingredient (ai) basis and included acetyl coA carboxylase (ACCase)-inhibiting herbicides (cyclohexanedione and aryloxyphenoxypropionate chemical classes) cyhalofop-butyl formulated as Clincher® SF (285 gr ai/L EC), diclofop-methyl formulated as Hoelon® 3EC, fenoxaprop-p-ethyl+isoxadifen-ethyl formulated as RiceStar® HT (0.58 lb/gal EC), fenoxaprop-p-ethyl+mefenpyr diethyl formulated as Puma® 1EC, metamifop formulated as Metamifop EC, haloxyfop-methyl formulated as Gallant Super®, fluazifop-p-butyl formulated as Fusilade® DX, quizalofop-p-ethyl formulated as Assure® II, profoxydim formulated as Aura® 20EC, clethodim applied as Intensity®, sethoxydim formulated as Poast®, and tralkoxydim formulated as Achieve®.

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrated to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) crop oil concentrate so that the final spray solutions contained 1.25+/−0.05% (v/v) crop oil concentrate.

For treatments comprised of technical compounds, weighed amounts can be placed individually in 25 mL glass vials and dissolved in a volume of 97:3 v/v acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials can be placed individually in 25 mL glass vials and dissolved in a volume of 97:3 v/v acetone/DMSO to obtain 12× stock solutions, and measured amounts of the formulated compounds can be placed individually in 25 mL glass vials and diluted in a volume of 1.5% (v/v) crop oil concentrate or water to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of an appropriate amount of an aqueous mixture of 1.5% (v/v) crop oil concentrate so that the final spray solutions contain 1.25% (v/v) crop oil concentrate. As required, additional water and/or 97:3 v/v acetone/DMSO can be added to individual application solutions so that the final acetone and DMSO concentrations of the application solutions being compared are 8.1% and 0.25%, respectively.

All stock solutions and applications solutions were visually inspected for compound compatibility prior to application. Spray solutions were applied to the plant material with an overhead Mandel track sprayer equipped with a 8002E nozzles calibrated to deliver 187 L/ha over an application area of 0.503 m$^2$ at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$Expected = A + B - (A \times B / 100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 1-21.

TABLE 1

Synergistic Activity of Foliar-Applied Compound A Acid and Cyhalofop-Butyl Herbicidal Compositions on Weed Control in a Rice Cropping System.

| Compound A Acid | Cyhalofop-butyl | Visual Weed Control (%) - 26 DAA ISCRU | |
|---|---|---|---|
| gae/ha | gai/ha | Obs | Exp |
| 8.75 | 0 | 37 | — |
| 17.5 | 0 | 63 | — |
| 0 | 140 | 10 | — |
| 8.75 | 140 | 63 | 43 |
| 17.5 | 140 | 82 | 67 |

| Compound A Acid | Cyhalofop-butyl | Visual Weed Control (%) - 20 DAA IPOHE | |
|---|---|---|---|
| gae/ha | gai/ha | Obs | Exp |
| 19.4 | 0 | 15 | — |
| 0 | 280 | 0 | — |
| 19.4 | 280 | 55 | 15 |

TABLE 2

Synergistic Activity of Foliar-Applied Compound A Benzyl Ester and Cyhalofop-Butyl Herbicidal Compositions on Weed Control in a Rice Cropping System.

| Compound A Benzyl Ester | Cyhalofop-butyl | Visual Weed Control (%) - 26 DAA ISCRU | |
|---|---|---|---|
| gae/ha | gai/ha | Obs | Exp |
| 8.75 | 0 | 18 | — |
| 17.5 | 0 | 33 | — |
| 0 | 140 | 10 | — |
| 8.75 | 140 | 53 | 27 |
| 17.5 | 140 | 40 | 40 |

TABLE 3

Synergistic Activity of Foliar-Applied Compound A Acid and Fenoxaprop-p-ethyl + Isoxadifen-ethyl Herbicidal Compositions on Weed Control in a Rice Cropping System.

| Compound A Acid | Fenoxaprop-p-ethyl + Isoxadifen-ethyl | Visual Weed Control (%) - 20 DAA CYPDI | |
|---|---|---|---|
| gae/ha | gai/ha* | Obs | Exp |
| 4.38 | 0 | 80 | — |
| 0 | 17.5 | 0 | — |
| 0 | 35 | 0 | — |
| 0 | 70 | 0 | — |
| 4.38 | 17.5 | 70 | 80 |
| 4.38 | 35 | 99 | 80 |
| 4.38 | 70 | 95 | 80 |

| Compound A Acid | Fenoxaprop-p-ethyl + Isoxadifen-ethyl | Visual Weed Control (%) - 20 DAA CYPES | |
|---|---|---|---|
| gae/ha | gai/ha* | Obs | Exp |
| 4.38 | 0 | 30 | — |
| 8.75 | 0 | 70 | — |
| 0 | 17.5 | 0 | — |
| 0 | 35 | 0 | — |
| 0 | 70 | 0 | — |
| 4.38 | 17.5 | 30 | 30 |
| 8.75 | 17.5 | 100 | 70 |
| 4.38 | 35 | 40 | 30 |
| 8.75 | 35 | 90 | 70 |
| 4.38 | 70 | 80 | 30 |
| 8.75 | 70 | 99 | 70 |

| Compound A Acid | Fenoxaprop-p-ethyl + Isoxadifen-ethyl | Visual Weed Control (%) - 20 DAA SCPJU | |
|---|---|---|---|
| gae/ha | gai/ha* | Obs | Exp |
| 4.38 | 0 | 60 | — |
| 0 | 17.5 | 50 | — |
| 0 | 35 | 30 | — |
| 0 | 70 | 30 | — |
| 4.38 | 17.5 | 100 | 80 |
| 4.38 | 35 | 95 | 72 |
| 4.38 | 70 | 95 | 72 |

*gai/ha refers to concentration of fenoxaprop-p-ethyl

TABLE 4

Synergistic Activity of Foliar-Applied Compound A Benzyl Ester and Fenoxaprop-p-ethyl + Isoxadifen-ethyl Herbicidal Compositions on Weed Control in a Rice Cropping System.

| Compound A Benzyl Ester | Fenoxaprop-p-ethyl + Isoxadifen-ethyl | Visual Weed Control (%) - 20 DAA CYPES | |
|---|---|---|---|
| gae/ha | gai/ha* | Obs | Exp |
| 4.38 | 0 | 70 | — |
| 8.75 | 0 | 80 | — |
| 17.5 | 0 | 95 | — |
| 0 | 17.5 | 0 | — |
| 0 | 35 | 0 | — |
| 0 | 70 | 0 | — |
| 4.38 | 17.5 | 80 | 70 |
| 8.75 | 17.5 | 95 | 80 |
| 17.5 | 17.5 | 95 | 95 |
| 4.38 | 35 | 80 | 70 |
| 8.75 | 35 | 90 | 80 |
| 17.5 | 35 | 99 | 95 |
| 4.38 | 70 | 80 | 70 |

TABLE 4-continued

Synergistic Activity of Foliar-Applied Compound A Benzyl Ester and Fenoxaprop-p-ethyl + Isoxadifen-ethyl Herbicidal Compositions on Weed Control in a Rice Cropping System.

| 8.75 | 70 | 95 | 80 |
| 17.5 | 70 | 100 | 95 |

| Compound A Benzyl Ester | Fenoxaprop-p-ethyl + Isoxadifen-ethyl | Visual Weed Control (%) - 20 DAA CYPIR | |
|---|---|---|---|
| gae/ha | gai/ha* | Obs | Exp |
| 4.38 | 0 | 15 | — |
| 0 | 17.5 | 0 | — |
| 0 | 35 | 0 | — |
| 0 | 70 | 0 | — |
| 4.38 | 17.5 | 70 | 15 |
| 4.38 | 35 | 60 | 15 |
| 4.38 | 70 | 70 | 15 |

*gai/ha refers to concentration of fenoxaprop-p-ethyl

TABLE 5

Synergistic Activity of Foliar-Applied Compound A Benzyl Ester and Fenoxaprop-p-ethyl + Mefenpyr-diethyl Herbicidal Compositions on Control of Weeds Common to Rice Cropping Systems.

| Compound A Benzyl Ester | Fenoxaprop-p-ethyl + Mefenpyr-diethyl | Visual Weed Control (%) - 20 DAA CYPIR | |
|---|---|---|---|
| gae/ha | gai/ha* | Obs | Exp |
| 8.75 | 0 | 35 | — |
| 0 | 11.5 | 0 | — |
| 0 | 23 | 0 | — |
| 0 | 46 | 0 | — |
| 8.75 | 11.5 | 80 | 35 |
| 8.75 | 23 | 85 | 35 |
| 8.75 | 46 | 50 | 35 |

*gai/ha refers to concentration of fenoxaprop-p-ethyl

TABLE 6

Synergistic Activity of Foliar-Applied Compound A Acid and Haloxyfop-methyl Herbicidal Compositions on Control of Weeds Common to Rice Cropping Systems.

| Compound A Acid | Haloxyfop-methyl | Visual Weed Control (%) - 20 DAA | | | |
|---|---|---|---|---|---|
| | | ECHCO | | IPOHE | |
| gae/ha | gai/ha | Obs | Exp | Obs | Exp |
| 4.38 | 0 | 40 | — | 10 | — |
| 8.75 | 0 | 60 | — | 30 | — |
| 17.5 | 0 | 85 | — | 40 | — |
| 0 | 6.75 | 0 | — | 0 | — |
| 0 | 13.5 | 0 | — | 0 | — |
| 0 | 27 | 0 | — | 0 | — |
| 4.38 | 6.75 | 60 | 40 | 10 | 10 |
| 8.75 | 6.75 | 65 | 60 | 30 | 30 |
| 17.5 | 6.75 | 70 | 85 | 60 | 40 |
| 4.38 | 13.5 | 60 | 40 | 30 | 10 |
| 8.75 | 13.5 | 85 | 60 | 35 | 30 |
| 17.5 | 13.5 | 95 | 85 | 55 | 40 |
| 4.38 | 27 | 40 | 40 | 20 | 10 |
| 8.75 | 27 | 75 | 60 | 40 | 30 |
| 17.5 | 27 | 99 | 85 | 60 | 40 |

TABLE 6-continued

Synergistic Activity of Foliar-Applied Compound A Acid and Haloxyfop-methyl Herbicidal Compositions on Control of Weeds Common to Rice Cropping Systems.

| Compound A Acid | Haloxyfop-methyl | Visual Weed Control (%) - 20 DAA SCPJU | |
|---|---|---|---|
| gae/ha | gai/ha | Obs | Exp |
| 4.38 | 0 | 70 | — |
| 8.75 | 0 | 95 | — |
| 0 | 6.75 | 0 | — |
| 0 | 13.5 | 0 | — |
| 0 | 27 | 0 | — |
| 4.38 | 6.75 | 100 | 70 |
| 8.75 | 6.75 | 100 | 95 |
| 4.38 | 13.5 | 100 | 70 |
| 8.75 | 13.5 | 100 | 95 |
| 4.38 | 27 | 100 | 70 |
| 8.75 | 27 | 100 | 95 |

TABLE 7

Synergistic Activity of Foliar-Applied Compound A Benzyl Ester and Haloxyfop-methyl Herbicidal Compositions on Control of Weeds Common to Rice Cropping Systems.

| Compound A Benzyl Ester | Haloxyfop-methyl | Visual Weed Control (%) - 20 DAA BRAPP | |
|---|---|---|---|
| gae/ha | gai/ha | Obs | Exp |
| 4.38 | 0 | 50 | — |
| 8.75 | 0 | 70 | — |
| 0 | 6.75 | 0 | — |
| 0 | 13.5 | 0 | — |
| 4.38 | 6.75 | 60 | 50 |
| 8.75 | 6.75 | 70 | 70 |
| 4.38 | 13.5 | 70 | 50 |
| 8.75 | 13.5 | 85 | 70 |

| Compound A Benzyl Ester | Haloxyfop-methyl | Visual Weed Control (%) - 20 DAA SCPJU | |
|---|---|---|---|
| gae/ha | gai/ha | Obs | Exp |
| 4.38 | 0 | 30 | — |
| 8.75 | 0 | 60 | — |
| 0 | 6.75 | 0 | — |
| 0 | 13.5 | 0 | — |
| 0 | 27 | 0 | — |
| 4.38 | 6.75 | 100 | 30 |
| 8.75 | 6.75 | 100 | 60 |
| 4.38 | 13.5 | 99 | 30 |
| 8.75 | 13.5 | 100 | 60 |
| 4.38 | 27 | 90 | 30 |
| 8.75 | 27 | 100 | 60 |

TABLE 8

Synergistic Activity of Foliar-Applied Compound A Acid and Metamifop Herbicidal Compositions on Weed Control in a Rice Cropping System.

| Compound A Acid | Metamifop | Visual Weed Control (%) - 24 DAA IPOHE | |
|---|---|---|---|
| gae/ha | gai/ha | Obs | Exp |
| 4.38 | 0 | 10 | — |
| 8.75 | 0 | 10 | — |
| 17.5 | 0 | 30 | — |
| 0 | 150 | 0 | — |
| 4.38 | 150 | 15 | 10 |
| 8.75 | 150 | 25 | 10 |
| 17.5 | 150 | 40 | 30 |

TABLE 9

Synergistic Activity of Foliar-Applied Compound A Benzyl Ester and Metamifop Herbicidal Compositions on Weed Control in a Rice Cropping System.

| Compound A Benzyl Ester | Metamifop | Visual Weed Control (%) - 22 DAA ECHCG | |
|---|---|---|---|
| gae/ha | gai/ha | Obs | Exp |
| 8 | 0 | 35 | — |
| 16 | 0 | 65 | — |
| 32 | 0 | 80 | — |
| 0 | 9.38 | 0 | — |
| 0 | 18.75 | 40 | — |
| 0 | 37.5 | 70 | — |
| 8 | 9.38 | 60 | 35 |
| 16 | 9.38 | 80 | 65 |
| 32 | 9.38 | 90 | 80 |
| 8 | 18.75 | 85 | 61 |
| 16 | 18.75 | 95 | 79 |
| 32 | 18.75 | 99 | 88 |
| 8 | 37.5 | 100 | 81 |
| 16 | 37.5 | 100 | 90 |
| 32 | 37.5 | 99 | 94 |

| Compound A Benzyl Ester | Metamifop | Visual Weed Control (%) - 22 DAA IPOHE | |
|---|---|---|---|
| gae/ha | gai/ha | Obs | Exp |
| 32 | 0 | 45 | — |
| 0 | 9.38 | 0 | — |
| 0 | 18.75 | 0 | — |
| 0 | 37.5 | 0 | — |
| 32 | 9.38 | 50 | 45 |
| 32 | 18.75 | 60 | 45 |
| 32 | 37.5 | 65 | 45 |

TABLE 10

Synergistic Activity of Foliar-Applied Compound A Acid and Fluazifop-p-butyl Herbicidal Compositions on Control of Weeds Common to Rice Cropping Systems.

| Compound A Acid | Fluazifop-p-butyl | Visual Weed Control (%) - 19 DAA IPOHE | |
|---|---|---|---|
| gae/ha | gae/ha | Obs | Exp |
| 4.38 | 0 | 0 | — |
| 8.75 | 0 | 10 | — |
| 17.5 | 0 | 35 | — |
| 0 | 45 | 0 | — |
| 0 | 90 | 0 | — |
| 0 | 180 | 0 | — |
| 4.38 | 45 | 10 | 0 |
| 8.75 | 45 | 10 | 10 |
| 17.5 | 45 | 50 | 35 |
| 4.38 | 90 | 10 | 0 |
| 8.75 | 90 | 25 | 10 |
| 17.5 | 90 | 15 | 35 |
| 4.38 | 180 | 10 | 0 |
| 8.75 | 180 | 35 | 10 |
| 17.5 | 180 | 40 | 35 |

TABLE 11

Synergistic Activity of Foliar-Applied Compound A Benzyl Ester and Fluazifop-p-butyl Herbicidal Compositions on Control of Weeds Common to Rice Cropping Systems.

| Compound A Benzyl Ester | Fluazifop-p-butyl | Visual Weed Control (%) - 19 DAA IPOHE | |
|---|---|---|---|
| gae/ha | gae/ha | Obs | Exp |
| 4.38 | 0 | 0 | — |
| 8.75 | 0 | 0 | — |
| 0 | 45 | 0 | — |
| 0 | 90 | 0 | — |
| 0 | 180 | 0 | — |
| 4.38 | 45 | 10 | 0 |
| 8.75 | 45 | 20 | 0 |
| 4.38 | 90 | 15 | 0 |
| 8.75 | 90 | 20 | 0 |
| 4.38 | 180 | 20 | 0 |
| 8.75 | 180 | 10 | 0 |

TABLE 12

Synergistic Activity of Foliar-Applied Compound A Acid and Quizalofop-p-ethyl Herbicidal Compositions on Control of Weeds Common to Rice Cropping Systems.

| Compound A Acid | Quizalofop-p-ethyl | Visual Weed Control (%) - 20 DAA IPOHE | |
|---|---|---|---|
| gae/ha | gai/ha | Obs | Exp |
| 4.38 | 0 | 0 | — |
| 8.75 | 0 | 20 | — |
| 17.5 | 0 | 40 | — |
| 0 | 15 | 0 | — |
| 0 | 30 | 0 | — |
| 4.38 | 15 | NT | 0 |
| 8.75 | 15 | 45 | 20 |
| 17.5 | 15 | 70 | 40 |
| 4.38 | 30 | 60 | 0 |

TABLE 12-continued

Synergistic Activity of Foliar-Applied Compound A Acid and Quizalofop-p-ethyl Herbicidal Compositions on Control of Weeds Common to Rice Cropping Systems.

| Compound A Acid | Quizalofop-p-ethyl | Visual Weed Control (%) - 20 DAA IPOHE | |
|---|---|---|---|
| gae/ha | gai/ha | Obs | Exp |
| 8.75 | 30 | 90 | 20 |
| 17.5 | 30 | 70 | 40 |

TABLE 13

Synergistic Activity of Foliar-Applied Compound A Benzyl Ester and Quizalofop-p-ethyl Herbicidal Compositions on Control of Weeds Common to Rice Cropping Systems.

| Compound A Benzyl Ester | Quizalofop-p-ethyl | Visual Weed Control (%) - 22 DAA ECHCG | |
|---|---|---|---|
| gae/ha | gai/ha | Obs | Exp |
| 8 | 0 | 35 | — |
| 16 | 0 | 65 | — |
| 32 | 0 | 80 | — |
| 0 | 3.75 | 20 | — |
| 0 | 7.5 | 30 | — |
| 8 | 3.75 | 85 | 48 |
| 16 | 3.75 | 65 | 72 |
| 32 | 3.75 | 85 | 84 |
| 8 | 7.5 | 85 | 55 |
| 16 | 7.5 | 100 | 76 |
| 32 | 7.5 | 100 | 86 |

| Compound A Benzyl Ester | Quizalofop-p-ethyl | Visual Weed Control (%) - 22 DAA IPOHE | |
|---|---|---|---|
| gae/ha | gai/ha | Obs | Exp |
| 32 | 0 | 45 | — |
| 0 | 1.88 | 0 | — |
| 0 | 3.75 | 0 | — |
| 0 | 7.5 | 0 | — |
| 32 | 1.88 | 60 | 45 |
| 32 | 3.75 | 60 | 45 |
| 32 | 7.5 | 50 | 45 |

TABLE 14

Synergistic Activity of Foliar-Applied Compound A Benzyl Ester and Diclofop-methyl Herbicidal Compositions on Control of Weeds Common to Rice Cropping Systems.

| Compound A Benzyl Ester | Diclofop-methyl | Visual Weed Control (%) - 22 DAA CYPIR | |
|---|---|---|---|
| gae/ha | gai/ha | Obs | Exp |
| 8 | 0 | 20 | — |
| 16 | 0 | 85 | — |
| 32 | 0 | 100 | — |
| 0 | 280 | 0 | — |
| 0 | 560 | 0 | — |
| 0 | 1120 | 0 | — |
| 8 | 280 | 30 | 20 |
| 16 | 280 | 100 | 85 |
| 32 | 280 | 100 | 100 |
| 8 | 560 | 35 | 20 |
| 16 | 560 | 75 | 85 |
| 32 | 560 | 100 | 100 |
| 8 | 1120 | 50 | 20 |
| 16 | 1120 | 100 | 85 |
| 32 | 1120 | 100 | 100 |

TABLE 15

Synergistic Activity of Foliar-Applied Compound A Acid and Profoxydim Herbicidal Compositions on Weed Control in a Rice Cropping System.

| Compound A Acid | Profoxydim | Visual Weed Control (%) - 20 DAA ECHCO | |
|---|---|---|---|
| gae/ha | gai/ha | Obs | Exp |
| 4.38 | 0 | 40 | — |
| 0 | 12.5 | 70 | — |
| 4.38 | 12.5 | 99 | 82 |

TABLE 16

Synergistic Activity of Foliar-Applied Compound A Benzyl Ester and Profoxydim Herbicidal Compositions on Weed Control in a Rice Cropping System.

| Comopund A Benzyl Ester | Profoxydim | Visual Weed Control (%) - 20 DAA LEFCH | |
|---|---|---|---|
| gae/ha | gai/ha | Obs | Exp |
| 4.38 | 0 | 0 | — |
| 8.75 | 0 | 10 | — |
| 17.5 | 0 | 25 | — |
| 0 | 12.5 | 0 | — |
| 0 | 25 | 40 | — |
| 4.38 | 12.5 | 10 | 0 |
| 8.75 | 12.5 | 30 | 10 |
| 17.5 | 12.5 | 50 | 25 |
| 4.38 | 25 | 50 | 40 |
| 8.75 | 25 | 50 | 46 |
| 17.5 | 25 | 70 | 55 |

TABLE 17

Synergistic Activity of Foliar-Applied Compound A Acid and Sethoxydim Herbicidal Compositions on Control of Weeds Common to Rice Cropping Systems.

| Compound A Acid | Sethoxydim | Visual Weed Control (%) - 22 DAA CYPES | |
|---|---|---|---|
| gae/ha | gai/ha | Obs | Exp |
| 4.38 | 0 | 50 | — |
| 8.75 | 0 | 75 | — |
| 0 | 67.5 | 0 | — |
| 0 | 135 | 0 | — |
| 0 | 270 | 0 | — |
| 4.38 | 67.5 | 80 | 50 |
| 8.75 | 67.5 | 80 | 75 |
| 4.38 | 135 | 70 | 50 |
| 8.75 | 135 | 100 | 75 |
| 4.38 | 270 | 100 | 50 |
| 8.75 | 270 | 70 | 75 |

| Compound A Acid | Sethoxydim | CYPDI | | CYPIR | | SCPJU | |
|---|---|---|---|---|---|---|---|
| gae/ha | gai/ha | Obs | Exp | Obs | Exp | Obs | Exp |
| 4.38 | 0 | 60 | — | 15 | — | 60 | — |
| 0 | 67.5 | 0 | — | 0 | — | 0 | — |
| 0 | 135 | 0 | — | 0 | — | 0 | — |
| 0 | 270 | 0 | — | 0 | — | 0 | — |
| 4.38 | 67.5 | 100 | 60 | 80 | 15 | 80 | 60 |
| 4.38 | 135 | 100 | 60 | 80 | 15 | 85 | 60 |
| 4.38 | 270 | 90 | 60 | 60 | 15 | 70 | 60 |

TABLE 18

Synergistic Activity of Foliar-Applied Compound A Benzyl Ester and Sethoxydim Herbicidal Compositions on Control of Weeds Common to Rice Cropping Systems.

| Compound A Benzyl Ester | Sethoxydim | Visual Weed Control (%) - 22 DAA ECHCG | |
|---|---|---|---|
| gae/ha | gai/ha | Obs | Exp |
| 8 | 0 | 35 | — |
| 16 | 0 | 65 | — |
| 32 | 0 | 80 | — |
| 0 | 56 | 30 | — |
| 0 | 112 | 90 | — |
| 8 | 56 | 90 | 55 |
| 16 | 56 | 99 | 76 |
| 32 | 56 | 95 | 86 |
| 8 | 112 | 100 | 94 |
| 16 | 112 | 99 | 97 |
| 32 | 112 | 100 | 98 |

| Compound A Benzyl Ester | Sethoxydim | Visual Weed Control (%) - 22 DAA LEFCH | |
|---|---|---|---|
| gae/ha | gai/ha | Obs | Exp |
| 8 | 0 | 15 | — |
| 16 | 0 | 50 | — |
| 0 | 112 | 70 | — |
| 8 | 112 | 100 | 75 |
| 16 | 112 | 100 | 85 |

TABLE 19

Synergistic Activity of Foliar-Applied Compound A Benzyl Ester and Tralkoxydim Herbicidal Compositions on Control of Weeds Common to Rice Cropping Systems.

| Compound A Benzyl Ester | Tralkoxydim | Visual Weed Control (%) - 22 DAA CYPIR | |
|---|---|---|---|
| gae/ha | gai/ha | Obs | Exp |
| 8 | 0 | 20 | — |
| 16 | 0 | 85 | — |
| 32 | 0 | 100 | — |
| 0 | 100 | 0 | — |
| 0 | 200 | 0 | — |
| 8 | 100 | 20 | 20 |
| 16 | 100 | 100 | 85 |
| 32 | 100 | 90 | 100 |
| 8 | 200 | 100 | 20 |
| 16 | 200 | 60 | 85 |
| 32 | 200 | 100 | 100 |

TABLE 20

Synergistic Activity of Foliar-Applied Compound A Benzyl Ester and Pinoxaden Herbicidal Compositions on Control of Weeds Common to Rice Cropping Systems.

| Compound A Benzyl Ester | Pinoxaden | Visual Weed Control (%) - 21 DAA ECHCO | |
|---|---|---|---|
| gae/ha | gai/ha | Obs | Exp |
| 8 | 0 | 40 | — |
| 16 | 0 | 70 | — |
| 32 | 0 | 95 | — |
| 0 | 15 | 15 | — |
| 0 | 30 | 85 | — |
| 0 | 60 | 95 | — |
| 8 | 15 | 75 | 49 |
| 16 | 15 | 85 | 75 |
| 32 | 15 | 95 | 96 |
| 8 | 30 | 95 | 91 |
| 16 | 30 | 95 | 96 |
| 32 | 30 | 95 | 99 |
| 8 | 60 | 100 | 97 |
| 16 | 60 | 100 | 99 |
| 32 | 60 | 100 | 100 |

| Compound A Benzyl Ester | Pinoxaden | Visual Weed Control (%) - 21 DAA IPOHE | |
|---|---|---|---|
| gae/ha | gai/ha | Obs | Exp |
| 16 | 0 | 10 | — |
| 32 | 0 | 25 | — |
| 0 | 15 | 10 | — |
| 0 | 30 | 10 | — |
| 0 | 60 | 0 | — |
| 16 | 15 | 20 | 19 |
| 32 | 15 | 60 | 33 |
| 16 | 30 | 25 | 19 |
| 32 | 30 | 40 | 33 |

TABLE 20-continued

Synergistic Activity of Foliar-Applied Compound A Benzyl Ester and Pinoxaden Herbicidal Compositions on Control of Weeds Common to Rice Cropping Systems.

| 16 | 60 | 15 | 10 |
| 32 | 60 | 50 | 25 |

| Compound A Benzyl Ester | Pinoxaden | Visual Weed Control (%) - 21 DAA SCPJU | |
| --- | --- | --- | --- |
| gae/ha | gai/ha | Obs | Exp |
| 8 | 0 | 85 | — |
| 0 | 15 | 0 | — |
| 0 | 30 | 0 | — |
| 0 | 60 | 0 | — |
| 8 | 15 | 99 | 85 |
| 8 | 30 | 100 | 85 |
| 8 | 60 | 100 | 85 |

TABLE 21

Synergistic Activity of Foliar-Applied Compound A Benzyl Ester and Clethodim Herbicidal Compositions on Control of Weeds Common to Rice Cropping Systems.

| Compound A Benzyl Ester | Clethodim | Visual Weed Control (%) - 20 DAA | | | |
| --- | --- | --- | --- | --- | --- |
| | | BRAPP | | DIGSA | |
| gae/ha | gai/ha | Obs | Exp | Obs | Exp |
| 8 | 0 | 70 | — | 15 | — |
| 16 | 0 | 75 | — | 25 | — |
| 32 | 0 | 90 | — | 35 | — |
| 0 | 70 | 10 | — | 50 | — |
| 8 | 70 | 100 | 73 | 75 | 58 |
| 16 | 70 | 100 | 78 | 80 | 63 |
| 32 | 70 | 100 | 91 | 85 | 68 |

| Compound A Benzyl Ester | Clethodim | Visual Weed Control (%) - 20 DAA CYPES | |
| --- | --- | --- | --- |
| gae/ha | gai/ha | Obs | Exp |
| 8 | 0 | 0 | — |
| 16 | 0 | 75 | — |
| 0 | 70 | 0 | — |
| 0 | 140 | 0 | — |
| 0 | 280 | 0 | — |
| 8 | 70 | 60 | 0 |
| 16 | 70 | 85 | 75 |
| 8 | 140 | 80 | 0 |
| 16 | 140 | 95 | 75 |
| 8 | 280 | 95 | 0 |
| 16 | 280 | 90 | 75 |

| Compound A Benzyl Ester | Clethodim | Visual Weed Control (%) - 20 DAA SCPJU | |
| --- | --- | --- | --- |
| gae/ha | gai/ha | Obs | Exp |
| 8 | 0 | 70 | — |
| 16 | 0 | 85 | — |
| 0 | 140 | 0 | — |
| 0 | 280 | 0 | — |
| 8 | 140 | 100 | 70 |
| 16 | 140 | 100 | 85 |
| 8 | 280 | 100 | 70 |
| 16 | 280 | 85 | 85 |

| BRAPP | *Brachiaria platyphylla* (Griseb.) Nash | signalgrass, broadleaf |
| --- | --- | --- |
| CYPDI | *Cyperus difformis* L. | sedge, smallflower umbrella |
| CYPES | *Cyperus esculentus* L. | nutsedge, yellow |
| CYPIR | *Cyperus iria* L. | flatsedge, rice |
| DIGSA | *Digitaria sanguinalis* (L.) Scop. | crabgrass, large |
| ECHCG | *Echinochloa crusgalli* (L.) Beauv. | barnyardgrass |
| ECHCO | *Echinochloa colona* (L.) Link | junglerice |
| IPOHE | *Ipomoea hederacea* Jacq. | morningglory, ivyleaf |
| ISCRU | *Ischaemum rugosum* Salisb. | saramollagrass |
| LEFCH | *Leptochloa chinensis* (L.) Nees | sprangletop, Chinese |
| SCPJU | *Schoenoplectus juncoides* (Roxb.) Palla | bulrush, Japanese | gae/ha = grams acid equivalent per hectare
gai/ha = grams active ingredient per hectare
Obs = observed value
Exp = expected value as calculated by Colby's equation
DAA = days after application
NT = not tested Example II Evaluation of In-Water Applied Herbicidal Mixtures for Weed Control in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters ($cm^2$) leaving a headspace of 3 centimeters (cm) in each pot. Mud was allowed to dry overnight prior to planting or transplanting. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 860 mL of mud contained in 32-oz. non-perforated plastic pots with a surface area of 86.59 $cm^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 hr photoperiod which was maintained at about 29'C during the day and 26° C. during the night. Nutrients were added as Osmocote® (19:6:12, N:P:K+minor nutrients) at 2 g per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (compound A) each formulated as an SC (suspension concentrate) and various herbicidal components alone and in combination. Forms of compound A were applied on an acid equivalent basis.

Forms of Compound a (Compound of Formula I) Tested Include:

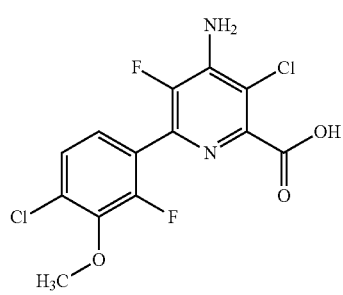

Compound A

Acid

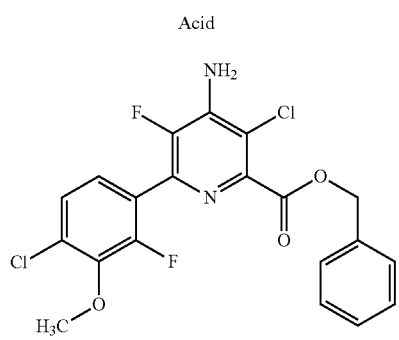

Compound A

Benzyl Ester

Other herbicidal components were applied on an acid equivalent (ae) or active ingredient (ai) basis as to normal practice used in the market, and included acetyl CoA carboxylase (ACCase) inhibiting herbicides (cyclohexanedione and aryloxyphenoxypropionate chemical classes) cyhalofop-butyl formulated as Clincher® EC, fenoxaprop-p-ethyl+ isoxadifen-ethyl formulated as RiceStar® HT, fenoxaprop-p-ethyl+mefenpyr diethyl formulated as Puma 1EC, metamifop formulated as Metamifop EC, haloxyfop-methyl formulated as Gallant Super®, fluazifop-p-butyl formulated as Fusilade® DX, quizalofop-p-ethyl formulated as Assure® II, profoxydim formulated as Aura® 20EC, and sethoxydim formulated as Poast®.

Treatment requirements for each compound or herbicidal component were calculated based upon the rates being tested, the concentration of active ingredient or acid equivalent in the formulation, an application volume of 2 mL per component per pot, and an application area of 86.59 cm² per pot.

For formulated compounds, a measured amount was placed in an individual 100 or 200 mL glass vial and was dissolved in a volume of 1.25% (v/v) Agri-Dex® crop oil concentrate to obtain application solutions. If the test compound did not dissolve readily, the mixture was warmed and/or sonicated.

For technical grade compounds, a weighed amount can be placed in an individual 100 to 200 mL glass vial and dissolved in a volume of acetone to obtain concentrated stock solutions. If the test compound does not dissolve readily, the mixture can be warmed and/or sonicated. The concentrated stock solutions obtained can be diluted with an equivalent volume of an aqueous mixture containing 2.5% (v/v) crop oil concentrate so that the final application solutions contain 1.25% (v/v) crop oil concentrate.

Applications were made by injecting with a pipetter appropriate amounts of the application solutions, individually and sequentially, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

Expected=$A+B-(A \times B/100)$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 22-39.

TABLE 22

Synergistic Activity of In-Water Applications of Compound A Acid and Cyhalofop-butyl Herbicidal Compositions on Weed Control in a Rice Cropping System.

| Compound A Acid | Cyhalofop-butyl | Visual Weed Control (%) - 25 DAA ECHOR | |
|---|---|---|---|
| gae/ha | gai/ha | Obs | Exp |
| 8.75 | 0 | 0 | — |
| 17.5 | 0 | 0 | — |
| 35 | 0 | 40 | — |
| 0 | 90 | 0 | — |
| 8.75 | 90 | 100 | 0 |
| 17.5 | 90 | 100 | 0 |
| 35 | 90 | 100 | 40 |

| Compound A Acid | Cyhalofop-butyl | Visual Weed Control (%) - 25 DAA SCPJU | |
|---|---|---|---|
| gae/ha | gai/ha | Obs | Exp |
| 8.75 | 0 | 65 | — |
| 17.5 | 0 | 80 | — |
| 35 | 0 | 95 | — |
| 0 | 90 | 0 | — |
| 0 | 180 | 0 | — |
| 8.75 | 90 | 95 | 65 |
| 17.5 | 90 | 95 | 80 |
| 35 | 90 | 100 | 95 |
| 8.75 | 180 | 95 | 65 |

TABLE 22-continued

Synergistic Activity of In-Water Applications of Compound A Acid and Cyhalofop-butyl Herbicidal Compositions on Weed Control in a Rice Cropping System.

| 17.5 | 180 | 95 | 80 |
| 35 | 180 | 95 | 95 |

| Compound A Acid | Cyhalofop-butyl | Visual Weed Control (%) - 19 DAA LEFCH | |
|---|---|---|---|
| gae/ha | gai/ha | Obs | Exp |
| 42.4 | 0 | 10 | — |
| 0 | 180 | 75 | — |
| 42.4 | 180 | 90 | 78 |

TABLE 23

Synergistic Activity of In-Water Applications of Compound A Benzyl Ester and Cyhalofop-butyl Herbicidal Compositions on Weed Control in a Rice Cropping System.

| Compound A Benzyl Ester | Cyhalofop-butyl | Visual Weed Control (%) - 25 DAA ECHOR | |
|---|---|---|---|
| gae/ha | gai/ha | Obs | Exp |
| 8.75 | 0 | 85 | — |
| 17.5 | 0 | 90 | — |
| 35 | 0 | 100 | — |
| 0 | 90 | 0 | — |
| 8.75 | 90 | 100 | 85 |
| 17.5 | 90 | 100 | 90 |
| 35 | 90 | 100 | 100 |

| Compound A Benzyl Ester | Cyhalofop-butyl | Visual Weed Control (%) - 19 DAA SCPMA | |
|---|---|---|---|
| gae/ha | gai/ha | Obs | Exp |
| 35 | 0 | 0 | — |
| 0 | 180 | 0 | — |
| 35 | 180 | 50 | 0 |

TABLE 24

Synergistic Activity of In-Water Applications of Compound A Acid and Fenoxaprop-p-ethyl + Isoxadifen-ethyl Herbicidal Compositions on Weed Control in a Rice Cropping System.

| Compound A Acid | Fenoxaprop-p-ethyl + Isoxadifen-ethyl | Visual Weed Control (%) - 21 DAA ECHOR | |
|---|---|---|---|
| gae/ha | gai/ha | Obs | Exp |
| 8.75 | 0 | 0 | — |
| 17.5 | 0 | 10 | — |
| 35 | 0 | 15 | — |
| 0 | 70 | 50 | — |
| 8.75 | 70 | 100 | 50 |
| 17.5 | 70 | 50 | 55 |
| 35 | 70 | 100 | 58 |

| Compound A Acid | Fenoxaprop-p-ethyl + Isoxadifen-ethyl | Visual Weed Control (%) - 21 DAA FIMMI | |
|---|---|---|---|
| gae/ha | gai/ha | Obs | Exp |
| 8.75 | 0 | 20 | — |
| 0 | 35 | 0 | — |
| 0 | 70 | 0 | — |
| 8.75 | 35 | 100 | 20 |
| 8.75 | 70 | 60 | 20 |

| Compound A Acid | Fenoxaprop-p-ethyl + Isoxadifen-ethyl | Visual Weed Control (%) - 21 DAA SCPJU | |
|---|---|---|---|
| gae/ha | gai/ha | Obs | Exp |
| 8.75 | 0 | 65 | — |
| 17.5 | 0 | 90 | — |
| 0 | 35 | 0 | — |
| 0 | 70 | 0 | — |
| 8.75 | 35 | 80 | 65 |
| 17.5 | 35 | 99 | 90 |
| 8.75 | 70 | 85 | 65 |
| 17.5 | 70 | 95 | 90 |

TABLE 25

Synergistic Activity of In-Water Applications of Compound A Benzyl Ester and Fenoxaprop-p-ethyl + Isoxadifen-ethyl Herbicidal Compositions on Weed Control in a Rice Cropping System.

| Compound A Benzyl Ester | Fenoxaprop-p-ethyl + Isoxadifen-ethyl | Visual Weed Control (%) - 21 DAA ECHOR | |
|---|---|---|---|
| gae/ha | gai/ha | Obs | Exp |
| 4.38 | 0 | 0 | — |
| 8.75 | 0 | 10 | — |
| 17.5 | 0 | 60 | — |
| 0 | 70 | 50 | — |
| 4.38 | 70 | 100 | 50 |
| 8.75 | 70 | 100 | 55 |
| 17.5 | 70 | 100 | 80 |

| Compound A Benzyl Ester | Fenoxaprop-p-ethyl + Isoxadifen-ethyl | Visual Weed Control (%) - 21 DAA CYPRO | |
|---|---|---|---|
| gae/ha | gai/ha | Obs | Exp |
| 4.38 | 0 | 20 | — |
| 0 | 35 | 0 | — |
| 0 | 70 | 0 | — |
| 4.38 | 35 | 99 | 20 |
| 4.38 | 70 | 50 | 20 |

TABLE 26

Synergistic Activity of In-Water Applications of Compound A Acid and Fenoxaprop-p-ethyl + Mefenpyr-diethyl Herbicidal Compositions on Control of Weeds Common to Rice Cropping Systems.

| Compound A Acid | Fenoxaprop-p-ethyl + Mefenpyr diethyl | Visual Weed Control (%) - 21 DAA ECHOR | |
|---|---|---|---|
| gae/ha | gai/ha | Obs | Exp |
| 10.6 | 0 | 0 | — |
| 21.2 | 0 | 15 | — |
| 42.4 | 0 | 15 | — |
| 0 | 23 | 0 | — |
| 10.6 | 23 | 25 | 0 |
| 21.2 | 23 | 15 | 15 |
| 42.4 | 23 | 40 | 15 |

TABLE 27

Synergistic Activity of In-Water Applications of Compound A Benzyl Ester and Fenoxaprop-p-ethyl + Mefenpyr-diethyl Herbicidal Compositions on Control of Weeds Common to Rice Cropping Systems.

| Compound A Benzyl Ester | Fenoxaprop-p-ethyl + Mefenpyr-diethyl | Visual Weed Control (%) - 21 DAA ECHOR | |
|---|---|---|---|
| gae/ha | gai/ha | Obs | Exp |
| 8 | 0 | 10 | — |
| 16 | 0 | 25 | — |
| 32 | 0 | 35 | — |
| 0 | 23 | 15 | — |
| 8 | 23 | 100 | 24 |
| 16 | 23 | 20 | 36 |
| 32 | 23 | 75 | 45 |

TABLE 28

Synergistic Activity of In-Water Applications of Compound A Acid and Haloxyfop-methyl Herbicidal Compositions on Control of Weeds Common to Rice Cropping Systems.

| Compound A Acid | Haloxyfop-methyl | Visual Weed Control (%) - 20 DAA SCPJU | |
|---|---|---|---|
| gae/ha | gai/ha | Obs | Exp |
| 8.75 | 0 | 70 | — |
| 17.5 | 0 | 95 | — |
| 35 | 0 | 95 | — |
| 0 | 13.5 | 0 | — |
| 0 | 27 | 0 | — |
| 8.75 | 13.5 | 90 | 70 |
| 17.5 | 13.5 | 95 | 95 |
| 35 | 13.5 | 95 | 95 |
| 8.75 | 27 | 95 | 70 |
| 17.5 | 27 | 100 | 95 |
| 35 | 27 | 100 | 95 |

TABLE 29

Synergistic Activity of In-Water Applications of Compound A Benzyl Ester and Haloxyfop-methyl Herbicidal Compositions on Control of Weeds Common to Rice Cropping Systems

| Compound A Benzyl Ester | Haloxyfop-methyl | Visual Weed Control (%) - 20 DAA CYPRO | |
|---|---|---|---|
| gae/ha | gai/ha | Obs | Exp |
| 4.38 | 0 | 50 | — |
| 8.75 | 0 | 100 | — |
| 17.5 | 0 | 100 | — |
| 0 | 13.5 | 0 | — |
| 0 | 27 | 0 | — |
| 4.38 | 13.5 | 75 | 50 |
| 8.75 | 13.5 | 95 | 100 |
| 17.5 | 13.5 | 100 | 100 |
| 4.38 | 27 | 80 | 50 |
| 8.75 | 27 | 95 | 100 |
| 17.5 | 27 | 100 | 100 |

TABLE 30

Synergistic Activity of In-Water Applications of Compound A Acid and Metamifop Herbicidal Compositions on Weed Control in a Rice Cropping System.

| Compound A Acid | Metamifop | Visual Weed Control (%) - 21 DAA | | | |
|---|---|---|---|---|---|
| | | FIMMI | | SCPMA | |
| gae/ha | gai/ha | Obs | Exp | Obs | Exp |
| 35 | 0 | 85 | — | 0 | — |
| 0 | 75 | 0 | — | 0 | — |
| 0 | 150 | 0 | — | 0 | — |
| 35 | 75 | 100 | 85 | 60 | 0 |
| 35 | 150 | 100 | 85 | 50 | 0 |

TABLE 31

Synergistic Activity of In-Water Applications of Compound A Benzyl Ester and Metamifop Herbicidal Compositions on Weed Control in a Rice Cropping System.

| Compound A Benzyl Ester | Metamifop | Visual Weed Control (%) - 21 DAA SCPJU | |
|---|---|---|---|
| gae/ha | gai/ha | Obs | Exp |
| 4.38 | 0 | 70 | — |
| 0 | 75 | 0 | — |
| 0 | 150 | 0 | — |
| 4.38 | 75 | 99 | 70 |
| 4.38 | 150 | 100 | 70 |

| Compound A Benzyl Ester | Metamifop | Visual Weed Control (%) - 21 DAA ECHOR | |
|---|---|---|---|
| gae/ha | gai/ha | Obs | Exp |
| 48 | 0 | 78 | — |
| 96 | 0 | 80 | — |
| 0 | 50 | 20 | — |
| 48 | 50 | 75 | 82 |
| 96 | 50 | 100 | 84 |

TABLE 32

Synergistic Activity of In-Water Applications of Compound A Acid and Fluazifop-p-butyl Herbicidal Compositions on Control of Weeds Common to Rice Cropping Systems.

| Compound A Acid | Fluazifop-P-butyl | Visual Weed Control (%) - 21 DAA ECHOR | |
|---|---|---|---|
| gae/ha | gae/ha | Obs | Exp |
| 8.75 | 0 | 10 | — |
| 17.5 | 0 | 15 | — |
| 35 | 0 | 20 | — |
| 0 | 90 | 25 | — |
| 8.75 | 90 | 45 | 33 |
| 17.5 | 90 | 15 | 36 |
| 35 | 90 | 100 | 40 |

| Compound A Acid | Fluazifop-P-butyl | Visual Weed Control (%) - 21 DAA CYPRO | |
|---|---|---|---|
| gae/ha | gae/ha | Obs | Exp |
| 8.75 | 0 | 0 | — |
| 17.5 | 0 | 30 | — |
| 35 | 0 | 85 | — |
| 0 | 90 | 0 | — |
| 0 | 180 | 0 | — |
| 8.75 | 90 | 70 | 0 |
| 17.5 | 90 | 30 | 30 |
| 35 | 90 | 95 | 85 |
| 8.75 | 180 | 20 | 0 |
| 17.5 | 180 | 20 | 30 |
| 35 | 180 | 90 | 85 |

TABLE 33

Synergistic Activity of In-Water Applications of Compound A Benzyl Ester and Fluazifop-p-butyl Herbicidal Compositions on Control of Weeds Common to Rice Cropping Systems.

| Compound A Benzyl Ester | Fluazifop-P-butyl | Visual Weed Control (%) - 21 DAA ECHOR | |
|---|---|---|---|
| gae/ha | gai/ha | Obs | Exp |
| 8 | 0 | 8 | — |
| 16 | 0 | 5 | — |
| 32 | 0 | 13 | — |
| 0 | 45 | 0 | — |
| 8 | 45 | 0 | 8 |
| 16 | 45 | 15 | 5 |
| 32 | 45 | 30 | 13 |

TABLE 34

Synergistic Activity of In-Water Applications of Compound A Acid and Quizalofop-p-ethyl Herbicidal Compositions on Control of Weeds Common to Rice Cropping Systems.

| Compound A Acid | Quizalofop-p-ethyl | Visual Weed Control (%) - 21 DAA ECHOR | |
|---|---|---|---|
| gae/ha | gai/ha | Obs | Exp |
| 17.5 | 0 | 25 | — |
| 35 | 0 | 30 | — |
| 0 | 15 | 0 | — |
| 0 | 30 | 60 | — |
| 17.5 | 15 | 50 | 25 |
| 35 | 15 | 50 | 30 |
| 17.5 | 30 | 60 | 70 |
| 35 | 30 | 100 | 72 |

| Compound A Acid | Quizalofop-p-ethyl | Visual Weed Control (%) - 21 DAA CYPRO | |
|---|---|---|---|
| gae/ha | gai/ha | Obs | Exp |
| 8.75 | 0 | 0 | — |
| 0 | 15 | 0 | — |
| 0 | 30 | 0 | — |
| 8.75 | 15 | 20 | 0 |
| 8.75 | 30 | 20 | 0 |

TABLE 35

Synergistic Activity of In-Water Applications of Compound A Benzyl Ester and Quizalofop-p-ethyl Herbicidal Compositions on Control of Weeds Common to Rice Cropping Systems.

| Compound A Benzyl Ester | Quizalofop-p-ethyl | Visual Weed Control (%) - 21 DAA | | | |
|---|---|---|---|---|---|
| | | ECHCG | | ECHOR | |
| gae/ha | gai/ha | Obs | Exp | Obs | Exp |
| 4.38 | 0 | 15 | — | 0 | — |
| 8.75 | 0 | 20 | — | 15 | — |
| 17.5 | 0 | 75 | — | 10 | — |
| 0 | 15 | 50 | — | 0 | — |
| 0 | 30 | 100 | — | 60 | — |
| 4.38 | 15 | 100 | 58 | 60 | 0 |
| 8.75 | 15 | 100 | 60 | 30 | 15 |
| 17.5 | 15 | 100 | 88 | 50 | 10 |
| 4.38 | 30 | 100 | 100 | 100 | 60 |
| 8.75 | 30 | 100 | 100 | 100 | 66 |
| 17.5 | 30 | 100 | 100 | 100 | 64 |

TABLE 36

Synergistic Activity of In-Water Applications of Compound A Acid and Profoxydim Herbicidal Compositions on Control of Weeds Common to Rice Cropping Systems.

| Compound A Acid | Profoxydim | Visual Weed Control (%) - 21 DAA LEFCH | |
|---|---|---|---|
| gae/ha | gai/ha | Obs | Exp |
| 17.5 | 0 | 0 | — |
| 35 | 0 | 20 | — |
| 0 | 25 | 85 | — |

TABLE 36-continued

Synergistic Activity of In-Water Applications of Compound A Acid and Profoxydim Herbicidal Compositions on Control of Weeds Common to Rice Cropping Systems.

| 17.5 | 25 | 100 | 85 |
| 35 | 25 | 100 | 88 |

| Compound A Acid | Profoxydim | Visual Weed Control (%) - 22 DAA ECHCG | |
| --- | --- | --- | --- |
| gae/ha | gai/ha | Obs | Exp |
| 16 | 0 | 20 | — |
| 32 | 0 | 25 | — |
| 0 | 50 | 30 | — |
| 16 | 50 | 70 | 44 |
| 32 | 50 | 100 | 48 |

| Compound A Acid | Profoxydim | Visual Weed Control (%) - 22 DAA SCPJU | |
| --- | --- | --- | --- |
| gae/ha | gai/ha | Obs | Exp |
| 16 | 0 | 70 | — |
| 0 | 50 | 0 | — |
| 0 | 100 | 0 | — |
| 16 | 50 | 95 | 70 |
| 16 | 100 | 100 | 70 |

TABLE 37

Synergistic Activity of In-Water Applications of Compound A Benzyl Ester and Profoxydim Herbicidal Compositions on Control of Weeds Common to Rice Cropping Systems.

| Compound A Benzyl Ester | Profoxydim | Visual Weed Control (%) - 21 DAA ECHOR | |
| --- | --- | --- | --- |
| gae/ha | gai/ha | Obs | Exp |
| 4.38 | 0 | 0 | — |
| 8.75 | 0 | 15 | — |
| 17.5 | 0 | 10 | — |
| 0 | 25 | 0 | — |
| 4.38 | 25 | 30 | 0 |
| 8.75 | 25 | 100 | 15 |
| 17.5 | 25 | 100 | 10 |

| Compound A Benzyl Ester | Profoxydim | Visual Weed Control (%) - 22 DAA ECHCG | |
| --- | --- | --- | --- |
| gae/ha | gai/ha | Obs | Exp |
| 8 | 0 | 50 | — |
| 16 | 0 | 60 | — |
| 32 | 0 | 99 | — |
| 0 | 50 | 30 | — |
| 8 | 50 | 100 | 65 |
| 16 | 50 | 100 | 72 |
| 32 | 50 | 100 | 99 |

TABLE 38

Synergistic Activity of In-Water Applications of Compound A Acid and Sethoxydim Herbicidal Compositions on Control of Weeds Common to Rice Cropping Systems.

| Compound A Acid | Sethoxydim | Visual Weed Control (%) - 21 DAA FIMMI | |
| --- | --- | --- | --- |
| gae/ha | gai/ha | Obs | Exp |
| 8.75 | 0 | 20 | — |
| 0 | 135 | 50 | — |
| 0 | 270 | 30 | — |
| 8.75 | 135 | 100 | 60 |
| 8.75 | 270 | 100 | 44 |

| Compound A Acid | Sethoxydim | Visual Weed Control (%) - 21 DAA SCPJU | |
| --- | --- | --- | --- |
| gae/ha | gai/ha | Obs | Exp |
| 8.75 | 0 | 65 | — |
| 17.5 | 0 | 90 | — |
| 0 | 135 | 0 | — |
| 8.75 | 135 | 95 | 65 |
| 17.5 | 135 | 100 | 90 |

TABLE 39

Synergistic Activity of In-Water Applications of Compound A Benzyl Ester and Sethoxydim Herbicidal Compositions on Control of Weeds Common to Rice Cropping Systems.

| Compound A Benzyl Ester | Sethoxydim | Visual Weed Control (%) - 21 DAA ECHCG | |
| --- | --- | --- | --- |
| gae/ha | gai/ha | Obs | Exp |
| 4.38 | 0 | 15 | — |
| 8.75 | 0 | 60 | — |
| 0 | 135 | 60 | — |
| 4.38 | 135 | 75 | 66 |
| 8.75 | 135 | 100 | 84 |

CYPRO   *Cyperus rotundus* L.   nutsedge, purple
ECHCG   *Echinochloa crusgalli* (L.) Beauv.   barnyardgrass
ECHOR   *Echinochloa oryzoides* (Ard.) Fritsch   watergrass, early
FIMMI   *Fimbristylis miliacea* (L.) Vahl   fringerush, globe
LEFCH   *Leptochloa chinensis* (L.) Nees   sprangletop, Chinese
SCPJU   *Schoenoplectus juncoides* (Roxb.) Palla   bulrush, Japanese
SCPMA   *Bolboschoenus maritimus* (L.) Palla or *Schoenoplectus maritimus* (L.) Lye   clubrush, sea
gae/ha = grams acid equivalent per hectare
gai/ha = grams active ingredient per hectare
Obs = observed value
Exp = expected value as calculated by Colby's equation
DAA = days after application Example III Evaluation of Postemergence Foliar-Applied Herbicidal Mixtures for Control of Weeds Common to Row Crops such as Corn and Soybeans Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a surface area of 84.6 square centimeters (cm$^2$) and a volume of 560 cubic centimeters (cm$^3$). When required to ensure good germination and healthy plants, a fungicide treatment and/or other chemical or physical treatment was applied. The plants were grown for 7-31 days (d) in a greenhouse with an approximate 15 hour (h) photoperiod which was maintained at about 23-29° C. during the day and 22-28° C. during the night. Nutrients (Peters Excel® 15-5-15 5-Ca 2-Mg) and water were added on a regular basis and supplemental lighting was provided with overhead metal halide 1000-Watt lamps as necessary. The plants were employed for testing when they reached the first, second, or third true leaf stage.

Treatment requirements were calculated based upon the rates being tested, the concentration of active ingredient or acid equivalent in the formulation, and a 12 mL application volume at a rate of 187 L/ha.

Treatments consisted of the acid or esters of 4-amino-3-chloro-5-fluoro-6-(4-chloro-2-fluoro-3-methoxy-phenyl)pyridine-2-carboxylic acid (Compound A), each formulated as an SC (suspension concentrate), and various herbicidal components alone and in combination. Forms of compound A were applied on an acid equivalent basis.

Forms of Compound a (Compound of Formula I) Tested Include:

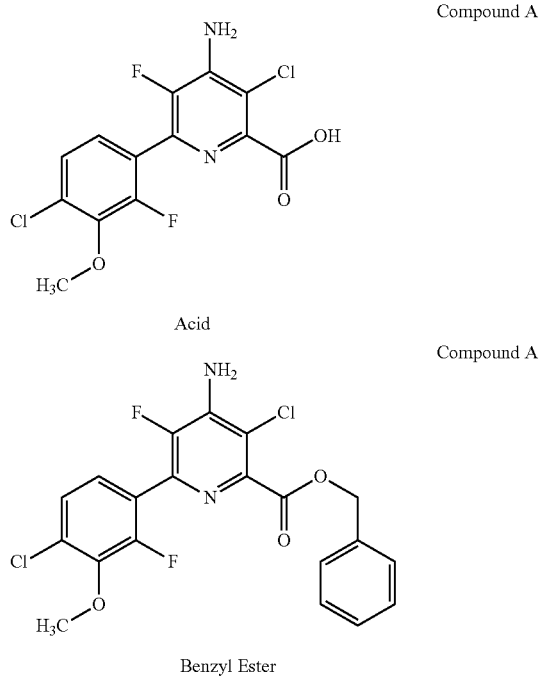

Other herbicidal components were applied on an acid equivalent basis and included acetyl coA carboxylase (AC-Case)-inhibiting herbicide (cyclohexanedione and aryloxyphenoxypropionate chemical classes) quizalofop-p-ethyl formulated as Assure® II.

For treatments comprised of formulated compounds, measured amounts of compounds were placed individually in 25 mL glass vials and diluted in a volume of 1.5% (v/v) Agri-Dex® crop oil concentrated to obtain 6× stock solutions. If a test compound did not dissolve readily, the mixture was warmed and/or sonicated. Application solutions were prepared by adding an appropriate amount of each stock solution (typically 2 mL) and diluted to the appropriate final concentrations with the addition of an appropriate amount of 1.5% (v/v) crop oil concentrate and an appropriate amount of water so that the final spray solutions contained 1.25+/−0.05% (v/v) crop oil concentrate.

For treatments comprised of technical compounds, weighed amounts can be placed individually in 25 mL glass vials and dissolved in a volume of 97:3 v/v acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of an appropriate amount of 1.5% (v/v) crop oil concentrate and an appropriate amount of water so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials can be placed individually in 25 mL glass vials and dissolved in a volume of 97:3 v/v acetone/DMSO to obtain 6× stock solutions, and measured amounts of the formulated compounds can be placed individually in 25 mL glass vials and diluted in a volume of 1.5% (v/v) crop oil concentrate or water to obtain 6× stock solutions. If a test compound does not dissolve readily, the mixture can be warmed and/or sonicated. Application solutions can be prepared by adding an appropriate amount of each stock solution (e.g., 2 mL) and diluted to the appropriate final concentrations with the addition of an appropriate amount of an aqueous mixture of 1.5% (v/v) crop oil concentrate so that the final spray solutions contained 1.25% (v/v) crop oil concentrate. When required, additional water and/or 97:3 v/v acetone/DMSO can be added to individual application solutions so that the final acetone and DMSO concentrations of the application solutions being compared are 16.2% and 0.5%, respectively.

All stock solutions and applications solutions were visually inspected for compound compatibility prior to application. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters (m$^2$) at a spray height of 18 to 20 inches (46 to 50 cm) above the average plant canopy height. Control plants were sprayed in the same manner with the solvent blank.

The treated plants and control plants were placed in a greenhouse as described above and watered by sub-irrigation to prevent wash-off of the test compounds. After approximately 2 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 40-41.

TABLE 40

Synergistic Activity of Foliar-Applied Compound A Acid and Quizalofop-p-ethyl Herbicidal Compositions on Control of Weeds Common to Row Crops Such as Corn and Soybean Cropping Systems.

| Compound A Acid | Quizalofop-p-ethyl | Visual Weed Control (%) - 14 DAA AVEFA | |
|---|---|---|---|
| gae/ha | gae/ha | Obs | Exp |
| 3.75 | 0 | 0 | — |
| 7.5 | 0 | 0 | — |
| 15 | 0 | 0 | — |
| 0 | 14.25 | 40 | — |
| 3.75 | 14.25 | 85 | 40 |
| 7.5 | 14.25 | 70 | 40 |
| 15 | 14.25 | 55 | 40 |

| Compound A Acid | Quizalofop-p-ethyl | Visual Weed Control (%) - 14 DAA LOLMU | |
|---|---|---|---|
| gae/ha | gae/ha | Obs | Exp |
| 3.75 | 0 | 0 | — |
| 7.5 | 0 | 10 | — |
| 15 | 0 | 10 | — |
| 0 | 3.56 | 0 | — |
| 0 | 7.125 | 60 | — |
| 3.75 | 3.56 | 50 | 0 |
| 7.5 | 3.56 | 30 | 10 |
| 15 | 3.56 | 40 | 10 |
| 3.75 | 7.125 | 70 | 60 |
| 7.5 | 7.125 | 80 | 64 |
| 15 | 7.125 | 70 | 64 |

TABLE 41

Synergistic Activity of Foliar-Applied Compound A Benzyl Ester and Quizalofop-p-ethyl Herbicidal Compositions on Weeds Common to Row Crops Such as Corn and Soybean Cropping Systems.

| Compound A Benzyl Ester | Quizalofop-p-ethyl | Visual Weed Control (%) - 14 DAA AVEFA | |
|---|---|---|---|
| gae/ha | gae/ha | Obs | Exp |
| 3.75 | 0 | 10 | — |
| 7.5 | 0 | 0 | — |
| 15 | 0 | 10 | — |
| 0 | 14.25 | 40 | — |
| 3.75 | 14.25 | 75 | 46 |
| 7.5 | 14.25 | 99 | 40 |
| 15 | 14.25 | 40 | 46 |

| Compound A Benzyl Ester | Quizalofop-p-ethyl | Visual Weed Control (%) - 14 DAA LOLMU | |
|---|---|---|---|
| gae/ha | gae/ha | Obs | Exp |
| 3.75 | 0 | 0 | — |
| 7.5 | 0 | 10 | — |
| 15 | 0 | 10 | — |
| 0 | 3.56 | 0 | — |
| 0 | 7.125 | 60 | — |
| 3.75 | 3.56 | 60 | 0 |
| 7.5 | 3.56 | 40 | 10 |
| 15 | 3.56 | 35 | 10 |
| 3.75 | 7.125 | 70 | 60 |
| 7.5 | 7.125 | 75 | 64 |
| 15 | 7.125 | 80 | 64 |

AVEFA  *Avena fatua* L.  oat, wild
LOLMU  *Lolium multiflorum* Lam.  ryegrass, Italian
gae/ha = grams acid equivalent per hectare
gai/ha = grams active ingredient per hectare
Obs = observed value
Exp = expected value as calculated by Colby's equation
DAA = days after application

Example IV

Evaluation of Postemergence Herbicidal Activity of Mixtures in Cereal Crops in the Greenhouse Seeds of the desired test plant species were planted in Sun Gro MetroMix 306 planting mixture, which typically has a pH of 6.0 to 6.8 and an organic matter content of about 30 percent, in plastic pots with a surface area of 103.2 square centimeters (cm²). When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and about 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of the benzyl ester of 4-amino-3-chloro-5-fluoro-6-(4-chloro-2-fluoro-3-methoxy-phenyl)pyridine-2-carboxylic acid (Compound A), formulated as an SC, a second cereal herbicide alone and then both in combination.

Forms of Compound a (Compound of Formula I) Tested Include:

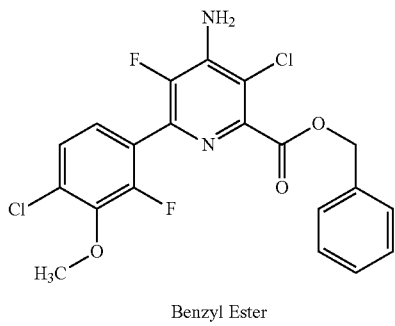

Compound A

Benzyl Ester

Other herbicidal components were applied on an active ingredient basis and included acetyl-CoA carboxylase (ACCase)-inhibiting herbicides clodinafop-propargyl, fenoxaprop-P-ethyl, pinoxaden and tralkoxydim.

Measured aliquots of benzyl ester of 4-amino-3-chloro-5-fluoro-6-(4-chloro-2-fluoro-3-methoxy-phenyl)pyridine-2-carboxylic acid (Compound A) were placed in 25 milliliter (mL) glass vials and diluted in a volume of 1.25% (v/v) Agri-Dex® crop oil concentrate to obtain stock solutions. Compound requirements are based upon a 12 mL application volume at a rate of 187 liters per hectare (L/ha). Spray solutions of the second cereal herbicide and experimental compound mixtures were prepared by adding the stock solutions to the appropriate amount of dilution solution to form 12 mL spray solution with active ingredients in two- and three-way combinations. Formulated compounds were applied to the plant material with an overhead Mandel track sprayer equipped with an 8002E nozzle calibrated to deliver 187 L/ha over an application area of 0.503 square meters ($m^2$) at a spray height of 18 inches (46 cm) above average plant canopy. Control plants were sprayed in the same manner with the solvent blank.

The treated plants and control plants were placed in a greenhouse as described above and watered by sub-irrigation to prevent wash-off of the test compounds. After 20-22 days, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 42-45.

TABLE 42

Synergistic Activity of Foliar-Applied Compound A Benzyl Ester and Clodinafop-propargyl Herbicidal Compositions on Weed Control in a Cereals Cropping System.

| Compound A Benzyl Ester | Clodinofop-propargyl | Visual Weed Control (%) - 21 DAA | | | |
|---|---|---|---|---|---|
| | | LOLMU | | KCHSC | |
| gai/ha | gai/ha | Obs | Exp | Obs | Exp |
| 5 | 0 | 0 | — | 20 | — |
| 10 | 0 | 0 | — | 30 | — |
| 0 | 15 | 60 | — | 0 | — |
| 0 | 30 | 48 | — | 10 | — |
| 5 | 15 | 60 | 60 | 70 | 20 |
| 10 | 15 | 65 | 60 | 80 | 30 |
| 5 | 30 | 73 | 48 | 70 | 28 |
| 10 | 30 | 78 | 48 | 80 | 37 |

| Compound A Benzyl Ester | Clodinofop-propargyl | Visual Weed Control (%) - 21 DAA | | | | | |
|---|---|---|---|---|---|---|---|
| | | PHAMI | | APESV | | ALOMY | |
| gai/ha | gai/ha | Obs | Exp | Obs | Exp | Obs | Exp |
| 5 | 0 | 0 | — | 0 | — | 0 | — |
| 10 | 0 | 0 | — | 0 | — | 0 | — |
| 0 | 15 | 48 | — | 15 | — | 80 | — |
| 0 | 30 | 55 | — | 68 | — | 82 | — |
| 5 | 15 | 73 | 48 | 55 | 15 | 90 | 80 |
| 10 | 15 | 73 | 48 | 55 | 15 | 88 | 80 |
| 5 | 30 | 55 | 55 | 78 | 68 | 94 | 82 |
| 10 | 30 | 45 | 55 | 80 | 68 | 87 | 82 |

TABLE 43

Synergistic Activity of Foliar-Applied Compound A Benzyl Ester and Fenoxaprop-P-ethyl Herbicidal Compositions on Weed Control in a Cereals Cropping System.

| Compound A Benzyl Ester | Fenoxaprop-P-ethyl | Visual Weed Control (%) - 21 DAA | | | | | |
|---|---|---|---|---|---|---|---|
| | | KCHSC | | PHAMI | | APESV | |
| gai/ha | gai/ha | Obs | Exp | Obs | Exp | Obs | Exp |
| 5 | 0 | 20 | — | 0 | — | 0 | — |
| 10 | 0 | 30 | — | 0 | — | 0 | — |
| 0 | 23 | 0 | — | 10 | — | 50 | — |
| 0 | 46 | 0 | — | 45 | — | 83 | — |
| 5 | 23 | 60 | 20 | 10 | 10 | 65 | 50 |
| 10 | 23 | 68 | 30 | 10 | 10 | 63 | 50 |
| 5 | 46 | 70 | 20 | 55 | 45 | 81 | 83 |
| 10 | 46 | 70 | 30 | 55 | 45 | 83 | 83 |

TABLE 44

Synergistic Activity of Foliar-Applied Compound A Benzyl Ester and Pinoxaden Herbicidal Compositions on Weed Control in a Cereals Cropping System.

| Compound A Benzyl Ester | Pinoxaden | Visual Weed Control (%) - 21 DAA | | | |
|---|---|---|---|---|---|
| | | KCHSC | | PHAMI | |
| gai/ha | gai/ha | Obs | Exp | Obs | Exp |
| 5 | 0 | 20 | — | 0 | — |
| 10 | 0 | 30 | — | 0 | — |
| 0 | 15 | 0 | — | 78 | — |
| 0 | 30 | 15 | — | 94 | — |

TABLE 44-continued

Synergistic Activity of Foliar-Applied Compound A
Benzyl Ester and Pinoxaden Herbicidal Compositions
on Weed Control in a Cereals Cropping System.

| Compound A Benzyl Ester | Pinoxaden | Visual Weed Control (%) - 21 DAA | | | |
|---|---|---|---|---|---|
| | | KCHSC | | PHAMI | |
| gai/ha | gai/ha | Obs | Exp | Obs | Exp |
| 5 | 15 | 75 | 20 | 88 | 78 |
| 10 | 15 | 75 | 30 | 87 | 78 |
| 5 | 30 | 75 | 32 | 94 | 94 |
| 10 | 30 | 78 | 41 | 94 | 94 |

TABLE 45

Synergistic Activity of Foliar-Applied Compound A
Benzyl Ester and Tralkoxydim Herbicidal Compositions
on Weed Control in a Cereals Cropping System.

| Compound A Benzyl Ester | Tralkoxydim | Visual Weed Control (%) - 21 DAA | | | | | |
|---|---|---|---|---|---|---|---|
| | | AVEFA | | LOLMU | | KCHSC | |
| gai/ha | gai/ha | Obs | Exp | Obs | Exp | Obs | Exp |
| 5 | 0 | 0 | — | 0 | — | 20 | — |
| 10 | 0 | 0 | — | 0 | — | 30 | — |
| 0 | 50 | 78 | — | 86 | — | 10 | — |
| 0 | 100 | 99 | — | 96 | — | 0 | — |
| 5 | 50 | 95 | 78 | 95 | 86 | 55 | 28 |
| 10 | 50 | 96 | 78 | 94 | 86 | 65 | 37 |
| 5 | 100 | 97 | 99 | 97 | 96 | 65 | 20 |
| 10 | 100 | 97 | 99 | 95 | 96 | 73 | 30 |

ALOMY *Alopecurus myosuroides* Huds. blackgrass
APESV *Apera spica-venti* (L.) Beauv. windgrass
AVEFA *Avena fatua* L. wild oat
KCHSC *Kochia scoparia* (L.) Schrad. kochia
LOLMU *Lolium multiflorum* Lam. ryegrass, Italian
PHAMI *Phalaris minor* Retz. Canarygrass, littleseed
gae/ha = grams acid equivalent per hectare
gai/ha = grams active ingredient per hectare
Obs = observed value
Exp = expected value as calculated by Colby's equation
DAA = days after application Example V Evaluation of Post-Emergence Herbicidal Activity of
Mixtures Applied Under Field Conditions to Seeded
Rice Multiple field trials were conducted under commercial grower field conditions in Tolima, Colombia; Thessaloniki, Greece; Bianze and Copiano, Italy; and Humphrey, Ark., USA. Trials sites were located in commercially grown fields of direct-seeded rice (*Oryza sativa*) using standard herbicide small plot research methodology. Plots varied from 2 to 3 meter (m)×5 to 8 m (width×length) with 4 replicates per treatment. The rice crop was grown using normal cultural practices for fertilization, seeding, watering, flooding and maintenance to ensure good growth of the crop and the weeds.

All treatments in the field trials were applied using a backpack compressed air/gas sprayer with flat fan nozzles (80° or 110°) calibrated to apply 187 to 300 L/ha spray volume at approximately 200-400 kPa nozzle pressure. Commercially available products of cyhalofop-butyl (Clincher 180EC, Clincher 200EC, and Clincher SF (285 gr ai/L EC)) were mixed in water at appropriate formulated product rates to achieve the desired rates based on a unit area of application (hectare) to achieve the desired rates as shown. Treatments were rate at 19 to 58 days after application (DAA) as compared to the untreated control plants. Visual weed control was scored on a scale of 0 to 100 percent where 0 corresponds to no injury and 100 corresponds to complete kill.

All treatment results, both for the single product and mixtures, are an average of 4 replicates. The trial sites had naturally occurring populations of weeds. The weed spectrum included, but was not limited to, rice flatsedge (*Cyperus iria*, CYPIR); smallflower umbrellaplant (*Cyperus difformis*, CYPDI), junglerice (*Echinochloa colona*, ECHCO), barnyardgrass (*Echinochloa crus-galli*, ECHCG); multiple *Echinochloa* species in the same field (ECHSS), grasslike fimbristylis (*Fimbristylis miliacea*, FIMMI); ricefield bulrush (*Schoenoplectus mucronatus*, SCPMU) and hemp *Sesbania* (*Sesbania exaltata*, SEBEX). All synergistic interactions were significant at the P>0.01 level.

Some of the compounds tested, application rates employed, plant species tested, and results are given in Tables 46-48.

TABLE 46

Synergistic Activity of Foliar-Applied Compound A Benzyl
Ester and Cyhalofop-butyl Herbicidal Compositions on Weed
Control in a Rice Cropping System when evaluated 19 DAA
(Days After Application) in Tolima, Colombia.

| Compound A Benzyl Ester | Cyhal-ofop-butyl | Visual Weed Control (%) - 19 DAA | | | | | |
|---|---|---|---|---|---|---|---|
| | | CYPIR | | ECHCO | | FIMMI | |
| gae/ha | gai/ha | Obs | Exp | Obs | Exp | Obs | Exp |
| 12 | 0 | 69 | — | 76 | — | — | — |
| 0 | 280 | 0 | — | 0 | — | — | — |
| 12 | 280 | 85 | 69 | 90 | 76 | — | — |
| 24 | 0 | — | — | — | — | 39 | — |
| 0 | 190 | — | — | — | — | 16 | — |
| 24 | 190 | — | — | — | — | 63 | 48 |

TABLE 47

Synergistic Activity of Foliar-Applied Compound A Benzyl
Ester and Cyhalofop-butyl Herbicidal Compositions on Weed
Control in a Rice Cropping System when evaluated 7 DAA (Days
After Application) in Humphrey, Arkansas, USA.

| Compound A Benzyl Ester | Cyhalofop-butyl | Visual Weed Control (%) - 7 DAA SEBEX | |
|---|---|---|---|
| gaeha | gai/ha | Obs | Exp |
| 24 | 0 | 80 | — |
| 0 | 280 | 0 | — |
| 24 | 280 | 90 | 80 |
| 32 | 0 | 78 | — |

TABLE 47-continued

Synergistic Activity of Foliar-Applied Compound A Benzyl Ester and Cyhalofop-butyl Herbicidal Compositions on Weed Control in a Rice Cropping System when evaluated 7 DAA (Days After Application) in Humphrey, Arkansas, USA.

| Compound A Benzyl Ester | Cyhalofop-butyl | Visual Weed Control (%) - 7 DAA SEBEX | |
|---|---|---|---|
| gaeha | gai/ha | Obs | Exp |
| 0 | 280 | 0 | — |
| 32 | 280 | 93 | 78 |

TABLE 48

Synergistic Activity of Foliar-Applied Compound A Benzyl Ester and Cyhalofop-butyl Herbicidal Compositions on Weed Control in a Rice Cropping System when evaluated 55 to 58 DAA (Days After Application) in Greece (CYPDI and ECHCG) and Italy (ECHSS and SCPMU).

| Compound A Benzyl Ester gae/ha | Cyhalofop-butyl gai/ha | Visual Weed Control (%) - 55-58 DAA | | | | | | | |
|---|---|---|---|---|---|---|---|---|---|
| | | CYPDI | | ECHCG | | ECHSS | | SCPMU | |
| | | Obs | Exp | Obs | Exp | Obs | Exp | Obs | Exp |
| 24 | 0 | 81 | — | 6 | — | 40 | — | 27 | — |
| 0 | 300 | 0 | — | 29 | — | 37 | — | 6 | — |
| 24 | 300 | 90 | 81 | 60 | 33 | 89 | 62 | 56 | 27 |

Example V

Evaluation of Postemergence Foliar-Applied Ternary Herbicidal Mixtures for Weed Control in Direct Seeded Rice Seeds or nutlets of the desired test plant species were planted in a soil matrix prepared by mixing a sandy loam or loam soil (e.g., 32 percent silt, 23 percent clay, and 45 percent sand, with a pH of about 6.5 and an organic matter content of about 1.9 percent) and calcareous grit in an 80 to 20 ratio. The soil matrix was contained in plastic pots with a volume of 1 quart and a surface area of 83.6 square centimeters (cm²). When required to ensure good germination and healthy plants, a fungicide treatment and/or other chemical or physical treatment was applied. The plants were grown for 8-22 days in a greenhouse with an approximate 14 hr photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the benzyl ester of 4-amino-3-chloro-5-fluoro-6-(4-chloro-2-fluoro-3-methoxy-phenyl) pyridine-2-carboxylic acid (Compound A), formulated as an SC (suspension concentrate), an ACCase inhibitor, and a third herbicidal component, each applied alone and in ternary combination. Forms of compound A were applied on an acid equivalent basis.

Forms of Compound a (Compound of Formula I) Tested Include:

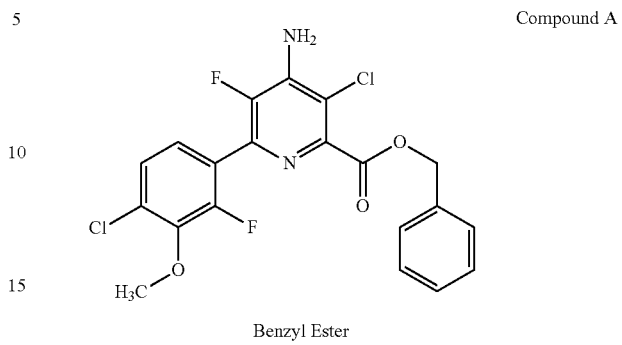

Compound A

Benzyl Ester

The ACCase inhibitor component was applied on an active ingredient basis and included cyhalofop-R-butyl formulated as Clincher® SF, fenoxaprop-p-ethyl formulated as RiceStar® HT, and profoxydim formulated as Aura® 20EC. Other herbicidal components were applied on an active ingredient or acid equivalent basis depending on the compound and included penoxsulam formulated as Grasp® SC, bentazon sodium formulated as Basagran triclopyr trimethylammonium (TEA) salt formulated as Grandstand® R, bispyribac sodium formulated as Regiment® 80WP, imazamox ammonium formulated as Beyond®, benzobicyclon, quinclorac formulated as Facet® 75DF, glyphosate dimethylammonium (DMA) salt formulated as Durango® DMA, glufosinate ammonium formulated as Ignite® 280, fentrazamide formulated as an emulsifiable concentrate (EC), propyrisulfuron formulated as Zeta One®, and indanofan (technical grade material).

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrate to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 9 mL of an aqueous mixture of 1.25% (v/v) crop oil concentrate so that the final spray solutions contained 1.25% (v/v) crop oil concentrate.

For treatments comprised of formulated and technical compounds, weighed amounts of the technical materials were placed individually in 25 mL glass vials and dissolved in a volume of 97:3 v/v acetone/DMSO to obtain 12× stock solutions, and measured amounts of the formulated compounds were placed individually in 25 mL glass vials and diluted in a volume of 1.5% (v/v) crop oil concentrate to obtain 12× stock solutions. If a test compound does not dissolve readily, the mixture was warmed and/or sonicated. Application solutions were prepared by adding an appropriate amount of each stock solution (e.g., 1 mL) and diluted to the appropriate final concentrations with the addition of an appropriate amount of an aqueous mixture of 1.5% (v/v) crop oil concentrate so that the final spray solutions contained 1.25% (v/v) crop oil concentrate. As required, additional water and/or 97:3 v/v acetone/DMSO was added to individual application solutions so that the final acetone and DMSO concentrations of the application solutions being compared were 8.1% and 0.25%, respectively.

All stock solutions and applications solutions were visually inspected for compound compatibility prior to application. Spray solutions were applied to the plant material with an overhead Mandel track sprayer equipped with a 8002E nozzles calibrated to deliver 187 L/ha over an application area of 0.503 m² at a spray height of 18 inches (46 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing three active ingredients, A, B, and C:

$$\text{Expected} = A+B+C-((A \times B+A \times C+B \times C)/100)+(A \times B \times C/10000)$$

A=observed efficacy of active ingredient A at the same concentration as used in the mixture.

B=observed efficacy of active ingredient B at the same concentration as used in the mixture.

C=observed efficacy of active ingredient C at the same concentration as used in the mixture.

The compounds tested, application rates employed, plant species tested, and results are given in Tables 49-62.

TABLE 49

Synergistic Activity of Foliar-Applied Compound A Benzyl Ester, Cyhalofop-Butyl, and Penoxsulam Ternary Herbicidal Compositions on Weed Control in a Rice Cropping System.

| Compound A Benzyl Ester | Cyhalofop-butyl | Penoxsulam | Visual Weed Control (%) - 21 DAA IPOHE | |
|---|---|---|---|---|
| gae/ha | gai/ha | gai/ha | Obs | Exp |
| 8 | 0 | 0 | 15 | — |
| 16 | 0 | 0 | 33 | — |
| 0 | 35 | 0 | 0 | — |
| 0 | 0 | 8.75 | 48 | — |
| 8 | 35 | 8.75 | 62 | 56 |
| 16 | 35 | 8.75 | 90 | 66 |

TABLE 50

Synergistic Activity of Foliar-Applied Compound A Benzyl Ester, Cyhalofop-Butyl, and Bentazon Ternary Herbicidal Compositions on Weed Control in a Rice Cropping System.

| Compound A Benzyl Ester | Cyhalofop-butyl | Bentazon sodium | Visual Weed Control (%) - 21 DAA IPOHE | |
|---|---|---|---|---|
| gae/ha | gai/ha | gae/ha | Obs | Exp |
| 2.19 | 0 | 0 | 30 | — |
| 4.38 | 0 | 0 | 38 | — |
| 0 | 35 | 0 | 0 | — |
| 0 | 0 | 420 | 53 | — |
| 2.19 | 35 | 420 | 70 | 67 |
| 4.38 | 35 | 420 | 82 | 71 |
| 8 | 0 | 0 | 15 | — |
| 16 | 0 | 0 | 33 | — |
| 0 | 35 | 0 | 0 | — |
| 0 | 0 | 420 | 75 | — |
| 8 | 35 | 420 | 85 | 79 |
| 16 | 35 | 420 | 93 | 83 |

TABLE 51

Synergistic Activity of Foliar-Applied Compound A Benzyl Ester, Cyhalofop-Butyl, and Triclopyr TEA Salt Ternary Herbicidal Compositions on Weed Control in a Rice Cropping System.

| Compound A Benzyl Ester | Cyhalofop-butyl | Triclopyr TEA Salt | Visual Weed Control (%) - 21 DAA | | | | | |
|---|---|---|---|---|---|---|---|---|
| | | | ECHCG | | ECHCO | | SCPJU | |
| gae/ha | gai/ha | gae/ha | Obs | Exp | Obs | Exp | Obs | Exp |
| 2.19 | 0 | 0 | 5 | — | 10 | — | 65 | — |
| 4.38 | 0 | 0 | 27 | — | 25 | — | 96 | — |
| 0 | 35 | 0 | 20 | — | 37 | — | 0 | — |
| 0 | 0 | 17.5 | 0 | — | 3 | — | 43 | — |
| 2.19 | 35 | 17.5 | 35 | 24 | 45 | 45 | 98 | 80 |
| 4.38 | 35 | 17.5 | 37 | 41 | 90 | 54 | 100 | 98 |

| Compound A Benzyl Ester | Cyhalofop-butyl | Triclopyr TEA Salt | Visual Weed Control (%) - 21 DAA CYPIR | |
|---|---|---|---|---|
| gae/ha | gai/ha | gae/ha | Obs | Exp |
| 8 | 0 | 0 | 53 | — |
| 16 | 0 | 0 | 95 | — |
| 0 | 35 | 0 | 0 | — |
| 0 | 0 | 17.5 | 0 | — |
| 8 | 35 | 17.5 | 100 | 53 |
| 16 | 35 | 17.5 | 100 | 95 |

TABLE 52

Synergistic Activity of Foliar-Applied Compound A Benzyl Ester, Cyhalofop-Butyl, and Bispyribac Sodium Ternary Herbicidal Compositions on Weed Control in a Rice Cropping System.

| Compound A Benzyl Ester | Cyhalofop-butyl | Bispyribac sodium | Visual Weed Control (%) - 21 DAA | | | |
|---|---|---|---|---|---|---|
| | | | IPOHE | | CYPES | |
| gae/ha | gai/ha | gai/ha | Obs | Exp | Obs | Exp |
| 8 | 0 | 0 | 10 | — | 70 | — |
| 0 | 35 | 0 | 0 | — | 0 | — |

TABLE 52-continued

Synergistic Activity of Foliar-Applied Compound A Benzyl Ester, Cyhalofop-Butyl, and Bispyribac Sodium Ternary Herbicidal Compositions on Weed Control in a Rice Cropping System.

| Compound A Benzyl Ester | Cyhalofop-butyl | Bispyribac sodium | Visual Weed Control (%) - 21 DAA | | | |
|---|---|---|---|---|---|---|
| | | | IPOHE | | CYPES | |
| gae/ha | gai/ha | gai/ha | Obs | Exp | Obs | Exp |
| 0 | 0 | 28 | 60 | — | 20 | — |
| 8 | 35 | 28 | 83 | 64 | 90 | 76 |

TABLE 53

Synergistic Activity of Foliar-Applied Compound A Benzyl Ester, Cyhalofop-Butyl, and Imazamox Ammonium Ternary Herbicidal Compositions on Weed Control in a Rice Cropping System.

| Compound A Benzyl Ester | Cyhalofop-butyl | Imazamox ammonium | Visual Weed Control (%) - 21 DAA CYPES | |
|---|---|---|---|---|
| gae/ha | gai/ha | gai/ha | Obs | Exp |
| 8 | 0 | 0 | 70 | |
| 0 | 35 | 0 | 0 | |
| 0 | 0 | 12 | 60 | |
| 8 | 35 | 12 | 95 | 88 |

| Compound A Benzyl Ester | Cyhalofop-butyl | Imazamox ammonium | Visual Weed Control (%) - 21 DAA IPOHE | |
|---|---|---|---|---|
| gae/ha | gai/ha | gae/ha | Obs | Exp |
| 8 | 0 | 0 | 20 | — |
| 0 | 17.5 | 0 | 0 | — |
| 0 | 0 | 6 | 65 | — |
| 8 | 17.5 | 6 | 85 | 72 |

TABLE 54

Synergistic Activity of Foliar-Applied Compound A Benzyl Ester, Cyhalofop-Butyl, and Benzobicyclon Ternary Herbicidal Compositions on Weed Control in a Rice Cropping System.

| Compound A Benzyl Ester | Cyhalofop-butyl | Benzobicyclon | Visual Weed Control (%) - 21 DAA ECHCG | |
|---|---|---|---|---|
| gae/ha | gai/ha | gai/ha | Obs | Exp |
| 8 | 0 | 0 | 38 | — |
| 0 | 35 | 0 | 20 | — |
| 0 | 0 | 200 | 0 | — |
| 8 | 35 | 200 | 90 | 50 |

| Compound A Benzyl Ester | Cyhalofop-butyl | Benzobicyclon | Visual Weed Control (%) - 21 DAA IPOHE | |
|---|---|---|---|---|
| gae/ha | gai/ha | gai/ha | Obs | Exp |
| 8 | 0 | 0 | 10 | — |
| 16 | 0 | 0 | 30 | — |
| 0 | 35 | 0 | 0 | — |
| 0 | 0 | 200 | 55 | — |

TABLE 54-continued

Synergistic Activity of Foliar-Applied Compound A Benzyl Ester, Cyhalofop-Butyl, and Benzobicyclon Ternary Herbicidal Compositions on Weed Control in a Rice Cropping System.

| 8 | 35 | 200 | 78 | 60 |
| 16 | 35 | 200 | 85 | 69 |

TABLE 55

Synergistic Activity of Foliar-Applied Compound A Benzyl Ester, Cyhalofop-Butyl, and Quinclorac Ternary Herbicidal Compositions on Weed Control in a Rice Cropping System.

| Compound A Benzyl Ester | Cyhalofop-butyl | Quinclorac | Visual Weed Control (%) - 21 DAA | | | |
|---|---|---|---|---|---|---|
| | | | ECHCG | | CYPES | |
| gae/ha | gai/ha | gai/ha | Obs | Exp | Obs | Exp |
| 8 | 0 | 0 | 38 | — | 70 | — |
| 0 | 35 | 0 | 20 | — | 0 | — |
| 0 | 0 | 280 | 10 | — | 0 | — |
| 8 | 35 | 280 | 92 | 55 | 85 | 70 |

TABLE 56

Synergistic Activity of Foliar-Applied Compound A Benzyl Ester, Cyhalofop-Butyl, and Glyphosate Dimethylammonium (DMA) Salt Ternary Herbicidal Compositions on Weed Control in a Rice Cropping System.

| Compound A Benzyl Ester | Cyhalofop-butyl | Glyphosate DMA | Visual Weed Control (%) - 21 DAA LEFCH | |
|---|---|---|---|---|
| gae/ha | gai/ha | gai/ha | Obs | Exp |
| 16 | 0 | 0 | 25 | — |
| 0 | 35 | 0 | 68 | — |
| 0 | 0 | 420 | 45 | — |
| 16 | 35 | 420 | 93 | 87 |

| Compound A Benzyl Ester | Cyhalofop-butyl | Glyphosate DMA | Visual Weed Control (%) - 21 DAA ECHCG | |
|---|---|---|---|---|
| gae/ha | gai/ha | gae/ha | Obs | Exp |
| 8 | 0 | 0 | 45 | — |
| 0 | 17.5 | 0 | 33 | — |
| 0 | 0 | 105 | 23 | — |
| 8 | 17.5 | 105 | 83 | 71 |

TABLE 57

Synergistic Activity of Foliar-Applied Compound A Benzyl Ester, Cyhalofop-Butyl, and Glufosinate Ammonium Ternary Herbicidal Compositions on Weed Control in a Rice Cropping System.

| Compound A Benzyl Ester | Cyhalofop-butyl | Glufosinate ammonium | Visual Weed Control (%) - 21 DAA ECHCO | |
|---|---|---|---|---|
| gae/ha | gai/ha | gai/ha | Obs | Exp |
| 8 | 0 | 0 | 45 | — |
| 0 | 35 | 0 | 40 | — |

TABLE 57-continued

Synergistic Activity of Foliar-Applied Compound A Benzyl Ester, Cyhalofop-Butyl, and Glufosinate Ammonium Ternary Herbicidal Compositions on Weed Control in a Rice Cropping System.

| Compound A Benzyl Ester | Cyhalofop-butyl | Glufosinate ammonium | Visual Weed Control (%) - 21 DAA ECHCO | |
|---|---|---|---|---|
| gae/ha | gai/ha | gai/ha | Obs | Exp |
| 0 | 0 | 115 | 0 | — |
| 8 | 35 | 115 | 80 | 67 |

TABLE 58

Synergistic Activity of Foliar-Applied Compound A Benzyl Ester, Cyhalofop-Butyl, and Fentrazamide Ternary Herbicidal Compositions on Weed Control in a Rice Cropping System.

| Compound A Benzyl Ester | Cyhalofop-butyl | Fentrazamide | Visual Weed Control (%) - 22 DAA | | | |
|---|---|---|---|---|---|---|
| | | | ECHCG | | ECHOR | |
| gae/ha | gai/ha | gai/ha | Obs | Exp | Obs | Exp |
| 8 | 0 | 0 | 40 | — | 13 | — |
| 16 | 0 | 0 | 58 | — | 40 | — |
| 0 | 17.5 | 0 | 0 | — | 0 | — |
| 0 | 35 | 0 | 12 | — | 15 | — |
| 0 | 0 | 33.75 | 0 | — | 3 | — |
| 0 | 0 | 67.5 | 0 | — | 0 | — |
| 8 | 17.5 | 33.75 | 40 | 40 | 25 | 16 |
| 8 | 17.5 | 67.5 | 67 | 40 | 52 | 13 |
| 8 | 35 | 33.75 | 48 | 47 | 63 | 29 |
| 8 | 35 | 67.5 | 65 | 47 | 55 | 26 |
| 16 | 17.5 | 33.75 | 83 | 58 | 60 | 42 |
| 16 | 17.5 | 67.5 | 80 | 58 | 82 | 40 |
| 16 | 35 | 33.75 | 92 | 63 | 80 | 51 |
| 16 | 35 | 67.5 | 87 | 63 | 87 | 49 |

TABLE 59

Synergistic Activity of Foliar-Applied Compound A Benzyl Ester, Cyhalofop-Butyl, and Propyrisulfuron Ternary Herbicidal Compositions on Weed Control in a Rice Cropping System.

| Compound A Benzyl Ester | Cyhalofop-butyl | Propyrisulfuron | Visual Weed Control (%) - 22 DAA ECHOR | |
|---|---|---|---|---|
| gae/ha | gai/ha | gai/ha | Obs | Exp |
| 8 | 0 | 0 | 13 | — |
| 0 | 35 | 0 | 15 | — |
| 0 | 0 | 22.5 | 55 | — |
| 8 | 35 | 22.5 | 78 | 67 |

TABLE 60

Synergistic Activity of Foliar-Applied Compound A Benzyl Ester, Fenoxaprop-p-Ethyl + Isoxadifen-ethyl, and Penoxsulam Ternary Herbicidal Compositions on Weed Control in a Rice Cropping System.

| Compound A Benzyl Ester | Penoxsulam | Fenoxaprop-p-ethyl + Isoxadifen-ethyl | Visual Weed Control (%) - 22 DAA ECHOR | |
|---|---|---|---|---|
| gae/ha | gai/ha | gai/ha | Obs | Exp |
| 8 | 0 | 0 | 25 | — |
| 16 | 0 | 0 | 35 | — |
| 0 | 4.38 | 0 | 45 | — |
| 0 | 8.75 | 0 | 53 | — |
| 0 | 0 | 4.38 | 0 | — |
| 8 | 4.38 | 4.38 | 73 | 59 |
| 8 | 8.75 | 4.38 | 62 | 65 |
| 16 | 4.38 | 4.38 | 82 | 64 |
| 16 | 8.75 | 4.38 | 87 | 70 |

| Compound A Benzyl Ester | Penoxsulam | Fenoxaprop-p-ethyl + Isoxadifen-ethyl | Visual Weed Control (%) - 22 DAA CYPIR | |
|---|---|---|---|---|
| gae/ha | gai/ha | gai/ha | Obs | Exp |
| 8 | 0 | 0 | 37 | — |
| 0 | 4.38 | 0 | 50 | — |
| 0 | 0 | 4.38 | 0 | — |
| 0 | 0 | 8.75 | 0 | — |
| 8 | 4.38 | 4.38 | 83 | 68 |
| 8 | 4.38 | 8.75 | 88 | 68 |

TABLE 61

Synergistic Activity of Foliar-Applied Compound A Benzyl Ester, Profoxydim, and Penoxsulam Ternary Herbicidal Compositions on Weed Control in a Rice Cropping System.

| Compound A Benzyl Ester | Penoxsulam | Profoxydim | Visual Weed Control (%) - 22 DAA ECHOR | |
|---|---|---|---|---|
| gae/ha | gai/ha | gai/ha | Obs | Exp |
| 8 | 0 | 0 | 25 | — |
| 16 | 0 | 0 | 35 | — |
| 0 | 4.38 | 0 | 45 | — |
| 0 | 0 | 3.12 | 0 | — |
| 8 | 4.38 | 3.12 | 73 | 59 |
| 16 | 4.38 | 3.12 | 70 | 64 |

| Compound A Benzyl Ester | Penoxsulam | Profoxydim | Visual Weed Control (%) - 22 DAA CYPIR | |
|---|---|---|---|---|
| gae/ha | gai/ha | gai/ha | Obs | Exp |
| 8 | 0 | 0 | 37 | — |
| 0 | 4.38 | 0 | 50 | — |
| 0 | 0 | 3.12 | 0 | — |
| 0 | 0 | 6.25 | 0 | — |
| 8 | 4.38 | 3.12 | 87 | 68 |
| 8 | 4.38 | 6.25 | 87 | 68 |

TABLE 62

Synergistic Activity of Foliar-Applied Compound A Benzyl Ester, Cyhalofop-butyl, and Indanofan Ternary Herbicidal Compositions on Weed Control in a Rice Cropping System.

| Compound A Benzyl Ester | Cyhalofop-butyl | Indanofan | Visual Weed Control (%) - 22 DAA LEFCH | |
|---|---|---|---|---|
| gae/ha | gai/ha | gai/ha | Obs | Exp |
| 8 | 0 | 0 | 28 | — |
| 0 | 35 | 0 | 70 | — |
| 0 | 0 | 72.5 | 30 | — |
| 0 | 0 | 145 | 38 | — |
| 8 | 35 | 72.5 | 95 | 85 |
| 8 | 35 | 145 | 98 | 86 |

CYPES  *Cyperus esculentus* L.                         nutsedge, yellow
CYPIR  *Cyperus iria* L.                              flatsedge, rice
ECHCG  *Echinochloa crusgalli* (L.) Beauv.            barnyardgrass
ECHCO  *Echinochloa colona* (L.) Link                 junglerice
ECHOR  *Echinochloa oryzoides* (Ard.) Fritsch         early watergrass
IPOHE  *Ipomoea hederacea* Jacq.                      morningglory, ivyleaf
LEFCH  *Leptochloa chinensis* (L.) Nees               sprangletop, Chinese
SCPJU  *Schoenoplectus juncoides* (Roxb.) Palla       bulrush, Japanese
gae/ha = grams acid equivalent per hectare
gai/ha = grams active ingredient per hectare
Obs = observed value
Exp = expected value as calculated by Colby's equation
DAA = days after application

Example VI

Evaluation of In-Water Applied Ternary Herbicidal Mixtures for Weed Control in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters ($cm^2$) leaving a headspace of 3 centimeters (cm) in each pot. Mud was allowed to dry overnight prior to planting or transplanting. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 860 mL of mud contained in 32-oz. non-perforated plastic pots with a surface area of 86.59 $cm^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 hr photoperiod which was maintained at about 29'C during the day and 26° C. during the night. Nutrients were added as Osmocote® (19:6:12, N:P:K+minor nutrients) at 2 g per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the benzyl ester of 4-amino-3-chloro-5-fluoro-6-(4-chloro-2-fluoro-3-methoxy-phenyl) pyridine-2-carboxylic acid (Compound A), formulated as an SC (suspension concentrate), an ACCase inhibitor herbicide, and a third herbicidal component, each applied alone and in ternary combination. Forms of compound A were applied on an acid equivalent basis.

Forms of Compound a (Compound of Formula I) Tested Include:

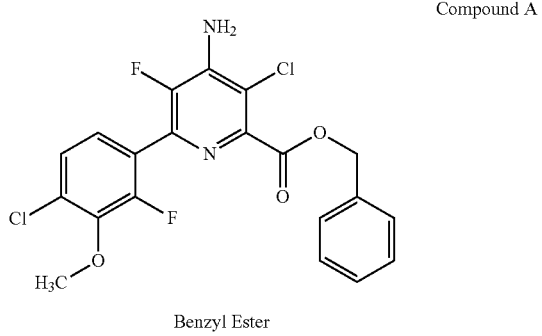 [SMILES: COc1c(Cl)ccc(-c2nc(C(=O)OCc3ccccc3)c(Cl)c(N)c2F)c1F]

Compound A

Benzyl Ester

The ACCase inhibitor component was applied on an active ingredient basis and included cyhalofop-R-butyl formulated as Clincher® G and metamifop formulated as Metamifop EC. Other herbicidal components were applied on an active ingredient or acid equivalent basis depending on the compound and included penoxsulam formulated as Grasp® SC, bentazon sodium formulated as Basagran®, triclopyr trimethylammonium (TEA) salt formulated as Grandstand® R, benzobicyclon formulated as Benzobicyclon, benfuresate formulated as Full Slot® WG, pyraclonil formulated as Pyraclon® Flowable, mefenacet (technical grade material), and pretilachlor (technical grade material).

Treatment requirements for each compound or herbicidal component were calculated based upon the rates being tested, the concentration of active ingredient or acid equivalent in the formulation, an application volume of 1 mL per component per pot, and an application area of 86.59 $cm^2$ per pot.

For formulated compounds, a measured amount was placed in an individual 100 or 200 mL glass vial and was dissolved in a volume of 1.25% (v/v) Agri-Dex® crop oil concentrate to obtain application solutions. If the test compound did not dissolve readily, the mixture was warmed and/or sonicated.

For technical grade compounds, a weighed amount was placed in an individual 100 to 200 mL glass vial and was dissolved in a volume of acetone to obtain concentrated stock solutions. If the test compound did not dissolve readily, the mixture was warmed and/or sonicated. The concentrated stock solutions obtained were diluted with an equivalent volume of an aqueous mixture containing 2.5% (v/v) oil concentrate so that the final application solutions contained 1.25% (v/v) crop oil concentrate.

Applications were made by injecting with a pipetter appropriate amounts of the application solutions, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing three active ingredients, A, B, and C:

$$\text{Expected} = A+B+C-((A \times B+A \times C+B \times C)/100)+(A \times B \times C/10000)$$

A=observed efficacy of active ingredient A at the same concentration as used in the mixture.

B=observed efficacy of active ingredient B at the same concentration as used in the mixture.

C=observed efficacy of active ingredient C at the same concentration as used in the mixture.

The compounds tested, application rates employed, plant species tested, and results are given in Tables 63-71.

TABLE 63

Synergistic Activity of In-Water Applications of Compound A Benzyl Ester, Cyhalofop-butyl, and Penoxsulam Ternary Herbicidal Compositions on Weed Control in a Rice Cropping System.

| Compound A Benzyl Ester | Cyhalofop-butyl | Penoxsulam | Visual Weed Control (%) - 21 DAA | | | |
|---|---|---|---|---|---|---|
| | | | FIMMI | | ECHCG | |
| gae/ha | gai/ha | gai/ha | Obs | Exp | Obs | Exp |
| 1.09 | 0 | 0 | 8 | — | 0 | — |
| 2.19 | 0 | 0 | 33 | — | 7 | — |
| 0 | 22.5 | 0 | 33 | — | 0 | — |
| 0 | 45 | 0 | 0 | — | 3 | — |
| 0 | 0 | 1.25 | 33 | — | 17 | — |
| 1.09 | 22.5 | 1.25 | 70 | 59 | 28 | 17 |
| 2.19 | 22.5 | 1.25 | 95 | 70 | 58 | 22 |
| 1.09 | 45 | 1.25 | 65 | 39 | 45 | 19 |
| 2.19 | 45 | 1.25 | 87 | 56 | 87 | 25 |

| Compound A Benzyl Ester | Cyhalofop-butyl | Penoxsulam | Visual Weed Control (%) - 21 DAA ECHCG | |
|---|---|---|---|---|
| gae/ha | gai/ha | gai/ha | Obs | Exp |
| 4 | 0 | 0 | 25 | — |
| 8 | 0 | 0 | 45 | — |
| 16 | 0 | 0 | 99 | — |
| 0 | 45 | 0 | 30 | — |
| 0 | 0 | 2.5 | 55 | — |
| 4 | 45 | 2.5 | 85 | 76 |
| 8 | 45 | 2.5 | 100 | 83 |
| 16 | 45 | 2.5 | 100 | 100 |

| Compound A Benzyl Ester | Cyhalofop-butyl | Penoxsulam | Visual Weed Control (%) - 21 DAA CYPRO | |
|---|---|---|---|---|
| gae/ha | gai/ha | gai/ha | Obs | Exp |
| 2.19 | 0 | 0 | 0 | — |
| 0 | 22.5 | 0 | 0 | — |
| 0 | 45 | 0 | 0 | — |
| 0 | 0 | 1.25 | 0 | — |

TABLE 63-continued

Synergistic Activity of In-Water Applications of Compound A Benzyl Ester, Cyhalofop-butyl, and Penoxsulam Ternary Herbicidal Compositions on Weed Control in a Rice Cropping System.

| | | | | |
|---|---|---|---|---|
| 2.19 | 22.5 | 1.25 | 23 | 0 |
| 2.19 | 45 | 1.25 | 28 | 0 |

| Compound A Benzyl Ester | Cyhalofop-butyl | Penoxsulam | Visual Weed Control (%) - 24 DAA CYPRO | |
|---|---|---|---|---|
| gae/ha | gai/ha | gai/ha | Obs | Exp |
| 4 | 0 | 0 | 40 | — |
| 8 | 0 | 0 | 60 | — |
| 16 | 0 | 0 | 85 | — |
| 0 | 90 | 0 | 0 | — |
| 0 | 180 | 0 | 0 | — |
| 0 | 0 | 2.5 | 0 | — |
| 0 | 0 | 5 | 0 | — |
| 4 | 90 | 2.5 | 60 | 40 |
| 8 | 90 | 2.5 | 55 | 60 |
| 16 | 90 | 2.5 | 90 | 85 |
| 4 | 90 | 5 | 68 | 40 |
| 8 | 90 | 5 | 90 | 60 |
| 16 | 90 | 5 | 85 | 85 |
| 4 | 180 | 2.5 | 60 | 40 |
| 8 | 180 | 2.5 | 90 | 60 |
| 16 | 180 | 2.5 | 100 | 85 |
| 4 | 180 | 5 | 50 | 40 |
| 8 | 180 | 5 | 95 | 60 |
| 16 | 180 | 5 | 100 | 85 |

| Compound A Benzyl Ester | Cyhalofop-butyl | Penoxsulam | Visual Weed Control (%) - 24 DAA FIMMI | |
|---|---|---|---|---|
| gae/ha | gai/ha | gai/ha | Obs | Exp |
| 4 | 0 | 0 | 0 | — |
| 8 | 0 | 0 | 50 | — |
| 16 | 0 | 0 | 30 | — |
| 0 | 90 | 0 | 0 | — |
| 0 | 180 | 0 | 20 | — |
| 0 | 0 | 2.5 | 60 | — |
| 4 | 90 | 2.5 | 78 | 60 |
| 8 | 90 | 2.5 | 95 | 80 |
| 16 | 90 | 2.5 | 100 | 72 |
| 4 | 180 | 2.5 | 90 | 68 |
| 8 | 180 | 2.5 | 80 | 84 |
| 16 | 180 | 2.5 | 99 | 78 |

| Compound A Benzyl Ester | Cyhalofop-butyl | Penoxsulam | Visual Weed Control (%) - 24 DAA SCPMA | |
|---|---|---|---|---|
| gae/ha | gai/ha | gai/ha | Obs | Exp |
| 4 | 0 | 0 | 0 | — |
| 8 | 0 | 0 | 0 | — |
| 16 | 0 | 0 | 0 | — |
| 0 | 180 | 0 | 0 | — |
| 0 | 0 | 5 | 30 | — |
| 4 | 180 | 5 | 25 | 30 |
| 8 | 180 | 5 | 70 | 30 |
| 16 | 180 | 5 | 80 | 30 |

TABLE 64

Synergistic Activity of In-Water Applications of Compound A Benzyl Ester, Cyhalofop-butyl, and Bentazon Sodium Ternary Herbicidal Compositions on Weed Control in a Rice Cropping System.

| Compound A Benzyl Ester | Cyhalofop-butyl | Bentazon Sodium | Visual Weed Control (%) - 21 DAA ECHCG | |
| --- | --- | --- | --- | --- |
| gae/ha | gai/ha | gae/ha | Obs | Exp |
| 1.09 | 0 | 0 | 0 | — |
| 2.19 | 0 | 0 | 7 | — |
| 0 | 22.5 | 0 | 0 | — |
| 0 | 45 | 0 | 3 | — |
| 0 | 0 | 210 | 0 | — |
| 1.09 | 22.5 | 210 | 20 | 0 |
| 2.19 | 22.5 | 210 | 17 | 7 |
| 1.09 | 45 | 210 | 13 | 3 |
| 2.19 | 45 | 210 | 72 | 10 |
| 4 | 0 | 0 | 25 | — |
| 8 | 0 | 0 | 45 | — |
| 16 | 0 | 0 | 99 | — |
| 0 | 45 | 0 | 30 | — |
| 0 | 0 | 420 | 15 | — |
| 4 | 45 | 420 | 85 | 55 |
| 8 | 45 | 420 | 100 | 67 |
| 16 | 45 | 420 | 100 | 99 |

| Compound A Benzyl Ester | Cyhalofop-butyl | Bentazon Sodium | Visual Weed Control (%) - 21 DAA FIMMI | |
| --- | --- | --- | --- | --- |
| gae/ha | gai/ha | gae/ha | Obs | Exp |
| 1.09 | 0 | 0 | 8 | — |
| 2.19 | 0 | 0 | 33 | — |
| 0 | 45 | 0 | 0 | — |
| 0 | 0 | 210 | 17 | — |
| 1.09 | 45 | 210 | 33 | 24 |
| 2.19 | 45 | 210 | 68 | 44 |
| 4 | 0 | 0 | 62 | — |
| 0 | 22.5 | 0 | 0 | — |
| 0 | 45 | 0 | 0 | — |
| 0 | 0 | 420 | 30 | — |
| 4 | 22.5 | 420 | 93 | 73 |
| 4 | 45 | 420 | 100 | 73 |

TABLE 65

Synergistic Activity of In-Water Applications of Compound A Benzyl Ester, Cyhalofop-butyl, and Triclopyr Trimethylammonium (TEA) Salt Ternary Herbicidal Compositions on Weed Control in a Rice Cropping System.

| Compound A Benzyl Ester | Cyhalofop-butyl | Triclopyr TEA | Visual Weed Control (%) - 21 DAA ECHCG | |
| --- | --- | --- | --- | --- |
| gae/ha | gai/ha | gae/ha | Obs | Exp |
| 1.09 | 0 | 0 | 0 | — |
| 2.19 | 0 | 0 | 7 | — |
| 0 | 22.5 | 0 | 0 | — |
| 0 | 45 | 0 | 3 | — |
| 0 | 0 | 17.5 | 0 | — |
| 1.09 | 22.5 | 17.5 | 25 | 0 |
| 2.19 | 22.5 | 17.5 | 48 | 7 |
| 1.09 | 45 | 17.5 | 37 | 3 |
| 2.19 | 45 | 17.5 | 48 | 10 |

| Compound A Benzyl Ester | Cyhalofop-butyl | Triclopyr TEA | Visual Weed Control (%) - 21 DAA ECHCG | |
| --- | --- | --- | --- | --- |
| gae/ha | gai/ha | gai/ha | Obs | Exp |
| 4 | 0 | 0 | 25 | — |
| 8 | 0 | 0 | 45 | — |
| 16 | 0 | 0 | 99 | — |
| 0 | 45 | 0 | 30 | — |
| 0 | 0 | 35 | 0 | — |
| 4 | 45 | 35 | 100 | 48 |
| 8 | 45 | 35 | 100 | 62 |
| 16 | 45 | 35 | 95 | 99 |

| Compound A Benzyl Ester | Cyhalofop-butyl | Triclopyr TEA | Visual Weed Control (%) - 21 DAA SCPJU | |
| --- | --- | --- | --- | --- |
| gae/ha | gai/ha | gae/ha | Obs | Exp |
| 2.19 | 0 | 0 | 77 | — |
| 0 | 22.5 | 0 | 0 | — |
| 0 | 45 | 0 | 0 | — |
| 0 | 0 | 17.5 | 8 | — |
| 2.19 | 22.5 | 17.5 | 93 | 79 |
| 2.19 | 45 | 17.5 | 88 | 79 |

TABLE 66

Synergistic Activity of In-Water Applications of Compound A Benzyl Ester, Cyhalofop-butyl, and Benfuresate Ternary Herbicidal Compositions on Weed Control in a Rice Cropping System.

| Compound A Benzyl Ester | Cyhalofop-butyl | Benfuresate | Visual Weed Control (%) - 21 DAA ECHCG | |
| --- | --- | --- | --- | --- |
| gae/ha | gai/ha | gai/ha | Obs | Exp |
| 4 | 0 | 0 | 25 | — |
| 8 | 0 | 0 | 45 | — |
| 16 | 0 | 0 | 99 | — |
| 0 | 45 | 0 | 30 | — |
| 0 | 0 | 150 | 0 | — |
| 4 | 45 | 150 | 95 | 48 |
| 8 | 45 | 150 | 95 | 62 |
| 16 | 45 | 150 | 100 | 99 |

TABLE 67

Synergistic Activity of In-Water Applications of Compound A Benzyl Ester, Cyhalofop-butyl, and Benzobicyclon Ternary Herbicidal Compositions on Weed Control in a Rice Cropping System.

| Compound A Benzyl Ester | Cyhalofop-butyl | Benzobicyclon | Visual Weed Control (%) - 21 DAA ECHCG | |
| --- | --- | --- | --- | --- |
| gae/ha | gai/ha | gai/ha | Obs | Exp |
| 4 | 0 | 0 | 25 | — |
| 0 | 45 | 0 | 30 | — |

TABLE 67-continued

Synergistic Activity of In-Water Applications of Compound A Benzyl Ester, Cyhalofop-butyl, and Benzobicyclon Ternary Herbicidal Compositions on Weed Control in a Rice Cropping System.

| 0 | 0 | 100 | 20 | — |
| 4 | 45 | 100 | 100 | 58 |

| Compound A Benzyl Ester | Cyhalofop-butyl | Benzobicyclon | Visual Weed Control (%) - 24 DAA ECHOR | |
| --- | --- | --- | --- | --- |
| gae/ha | gai/ha | gai/ha | Obs | Exp |
| 4 | 0 | 0 | 0 | — |
| 8 | 0 | 0 | 0 | — |
| 16 | 0 | 0 | 10 | — |
| 0 | 90 | 0 | 25 | — |
| 0 | 0 | 25 | 10 | — |
| 0 | 0 | 50 | 10 | — |
| 4 | 90 | 25 | 35 | 33 |
| 8 | 90 | 25 | 40 | 33 |
| 16 | 90 | 25 | 100 | 39 |
| 4 | 90 | 50 | 20 | 33 |
| 8 | 90 | 50 | 100 | 33 |
| 16 | 90 | 50 | 85 | 39 |

| Compound A Benzyl Ester | Cyhalofop-butyl | Benzobicyclon | Visual Weed Control (%) - 24 DAA FIMMI | |
| --- | --- | --- | --- | --- |
| gae/ha | gai/ha | gai/ha | Obs | Exp |
| 4 | 0 | 0 | 0 | — |
| 8 | 0 | 0 | 50 | — |
| 16 | 0 | 0 | 30 | — |
| 0 | 180 | 0 | 20 | — |
| 0 | 0 | 50 | 68 | — |
| 4 | 180 | 50 | 88 | 74 |
| 8 | 180 | 50 | 100 | 87 |
| 16 | 180 | 50 | 100 | 82 |

TABLE 68

Synergistic Activity of In-Water Applications of Compound A Benzyl Ester, Cyhalofop-butyl, and Pyraclonil Ternary Herbicidal Compositions on Weed Control in a Rice Cropping System.

| Compound A Benzyl Ester | Cyhalofop-butyl | Pyraclonil | Visual Weed Control (%) - 21 DAA ECHCG | |
| --- | --- | --- | --- | --- |
| gae/ha | gai/ha | gai/ha | Obs | Exp |
| 4 | 0 | 0 | 25 | — |
| 8 | 0 | 0 | 45 | — |
| 16 | 0 | 0 | 99 | — |
| 0 | 45 | 0 | 30 | — |
| 0 | 0 | 22.5 | 30 | — |
| 4 | 45 | 22.5 | 100 | 63 |
| 8 | 45 | 22.5 | 100 | 73 |
| 16 | 45 | 22.5 | 100 | 100 |

| Compound A Benzyl Ester | Cyhalofop-butyl | Pyraclonil | Visual Weed Control (%) - 21 DAA SCPMA | |
| --- | --- | --- | --- | --- |
| gae/ha | gai/ha | gai/ha | Obs | Exp |
| 4 | 0 | 0 | 0 | — |
| 8 | 0 | 0 | 0 | — |

TABLE 68-continued

Synergistic Activity of In-Water Applications of Compound A Benzyl Ester, Cyhalofop-butyl, and Pyraclonil Ternary Herbicidal Compositions on Weed Control in a Rice Cropping System.

| 16 | 0 | 0 | 0 | — |
| 0 | 22.5 | 0 | 0 | — |
| 0 | 45 | 0 | 0 | — |
| 0 | 0 | 22.5 | 78 | — |
| 4 | 22.5 | 22.5 | 83 | 78 |
| 8 | 22.5 | 22.5 | 100 | 78 |
| 16 | 22.5 | 22.5 | 93 | 78 |
| 4 | 45 | 22.5 | 95 | 78 |
| 8 | 45 | 22.5 | 98 | 78 |
| 16 | 45 | 22.5 | 90 | 78 |

TABLE 69

Synergistic Activity of In-Water Applications of Compound A Benzyl Ester, Cyhalofop-butyl, and Mefenacet Ternary Herbicidal Compositions on Weed Control in a Rice Cropping System.

| Compound A Benzyl Ester | Cyhalofop-butyl | Mefenacet | Visual Weed Control (%) - 21 DAA CYPRO | |
| --- | --- | --- | --- | --- |
| gae/ha | gai/ha | gai/ha | Obs | Exp |
| 4 | 0 | 0 | 3 | — |
| 8 | 0 | 0 | 33 | — |
| 0 | 90 | 0 | 0 | — |
| 0 | 180 | 0 | 0 | — |
| 0 | 0 | 75 | 0 | — |
| 0 | 0 | 150 | 0 | — |
| 4 | 90 | 75 | 15 | 3 |
| 8 | 90 | 75 | 55 | 33 |
| 4 | 90 | 150 | 75 | 3 |
| 8 | 90 | 150 | 50 | 33 |
| 4 | 180 | 75 | 68 | 3 |
| 8 | 180 | 75 | 60 | 33 |
| 4 | 180 | 150 | 35 | 3 |
| 8 | 180 | 150 | 63 | 33 |

TABLE 70

Synergistic Activity of In-Water Applications of Compound A Benzyl Ester, Cyhalofop-butyl, and Pretilachlor.

| Compound A Benzyl Ester | Cyhalofop-butyl | Pretilachlor | Visual Weed Control (%) - 21 DAA CYPRO | |
| --- | --- | --- | --- | --- |
| gae/ha | gai/ha | gai/ha | Obs | Exp |
| 4 | 0 | 0 | 3 | — |
| 8 | 0 | 0 | 33 | — |
| 0 | 180 | 0 | 0 | — |
| 0 | 0 | 25 | 0 | — |
| 0 | 0 | 50 | 0 | — |
| 4 | 180 | 25 | 30 | 3 |
| 8 | 180 | 25 | 100 | 33 |
| 4 | 180 | 50 | 35 | 3 |
| 8 | 180 | 50 | 55 | 33 |

TABLE 71

Synergistic Activity of In-Water Applications of Compound A Benzyl Ester, Metamifop, and Penoxsulam Ternary Herbicidal Compositions on Weed Control in a Rice Cropping System.

| Compound A Benzyl Ester | Penoxsulam | Metamifop | Visual Weed Control (%) - 24 DAA ECHOR | |
|---|---|---|---|---|
| gae/ha | gai/ha | gai/ha | Obs | Exp |
| 8 | 0 | 0 | 10 | — |
| 16 | 0 | 0 | 25 | — |
| 0 | 5 | 0 | 65 | — |
| 0 | 10 | 0 | 93 | — |
| 0 | 0 | 25 | 10 | — |
| 0 | 0 | 50 | 18 | — |
| 8 | 5 | 25 | 83 | 72 |
| 16 | 10 | 25 | 83 | 95 |
| 8 | 5 | 50 | 100 | 74 |
| 16 | 10 | 50 | 100 | 95 |

CYPRO *Cyperus rotundus* L. — nutsedge, purple
ECHCG *Echinochloa crusgalli* (L.) Beauv. — barnyardgrass
ECHOR *Echinochloa oryzoides* (Ard.) Fritsch — watergrass, early
FIMMI *Fimbristylis miliacea* (L.) Vahl — fringerush, globe
SCPJU *Schoenoplectus juncoides* (Roxb.) Palla — bulrush, Japanese
SCPMA *Bolboschoenus maritimus* (L.) Palla or *Schoenoplectus maritimus* (L.) Lye — clubrush, sea
gae/ha = grams acid equivalent per hectare
gai/ha = grams active ingredient per hectare
Obs = observed value
Exp = expected value as calculated by Colby's equation
DAA = days after application

What is claimed is:

1. A herbicidal composition, comprising:
a herbicidally effective amount of (a) a compound of the formula (I):

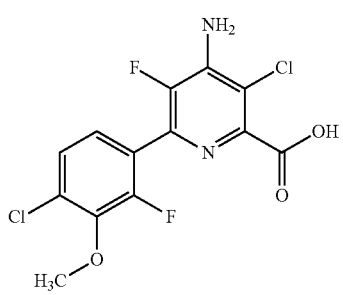

(I)

or an agriculturally acceptable salt or ester thereof; and
(b) at least one ACCase inhibitor, or a salt or ester thereof, selected from the group consisting of clethodim, clodinafop-propargyl, cyhalofop-R-butyl, diclofop-methyl, fenoxaprop-P-ethyl, fluazifop-P-butyl, haloxyfop-R-methyl, metamifop, pinoxaden, profoxydim, quizalofop-P-ethyl, sethoxydim or tralkoxydim, wherein (a) and (b) are present in the composition in a ratio such that the composition exhibits herbicidal synergy.

2. The composition of claim 1, wherein (a) is a $C_{1-4}$ alkyl or benzyl ester of compound (I).

3. The composition of claim 2, wherein (a) is a benzyl ester of compound (I).

4. The composition of claim 1, wherein (a) is the compound of formula (I), which is the carboxylic acid.

5. The composition of claim 1, wherein (b) is cyhalofop-R-butyl, or a carboxylic acid, carboxylate salt, or ester thereof, wherein the composition further comprises penoxsulam, bentazon-sodium, triclopyr, bispyribac-sodium, imazamox, benzobicyclon, quinclorac, glyphosate, glufosinate, benfuresate, fentrazamide, indanofan, ipfencarbazone, mefenacet, oxazichlomefone, pretilachlor, propyrisulfuron, pyraclonil, pyriftalid, or pyrimisulfan, or an agriculturally acceptable salt, carboxylic acid, carboxylate salt, or ester thereof, in the composition.

6. A method of controlling undesirable vegetation, comprising the steps of contacting the vegetation or the locus thereof with or applying to the soil or water to prevent the emergence or growth of the vegetation, a herbicidally effective amount of a combination comprising (a) a compound of the formula (I):

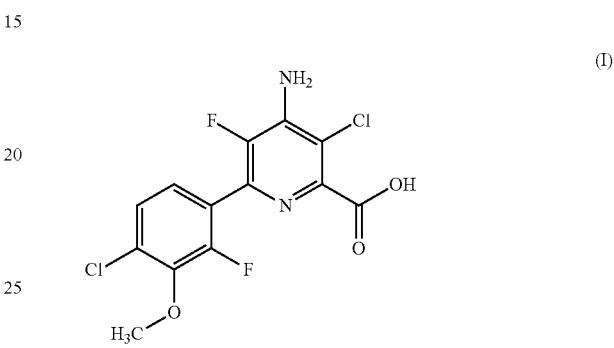

(I)

or an agriculturally acceptable salt or ester of thereof, and (b) an ACCase inhibitor or an agriculturally acceptable salt or ester therein selected from the group consisting of clethodim, clodinafop-propargyl, cyhalofop-R-butyl, diclofop-methyl, fenoxaprop-P-ethyl, fluazifop-P-butyl, haloxyfop-R-methyl, metamifop, pinoxaden, profoxydim, quizalofop-P-ethyl, sethoxydim or tralkoxydim, wherein (a) and (b) are present in the combination in ratio such that the combination exhibits herbicidal synergy; wherein the undesirable vegetation is controlled in rice, cereals, wheat, barley, oats, rye, sorghum, maize, sugarcane, soybean, pastures, grasslands, rangelands, fallowland and turf.

7. The method of claim 6, wherein the undesirable vegetation is immature.

8. The method of claim 6, wherein the (a) and (b) are applied to the water.

9. The method of claim 8, wherein the water is part of a flooded rice paddy.

10. The method of claim 6, wherein the (a) and (b) are applied post-emergently and/or post emergently to the undesirable vegetation or crop.

11. The method of claim 6, wherein the undesirable vegetation is controlled in glyphosate-, 5-enolpyruvylshikimate-3-phosphate synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase inhibitor-, imidazolinone-, sulfonylurea-, pyrimidinylthiobenzoate-, triazolopyrimidine-, sulfonylaminocarbonyltriazolinone-, acetolactate synthase or acetohydroxy acid synthase inhibitor-, 4-hydroxyphenylpyruvate dioxygenase inhibitor-, phytoene desaturase inhibitor-, carotenoid biosynthesis inhibitor-, protoporphyrinogen oxidase inhibitor-, cellulose biosynthesis inhibitor-, mitosis inhibitor-, microtubule inhibitor-, long chain fatty acid inhibitor-, fatty acid and lipid biosynthesis inhibitor-, photosystem I inhibitor-, photosystem II inhibitor-, triazine-, or bromoxynil-tolerant crops.

12. The method of claim 11, wherein the tolerant crop possesses multiple or stacked traits conferring tolerance to multiple herbicides.

13. The method of claim 6, wherein the undesirable vegetation comprises a herbicide resistant or tolerant plant.

14. The method of claim 13, wherein the resistant or tolerant plant is resistant or tolerant to multiple herbicides.

15. The method of claim 13, wherein the resistant or tolerant plant is resistant or tolerant to acetolactate synthase or acetohydroxy acid synthase inhibitors, photosystem II inhibitors, acetyl CoA carboxylase inhibitors, synthetic auxins, auxin transport inhibitors, photosystem I inhibitors, 5-enolpyruvylshikimate-3-phosphate synthase inhibitors, microtubule assembly inhibitors, fatty acid and lipid synthesis inhibitors, protoporphyrinogen oxidase inhibitors, carotenoid biosynthesis inhibitors, long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.

\* \* \* \* \*